US008784815B2

(12) United States Patent
Korman et al.

(10) Patent No.: US 8,784,815 B2
(45) Date of Patent: *Jul. 22, 2014

(54) HUMAN CTLA-4 ANTIBODIES AND THEIR USES

(71) Applicants: Alan J. Korman, Piedmont, CA (US); Edward L. Halk, Sunnyvale, CA (US); Nils Lonberg, Woodside, CA (US); Yashwant M. Deo, East Brunswick, NJ (US); Tibor P. Keler, Ottsville, PA (US)

(72) Inventors: Alan J. Korman, Piedmont, CA (US); Edward L. Halk, Sunnyvale, CA (US); Nils Lonberg, Woodside, CA (US); Yashwant M. Deo, East Brunswick, NJ (US); Tibor P. Keler, Ottsville, PA (US)

(73) Assignee: Medarex, L.L.C., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/666,672

(22) Filed: Nov. 1, 2012

(65) Prior Publication Data

US 2013/0136749 A1 May 30, 2013

Related U.S. Application Data

(60) Continuation of application No. 13/198,263, filed on Aug. 4, 2011, now Pat. No. 8,318,916, which is a division of application No. 12/564,756, filed on Sep. 22, 2009, now Pat. No. 8,017,114, which is a continuation of application No. 09/948,939, filed on Sep. 7, 2001, now Pat. No. 7,605,238, which is a continuation-in-part of application No. 09/644,668, filed on Aug. 24, 2000, now Pat. No. 6,984,720.

(60) Provisional application No. 60/150,452, filed on Aug. 24, 1999.

(51) Int. Cl.
A61K 39/395 (2006.01)
C07K 16/28 (2006.01)

(52) U.S. Cl.
CPC ......... A61K 39/3955 (2013.01); C07K 16/2818 (2013.01); C07K 2316/96 (2013.01); C07K 2317/21 (2013.01)
USPC ............... 424/144.1; 424/142.1; 530/388.75; 530/388.22; 530/388.15

(58) Field of Classification Search
CPC ................... A61K 39/3955; A61K 2039/505; C07K 16/2818; C07K 2316/96; C07K 2317/21
See application file for complete search history.

(56) References Cited

U.S. PATENT DOCUMENTS

| 4,399,216 A | 8/1983 | Axel et al. |
| 4,681,581 A | 7/1987 | Coates |
| 4,683,195 A | 7/1987 | Mullis et al. |
| 4,683,202 A | 7/1987 | Mullis |
| 4,735,210 A | 4/1988 | Goldenberg |
| 4,740,461 A | 4/1988 | Kaufman |
| 4,816,397 A | 3/1989 | Boss et al. |
| 4,921,040 A | 5/1990 | Ueruenduel et al. |
| 4,959,455 A | 9/1990 | Clark et al. |
| 5,101,827 A | 4/1992 | Goldenberg |
| 5,151,510 A | 9/1992 | Stec et al. |
| 5,194,594 A | 3/1993 | Khawli et al. |
| 5,434,131 A | 7/1995 | Lisley et al. |
| 5,530,101 A | 6/1996 | Queen et al. |
| 5,545,806 A | 8/1996 | Lonberg et al. |
| 5,545,807 A | 8/1996 | Surani et al. |
| 5,556,763 A | 9/1996 | Ochoa et al. |
| 5,569,825 A | 10/1996 | Lonberg et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| RE35,500 E | 5/1997 | Rhodes |
| 5,633,425 A | 5/1997 | Lonberg et al. |
| 5,643,763 A | 7/1997 | Dunn et al. |
| 5,648,471 A | 7/1997 | Buttram et al. |
| 5,661,016 A | 8/1997 | Lonberg et al. |
| 5,693,761 A | 12/1997 | Queen et al. |
| 5,693,792 A | 12/1997 | Torri et al. |
| 5,697,902 A | 12/1997 | Goldenberg |
| 5,703,057 A | 12/1997 | Johnston et al. |
| 5,714,350 A | 2/1998 | Co et al. |
| 5,721,367 A | 2/1998 | Kay et al. |
| 5,733,743 A | 3/1998 | Johnston et al. |
| 5,741,957 A | 4/1998 | Deboer et al. |
| 5,750,172 A | 5/1998 | Meade et al. |
| 5,756,687 A | 5/1998 | Denman et al. |
| 5,759,546 A | 6/1998 | Weinberg et al. |
| 5,770,197 A | 6/1998 | Lisley et al. |
| 5,770,429 A | 6/1998 | Lonberg et al. |
| 5,773,253 A | 6/1998 | Lisley et al. |
| 5,777,085 A | 7/1998 | Co et al. |
| 5,789,215 A | 8/1998 | Berns et al. |
| 5,789,650 A | 8/1998 | Lonberg et al. |

(Continued)

FOREIGN PATENT DOCUMENTS

| CA | 2205680 | 11/1998 |
| EP | 256055 | 8/1991 |
| EP | 323997 | 4/1993 |
| EP | 0613944 | 9/1994 |
| EP | 338841 | 3/1995 |

(Continued)

OTHER PUBLICATIONS

Rudikoff et al. 1982, Proc. Natl. Acad. Sci. USA, 79: 1979-1983.*
Panka et al., 1988, Proc. Natl. Acad. Sci. USA, 85: 3080-3084.*
U.S. Appl. No. 60/293,042, filed May 23, 2001, Mueller et al.
U.S. Appl. No. 60/372,284, filed Apr. 12, 2002, Davis et al.
U.S. Appl. No. 09/705,346, filed Nov. 2, 2000, Allison et al.

(Continued)

Primary Examiner — Ilia Ouspenski
(74) Attorney, Agent, or Firm — Baker Botts L.L.P.

(57) ABSTRACT

The present invention provides novel human sequence antibodies against human CTLA-4 and methods of treating human diseases, infections and other conditions using these antibodies.

29 Claims, 25 Drawing Sheets

(56) References Cited

U.S. PATENT DOCUMENTS

| | | | |
|---|---|---|---|
| 5,811,097 A | 9/1998 | Allison et al. |
| 5,814,318 A | 9/1998 | Lonberg et al. |
| 5,821,332 A | 10/1998 | Godfrey et al. |
| 5,827,690 A | 10/1998 | Meade et al. |
| 5,844,095 A | 12/1998 | Linsley et al. |
| 5,855,887 A | 1/1999 | Allison et al. |
| 5,874,299 A | 2/1999 | Lonberg et al. |
| 5,877,397 A | 3/1999 | Lonberg et al. |
| 5,885,796 A | 3/1999 | Linsley et al. |
| 5,916,771 A | 6/1999 | Hori et al. |
| 5,939,598 A | 8/1999 | Kucherlapati et al. |
| 5,968,510 A | 10/1999 | Lisley et al. |
| 5,977,318 A | 11/1999 | Lisley et al. |
| 6,051,227 A | 4/2000 | Allison et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,207,156 B1 | 3/2001 | Kuchroo et al. |
| 6,255,458 B1 | 7/2001 | Lonberg et al. |
| 6,632,927 B2 * | 10/2003 | Adair et al. ............... 530/387.3 |
| 6,682,736 B1 | 1/2004 | Hanson et al. |
| 6,719,972 B1 | 4/2004 | Gribben et al. |
| 6,984,720 B1 | 1/2006 | Korman et al. |
| 7,034,121 B2 | 4/2006 | Carreno et al. |
| 7,229,628 B1 | 6/2007 | Allison et al. |
| 7,410,253 B2 | 8/2008 | Habermann et al. |
| 7,452,535 B2 | 11/2008 | Davis et al. |
| 7,465,446 B2 | 12/2008 | Lowy et al. |
| 7,605,238 B2 | 10/2009 | Korman et al. |
| 2002/0039581 A1 | 4/2002 | Carreno et al. |
| 2002/0086014 A1 | 7/2002 | Korman et al. |
| 2002/0182218 A1 | 12/2002 | Nicolette |
| 2003/0086930 A1 | 5/2003 | Mueller et al. |
| 2003/0175250 A1 | 9/2003 | Jager et al. |
| 2005/0201994 A1 | 9/2005 | Halk et al. |
| 2005/0249700 A1 | 11/2005 | Allison et al. |
| 2006/0034844 A1 | 2/2006 | Allison et al. |
| 2007/0160619 A1 | 7/2007 | Nichol et al. |
| 2007/0248595 A1 | 10/2007 | Yang et al. |
| 2009/0074752 A1 | 3/2009 | Lowy et al. |
| 2009/0117037 A1 | 5/2009 | Davis et al. |
| 2009/0217401 A1 | 8/2009 | Korman et al. |
| 2010/0047244 A1 | 2/2010 | Korman et al. |

FOREIGN PATENT DOCUMENTS

| | | |
|---|---|---|
| EP | 216846 | 4/1995 |
| EP | 0682039 | 11/1995 |
| EP | 463151 | 6/1996 |
| EP | 546073 | 9/1997 |
| EP | 1262193 | 12/2002 |
| WO | WO9004036 | 4/1990 |
| WO | WO9110741 | 7/1991 |
| WO | WO9203918 | 3/1992 |
| WO | WO9222645 | 12/1992 |
| WO | WO9222647 | 12/1992 |
| WO | WO9222670 | 12/1992 |
| WO | WO9300431 | 1/1993 |
| WO | WO9312227 | 6/1993 |
| WO | WO9402602 | 2/1994 |
| WO | WO9425585 | 11/1994 |
| WO | WO9429444 | 12/1994 |
| WO | WO9501994 | 1/1995 |
| WO | WO9503408 | 2/1995 |
| WO | WO9505464 | 2/1995 |
| WO | WO9523859 | 9/1995 |
| WO | WO9524217 | 9/1995 |
| WO | WO9533770 | 12/1995 |
| WO | WO9534320 | 12/1995 |
| WO | WO9614436 | 5/1996 |
| WO | WO9614865 | 5/1996 |
| WO | WO9622380 | 7/1996 |
| WO | WO9633735 | 10/1996 |
| WO | WO9634096 | 10/1996 |
| WO | WO9707671 | 3/1997 |
| WO | WO9713852 | 4/1997 |
| WO | WO9720574 | 6/1997 |
| WO | WO9738137 | 10/1997 |
| WO | WO98/24893 | 6/1998 |
| WO | WO9824884 | 6/1998 |
| WO | WO9824893 | 6/1998 |
| WO | WO9837757 | 9/1998 |
| WO | WO9842752 | 10/1998 |
| WO | WO9846996 | 10/1998 |
| WO | WO9850433 | 11/1998 |
| WO | WO0000569 | 1/2000 |
| WO | WO0010383 | 3/2000 |
| WO | WO0032231 | 6/2000 |
| WO | WO0037504 | 6/2000 |
| WO | WO0114424 | 3/2001 |

OTHER PUBLICATIONS

U.S. Appl. No. 10/319,832, filed Dec. 12, 2002, Allison et al.
U.S. Appl. No. 10/409,705, filed Apr. 4, 2003, Korman, et al.
U.S. Appl. No. 12/564,756, filed Sep. 22, 2009.
U.S. Appl. No. 11/040,846, filed Jan. 20, 2005.
U.S. Appl. No. 12/246,791, filed Oct. 7, 2008.
U.S. Appl. No. 12/259,075, filed Oct. 17, 2008.
U.S. Appl. No. 11/557,835, filed Nov. 8, 2006.
U.S. Appl. No. 11/567,846, filed Dec. 7, 2006.
Anderson, DE, et al., "Paradoxical inhibition of T-cell function in response to CTLA-4 blockade; heterogeneity within the human T-cell population," Nature Medicine (2000), vol. 6, pp. 211-214.
Bailint et al., "Antibody Engineering by Parsimonious Mutagenesis," *Gene*, 137(1993), 109-118.
Barbas et al., "Recognition of DNA by Synthetic Antibodies," *J. Am. Chem. SOC.* (1994) 116:2161-2162.
Barbas et al., "Human autoantibody recognition of DNA," *Proc. Natl. Acad. Sci. USA* (1995) 92:2529-2533.
Beiboer et al., "Guided Selection of a Pan Carcinoma Specific Antibody Reveals Binding Characteristics yet Structural Divergence Between the Original Murine Antibody and its Human Equivalent," *J. Mol. Biol.* (2000) 296:833-849.
Blair et al., "Cutting edge: CTLA-4 ligation delivers a unique signal to resting human CD4 T cells that inhibits interleukin-2 secretion but allows Bcl-XL induction," The J. of Immunology, vol. 22: 1767 (1998).
Bluestone (1997) J. Immunol. 158:1989-1993.
Bluestone J.A., Immunity 2:555-559 (1995).
Boon, T. et al., (1992) Advances in Cancer Res. 58: 177-210.
Brunet et al., Nature 328:267-270 (1987).
Brunet et al., Immunol. Rev. 103-21-36 (1988).
Chambers (1997) Curr. Opin. Immunol. 9:396-404.
Chambers et al., Immunity. 7:885-895 (1997).
Chambers, CA, et al., "Thymocyte development is normal in CTLA-4-deficient mice," Proceedings of the National Academy of Sciences USA (1997), vol. 94, pp. 9296-9301.
Chang and Siegel "Genetic and immunological properties of phage-displayed human anti-Rh(D) antibodies: implications for Rh(D) epitope topology," *Am. Soc. Hematol* (1998) 21(8):3066-3078.
Chen et al., "Costimulation of Antitumor Immunity by the B7 Counterreceptor for the T Lymphocyte Molecules CD28 and CTLA-4," Cell 71:1093-1102 (1992).
Chen, J. et al., "Immunoglobulin gene rearrangement in b cell deficient mice generated by targeted deletion of th Jh locus," International Immunology, vol. 5, No. 6, 647-565, (1993).
Choi, T. et al., "Transgenic mice containing a human heavy chain immunoglobulin gene fragment cloned in a yeast artificial chromosome," Nature Genetics, vol. 4, Jun. 1993.
Clark (1986) Human Immunol. 16:100-113.
Damle et al., "Costimulation of T Lymphocytes with Integrin Ligands Intercellular Adhesion Molecule-1 or Vascular Cell Adhesion Molecule-1 Induces Functional Expression of CTLA-4, A Second Receptor for B7," Journal of Immunology 152:2686-2697 (1994).
Damle et al., Proc. Natl. Acad. Sci. 78:5096-6001 (1981).

(56) References Cited

OTHER PUBLICATIONS

Dariavach et al., Eur. J. Immunol. 18:1901-1905 (1988).
Ditzel et al., "Determinants of Polyreactivity in a Large Panel of Recombinant Human Antibodies from HIV-1 Infection," *The Journal of Immunology* (1996) 157:739-749.
Egen et al., "CTLA-4: New Insights Into Its Biological Function and Use in Tumor Immunotherapy", Nature Immunology, vol. 3, No. 7, Jul. 2002.
Elsas et al., "Combination immunotherapy of B16 melanoma using anti-cytoxic T lymphocyte-associated antigen 4 subcutaneous and metastatic tumors accompanied by autoimmune depigmentation," J. Exp. Med. 190:355-368. (1999).
Fishwild et al., "High-avidity human lgGk monoclonal antibodies from a novel strain of minilocus mice," Nature Biotechnology 14:845-851 (1996).
Frankel, Arther E., "Increased Sophistication of Immunotixins; Clinical Cancer Research", vol. 8, 942-944, Apr. 2002.
Freeman (1987) J. Immunol. 138:3260-3267.
Freeman (1989) J. Immunol. 143:2714-2722.
Freeman, G.J. et al., J. Immunol. 149(12): 3795-3801 (1992).
Freeman et al., "Uncovering of Functional Alternative CTLA-4 Counter-Receptor in B7-Deficient Mice," Science 262:907-909 (1993).
Green, L. et al, "Antigen-specific human monoclonal antibodies from mice engineered with human lg heavy and light chain YACs," Nature Genetics, vol. 7, May 1994.
Green, L. et al., "Regulation of B Cell Development by Variable Gene Complexity in Mice Reconstituted with Human Immunoglobulin Yeast Artificial Chromosome," J. Exp. Med., vol. 188, No. 3, 483-495, Aug. 3, 1998.
Gribben, G, et al., Alloantigen and concomitant CTLA4 signaling induces clonal deletion of alloreactive T cells, Blood (1994), vol. 84, pp. 397a (meeting abstract).
Gribben et al., "CTLA-4 mediates antigen-specific apoptosis of human T cells," Proc. Natl. Acad. Sci. USA 92: 811-815 (1995).
Hanjo and Matsuda, "Immunoglobulin heavy chain loci of mouse and human," *Immunoglobulin Genes*, Second Ed., (1995) edited by To Hanjo and F.W. Alt, Academic Press, Chapter 7.
Harding et al., "CD28-Mediated Signalling Co-Stimulates Murine T Cells and Prevents Induction of Anergy in T-Cell Clones," Nature 356:607-609 (1992).
Heslop, HE, "Cytokine gene transfer in the therapy of malignancy," Baillieres Clinical Haematology (1994), vol. 7, pp. 135-151 (abstract only), Medline 8038497.
Hurwitz et al., "CTLA-4 blockade synergizes with tumor-derived granulocyte-macrophage colony-stimulating factor for treatment of an experimental mammary carcinoma," Proc. Natl. Acad. Sci. USA 95: 10057-10071 (1998).
Hurwitz et al., "Immunotherapy of primary prostate cancer in a transgenic model using a combination of CTLA-4 blockade and tumor cell vaccine," Cancer Research 60:2444-2448 (2000).
Ishida et al., "Production of a diverse repertoire of human antibodies in genetically engineered mice," *Microbiol. Immunol.* (1998) 42(3):143-50.
Jenkins, M.K., "The Ups and Downs of T Cell Costimulation," Immunity 1:443-446 (1994).
June et al., "The B7 and CD28 Receptor Families," Immunology Today, 15(7):321-331 (1994).
Kearney (1995) J. Immunol. 155:1032-1036.
Klimka et al., "Human anti-CD30 recombinant antibodies by guided phage antibody selection using cell panning," *British Journal of Cancer* (2000) 83(2):252-260.
Kohno et al., Cell. Immunol. 131-1-10 (1990).
Krummel et al., "Superantigen responses and co-stimulation: CD28 and CTLA-4 have opposing effects on T cell expansion in vitro and in vivo," (1996) Int'l Immunol. 8:519-523.
Krummel et al., "CD28 and CTLA-4 have opposing effects on the response of T cells to stimulation," (1995) J. Exp. Med. 182:459-465.
Krummel et al., "CTLA-4 engagement inhibits IL-2 accumulation activation of resting T-cells," J. Exp. Med 183:2533-2540 (1996).

Kwon et al., "Manipulation of T Cell consimulatory and inhibitory signals for immunotherapy of prostate cancer," Proc. Natl. Acad. Sci. USA 94:8099-8103 (1997).
Lafage-Pochitaloff et al., Immunogenetics 31:198-201 (1990).
Leach, DR, et al., "Enhancement of antitumor immunity by CTLA-4 blockade," Science (1996), vol. 271, pp. 1734-1736 (1996).
Lee, K-H, et al., "Increased vaccine-specific T cell frequency after peptide-based vaccination correlates with increased susceptibility to in vitro stimulation but does not lead to tumor regression," Journal of Immunology (1999), vol. 163, pp. 6292-6300.
Lenschow et al., "Long-Term Survival of Xenogeneic Pancreatic Islet Grafts Induced by CTLA4lg," Science 257:789-792 (1992).
Lenschow et al., "Expression and Functional Significance of an Additional Ligand for CTLA-4," Proc. Natl. Acad. Sci. USA 90:11054-11058 (1993).
Lesslauer et al., Eur. J. Immunol. 16:1289-1296 (1986).
Lin et al., "Long-Term Acceptance of Major Histocompatibility Complex Mismatched Cardiac Allografts Induced by CTLA4lg Plus Donor-Specific Transfusion," J. Exp. Med. 178:1801-1806 (1993).
Lindsten et al., "Characterization of CTLA-4 Structure and Expression on Human T Cells"; The Journal of Immunology, vol. 151, 3489-3499, No. 7, Oct. 1, 1993.
Lindsten et al., Science 244:339-343 (1989).
Linsley et al., "Coexpressiona nd functional cooperation of CTLA-4 and CD28 on activated T lymphocytes" J. Exp. Med. 176:1595-1604 (1992).
Linsley et al. "CTLA-4 is a second receptor for the B cell activation antigen B7," J. Exp. Med. 174:561-569 (1991).
Linsley et al., J. Exp. Med. 173:721-730 (1991).
Linsley et al., Proc. Natl. Acad. Sci. USA 87:2031-5035 (1990).
Linsley, P.S., "Distinct roles for CD28 and Cytotoxic T Lymphocyte-associated molecule-4 Receptors during T Cell Activation?", J. Exp. Med., The Rockefeller University Press, vol. 182, 289-292, Aug. 1995.
Linsley et al., "Immunosuppression in Vivo by a Soluble Form of the CTLA-4 T Cell Activation Molecule," Science 257:792-795 (1992).
Linsley, P.S., et al., J. Immunol. 150: 3161-3169 (1993).
Linsley, P.S. and J.A. Ledbetter, "The Role of the CD28 Receptor During T Cell Responses to Antigen," Ann. Rev. Immunol. 11:191-212 (1993).
Lonberg, N. et al, "Antigen-specific human antibodies from mice comprising four distinct genetic modifications," Nature, vol. 368, Apr. 28, 1994.
Longberg et al., "Human antibodies from transgenic mice," International Review of Immunology 13:65-93 (1995).
Luhder (1998) J. Exp. Med. 187:427-432.
Matsui (1999) J. Immnol. 162:4326-4335.
McCoy et al., "Protective immunity to nematode infection is induced by CTLA-4 blockade," J. Exp. Med 186:183-187 (1997).
Mendez, M. et al., "Functional transplant of megabase human immunoglobulin loci recapitulates human antibody response in mice," Nature Genetics, vol. 15, Feb. 1997.
Mukherji, B. et al., (1995) Proc. Natl. Acad. Sci. USA. 92: 8078-8092.
Neuberger, "Generating high-avidity human Mabs in mice," Nature Biotechnology 14:826 (1996).
Radar A., "A phage display approach for rapid antibody humanization: Designed combinatorial V gene libraries," *Proc. Natl. Acad. Sci. USA* (1998) 95:8910-8915.
Rudikoff et al., 1982, Proc. Natl. Acad. Sci. USA, 79: 1979-1983.
Schäble and Zachau "The variable genes of the human immunoglobulin κ locus" *Biol. Chem.* (1993) 374(11):1001-1022.
Schwartz, R.H., "Costimulation of T Lymphocytes: The Role of CD28, CTLA-4, and B7/BB1 in Interleukin-2 Production and Immunotherapy," Cell 71:1065-1068 (1992).
Shaw et al., "Adjuvant immunotherapy for patients with melanoma: are patients with melanoma of the head and neck candidates for this therapy?" *Head and Neck* (1997) 19:595-603.
Sotomayor, EM, et al., "In vivo blockade of CTLA-4 enhances the priming of responsive T cells but fails to prevent the induction of tumor antigen-specific tolerance," Proceedings of the National Academy of Science USA (1999), vol. 96, pp. 11476-11481.

(56) References Cited

OTHER PUBLICATIONS

Sullivan, T.J. et al., "Induction of CNS inflammatory disease as a consequence of CTLA-4/B7 blockade," FASEB Journal (1998), vol. 12, pp. A1092 (meeting abstract).
Taylor, L. et al., "A transgenic mouse that expresses a diversity of human sequence heavy and light chain immunoglobulins," Nucleic Acids Research, 1992, vol. 20, No. 23, 6287-6295.
Taylor, L. et al., "Human immunoglobulin transgenes undergo rearrangement, somatic mutation and class switching in mice that lack endogenous IgM," International Immunology, vol. 6, No. 4, 579-591.
Thompson (1997) Immunity 7:445-450.
Thompson et al., Proc. Natl. Acad. Sci 86:1333-1337 (1989).
Timmerman, J.M. et al., "Dendritic cell vaccines for cancer immunotherapy," Annual Review of Medicine (1999), vol. 50, pp. 507-529.
Townsend, S.E. and J.P. Allison, "Tumor Rejection After Direct Costimulation of CD8+ T Cells by B7-Transfected Melanoma Cells," Science 259:368-370 (1993).
Tuaillon, N. et al., "Analysis of Direct and Inverted DJh Rearrangements in a Human Ig Heavy Chain Transgenic Minilocus," The Journal of Immunology, vol. 154: 6453-6465, 1995.
Tuaillon, N. et al., "Human immunoglobulin heavy-chain minilocus recombination in transgenic mice: Gene-segment use in μ and y transcripts," Proc. Natl. Acad. Sci. USA., vol. 99: 3720-3724, Apr. 1993, Immunology.
Turka et al., "T-Cell Activation by the CD28 Ligand B7 is Required for Cardiac Allograft Rejection in vivo," Proc. Natl. Acad. Sci. USA 89:11102-11105 (1992).
Walunas et al., "CTLA-4 ligation blocks CD28-dependant T cell activation," J. Exp. Med 183:2541-2550 (1996).
Walunas et al., "CTLA-4 can function as a negative regulator of T Cell activation," Immunity. 1:405-413 (1994).
Wen Y.J. et al., (1998) Clin. Cancer Res. 4: 957-962.
Wu et al., "CTLA-4-B7 Interaction is Sufficient to Costimulate T Cell Clonal Expansion," J. Exp. Med. 185(7):1327-1335 (1997).
Yang, Y-F, et al., "Enhanced induction of antitumor T-cell responses by cytotoxic lymphocyte-associated molecule-4 blockade: the effect is manifested only at the restricted tumor-bearing stages," Cancer Research (1997), vol. 57, pp. 4036-4041.
Yang et al., "Eradication of established tumors by a fully human monoclonal antibody to the epidermal growth factor receptor without concomitant chemotherapy," Cancer Research 59:1236-1243 (1999).
Yanofsky, S.D. et al., "High affinity type I interleukin receptor antagonists discovered by screening recombinant peptide libraries," (1996) Proc. Natl. Acad. Sci. USA 93: 7381-7386.
Yokochi (1981) J. Immunol. 128:823.
Zachau, "The human immunoglobulin K genes," Immunoglobulin Genes, Second Ed., (1995) edited by To Hanjo and F.W. Alt, Academic Press, Chapter 8.
Zaks, T.Z. and Rosenberg S.A., "Immunization with a peptide epitope (p369-377) from HER-2/neu leads to peptide-specific cytotoxic T lymphocytes that fail to recognize HER-2/neu+ tumors," Cancer Research (1998), vol. 58, pp. 4902-4908.
Zhu, J. et al., "Cytotoxic T lymphocyte-associated antigen 4 (CTLA-4) blockade enhances incidence and severity of experimental autoimmune neuritis in resistant mice," Journal of Neuroimmunology (2001), 115: 111-117.
Ansell et al., "Phase I study of ipilimumab, an anti-CTLA-4 monoclonal antibody, in patients with relapsed and refractory B-cell non-hodgkin lymphoma," Clin. Cancer Res. (2009);15(20):6446-6453.
Attia, et al. "Autoimmunity correlates with tumor regression in patients with metastatic melanoma treated with anti-cytotoxic T-lymphocyte antigen-4." J Clin Oncol. Sep. 1, 2005; vol. 23(25):6043-53.
Balzano, et al."CTLA-4 and CD28: similar proteins, neighbouring genes." Int J Cancer Suppl. 1992;7:28-32.Links.
Bashey et al., "CTLA-4 blockade with ipilimumab to treat relapse of malignancy after allogeneic hematopoietic cell transplantation," Blood (2009);113:1581-1588.

Bashey et al., "Phase I study of a neutralizing monoclonal anti-CTLA-4 antibody (MDX-010) in patients with relapse of malignancy after allogeneic hematopoietic stem cell transplantation," Biology of Blood and Marrow Transplantation (2005);11(2):5.
Beck et al., "Enterocolitis in patients with cancer after antibody blockade of cytotoxic T-lymphocyte-associated antigen 4," J Clin Oncol. (2006);24(15):2283-9.
Beckman et al., "Antibody constructs in cancer therapy", Can. 109: 170-179 (2007).
Bi et al., "Expressions of Fas, CTLA-4 and RhoBTB2 genes in breast carcinoma ad their relationship with clinicopathological factors", Zhonghua Zhong Liu Za Zhi. Oct. 2008; 30(10): 749-53 (Articles is in Chinese, English Abstract submitted).
Brown et al., "Tumor necrosis factor antagonist therapy and lymphoma development", (2002) Arthritis and Rheumatism, 46(12): 3151-3158.
Camacho et al., "Phase I/II Trial of Tremelimumab in patients with metastatic melanoma," J. Clin. Oncol. (2009);27:1075-1081.
Camacho et al., "Phase 1 clinical trial of anti-CTLA4 human monoclonal antibody CP-675,206 in patients (pts) with advanced solid malignancies," J. Clin. Oncol. 2004 ASCO Annual Meeting Proceedings (Post-Meeting Edition), vol. 22, No. 14S (Jul. 15 Suppl.), 2004:2505.
Cancer Therapy Evaluation Program, Common Terminology Criteria for Adverse Events (CTCAE), Version 3.0, DCTD, NCI, NIH, DHHS, Mar. 31, 2003.
Cespedes et al., "Mouse models in oncogenesis and cancer therapy", Clin. Transl. Oncol. 8(5): 318-329 (2006).
Chambers, et al., 1999, "Cytotoxic T lymphocyte antigen-4 (CTLA-4) regulates primary and secondary peptide-specific $CD3^+$ T cell responses," Proc. Natl. Acad. Sci. USA, vol. 96: p. 8603-8608.
Chambers et al., 1998, "Secondary but not primary T cell responses are enhanced in CTLA-4-deficient $CD8^+$ T cells," Eur. J. Immunol., vol. 28: p. 3137-43.
Chambers et al., "CTLA-4-mediated inhibition in regulation of T cell responses: mechanisms and manipulation in tumor immunotherapy", Annu Rev Immunol. (2001); 19:565-94.
Damle et al., "Alloantigen-specific cytotoxic and suppressor T lymphocytes are derived from phenotypically distinct precursors," J Immunol. (1983);131(5):2296-300.
Dennis, C., "Cancer: off by a whisker", Nature 442: 739-741 (2006).
Doyle, et al., 2001, "Induction of cytotoxic T lymphocyte antigen 4 (CTLA-4) restricts clonal expansion of helper T cells," J. Exp. Med., vol. 194: p. 893-902.
Downey et al., "Prognostic factors related to clinical response in patients with metastatic melanoma treated by CTL-associated antigen-4 blockade", Clin. Cancer Res. 13(22): 6681-6688 (Nov. 2007).
European Search Report for EP 03728392.6, dated Apr. 29, 2005.
Falko-Gunter Falkner,—F.3d—, 2006 WL 1453040, 1-15.
Fujimori et al., J. Nuc. Med. 31:1191-1198, (1990).
Gray et al., "Therapeutic potential of immunostimulatory monoclonal antibodies", Clinical Science, 2006, 111:93-106.
Gulley et al., "Future directions in tumor immunotherapy", Nat Clin Pract Oncol. (2007); 4(3): 136-137.
Gura et al., "Systems for identifying new drugs are often faulty", Science 278: 1041-1042 (Nov. 1997).
Hochberg et al., "The benefit/risk profile of TNF-Blocking agents: Findings of a consensus panel", Semin. Arthritis Rheum., 2005, 34:819-836.
Hodi et al., "Immunologic and clinical effects of antibody blockade of cytotoxic T lymphocyte-associated antigen 4 in previously vaccinated cancer patients," PNAS (2008);105(8):3005-3010.
Hodi et al., 2003, "Biologic activity of cytotoxic T lymphocyte-associated antigen 4 antibody blockade in previously vaccinated metastatic melanoma and ovarian carcinoma patients," Proc. Natl. Acad. Sci. USA, vol. 100: p. 4712-17.
Hodi and Dranoff, 2006, "Combinatorial cancer immunotherapy," Adv. Immunol., vol. 90: p. 341-68.
Huang, Z., "Structural chemistry and therapeutic intervention of protein-portein interactions in immune response, human immunodeficiency virus entry, and apoptosis", Pharmacology and Therapeutics, 2000, 86: 201-215.

(56) References Cited

OTHER PUBLICATIONS

Hurwitz et al., "Combination immunotherapy of primary prostate cancer in a transgenic mouse model using CTLA-4 blockade," *Cancer Res.* (2000);60(9):2444-8.
International Search Report for PCT/US2004/016995, mailed May 10, 2005.
Jaberipour M, et al., "Increased CTLA-4 and FOXP3 Transcripts in Peripheral Blood Mononuclear Cells of Patients with Breast Cancer," Pathol Oncol Res. Mar. 21, 2010. [Epub ahead of print].
Jago et al., 2004, "Differential expression of CTLA-4 among T cell subsets," *Clin. Exp. Immunol.*, vol. 136: p. 463-71.
Jain, R.K., "Barriers to drug delivery in solid tumors", Scientific American, Jul. 1994, pp. 58-65.
Janik et al., "A pilot study of MDX-010 after vaccine failure in patients with advanced malignancy," Blood (2003);102(11):647A, Abstract No. 2391.
Keler et al., 2003, "Activity and safety of CTLA-4 blockade combined with vaccines in Cynomolgus Macaques," *J. Immunol.*, vol. 171: p. 6251-59.
Langer et al., "Updated on anti-CTLA-4 antibodies in clinical trials", *Expert. Opin. Biol. Ther.* 7(8): 1245-1256 (2007).
Lee, K-H, et al., "Increased vaccine-specific T cell frequency after peptide-based vaccination correlates with increased susceptibility to in vitro stimulation but does not lead to tumor regression," Journal of Immunology (1999), vol. 163: 6292-6300.
Macon-Lemaitre and Triebel, 2005, "The negative regulatory function of the lymphocyte-activation gene-3 co-receptor (CD223) on human T cells," *Immunology*, vol. 115: p. 10-178.
Maker et al., "Intrapatient dose escalation of anti-CTLA-4 antibody in patients with metastatic melanoma", *J. Immunother.* 29(4): 864-872 (2007).
Metz, et al., 1998, "Differential role of CTLA-4 in regulation of resting memory versus naive CD4 T cell activation," *J. Immunol.*, vol. 161: p. 5855-61.
Mokyr, et al., 1998, "Realization of the therapeutic potential of CTLA-4 blockade in low-dose chemotherapy-treated tumor-bearing mice," *Cancer Research, American Association for Cancer Research*, vol. 58, No. 23: p. 5301-5304.
Murata, et al. "Expression of the costimulatory molecule BB-1, the ligands CTLA-4 and CD28, and their mRNA in inflammatory myopathies." Am J Pathol. Aug. 1999; vol. 155 (2):453-60.
O'Mahony et al., "A pilot study of CTLA-4 blockade after cancer vaccine failure in patients with advanced malignancy," *Clin Cancer Res.* (2007);13(3):958-964.
Overwijk et al., "Vaccination with a recombinant vaccinia virus encoding a "self" antigen induces autoimmune vitiligo and tumor cell destruction in mice: requirement for CD4(+) T lymphocytes," *Proc Natl Acad Sci U S A.* (1999);96(6):2982-7.
Perrin et al., "CTLA-4 blockade enhances clinical disease and cytokine production during experimental allergic encephalomyelitis," *J Immunol.* (1996);157(4):1333-6.
Phan et al., "Cancer regression and autoimmunity induced by cytotoxic T lymphocyte-associated antigen 4 blockade in patients with metastatic melanoma," *Proc Natl Acad Sci U S A.* (2003);100(14):8372-7.
Ribas et al., 2005, "Role of dendritic cell phenotype, determinant spreading, and negative costimulatory blockade in dendritic cell-based melanoma immunotherapy," *J. Immunother.*, vol. 27: p. 354-67.
Rosenberg, "A new era for cancer immunotherapy based on the genes that encode cancer antigens," *Immunity*, 1999; 10:281-7.
Rosenberg and White, "Vitiligo in patients with melanoma: normal tissue antigens can be targets for cancer immunotherapy," *J Immunother Emphasis Tumor Immunol.* (1996);19(1):81-4.

Rudnick et al., "Affinity and avidity in antibody-based tumor targeting", Can. Biotherp. & Radiopharm. 24: 155-162 (2009).
Sanderson et al., "Autoimmunity in a phase I trial of a fully human anti-cytotoxic T-lymphocyte antigen-4 monoclonal antibody with multiple melanoma peptides and Montanide ISA 51 for patients with resected stages III and IV melanoma," *J Clin Oncol.* (2005);23(4):741-50.
Saenger et al., *Can. Immun.* 8: 1-7 (Jan. 2008).
Shah KV, et al., "CTLA-4 is a direct target of Wnt/beta-catenin signaling and is expressed in human melanoma tumors," J Invest Dermatol. Dec. 2008;128(12):2870-9. Epub Jun. 19, 2008.
Small et al., "A pilot trial of CTLA-4 blockade with human anti-CTLA-4 in patients with hormone-refractory prostate cancer," *Clin. Cancer Res.* (2007);13(6):1810-1815.
Spencer et al., "Distinct inflammatory mechanisms mediate early versus late colitis in mice", *Gastroenterology*, 2002, 122:94-109.
Tarhini & Kirkwood, "Tremelimumab (CP-675,206) a fully human anticytotoxic T lymphocyte-associated antigen 4 monoclonal antibody for treatment of patients with advanced cancers," *Expert Opin. Boil. Ther.* (2008);8(10):1583-1593.
Tassev & Cheung, "Monoclonal antibody therapies for solid tumors," *Expert. Opin. Biol. Ther.* (2009);9(3):341-353.
Thurber et al., "Antibody tumor penetration: transport opposed by systemic and antigen-mediated clearance", Adv. Drug Deliv. Rev. 60: 1421-1434 (2008).
Titelbaum et al., "anti-tumor necrosis factor alpha-associated multiple sclerosis", AJNR Am J Neuroradiol, 26: 1548-1550, Jun./Jul. 2005.
Tivol, et al., 1995, *Immunity*, vol. 3: p. 541-547.
Underhill et al., "Phase I dose escalation trial of tremelimumab (CP-675,206) administered in combination with PF-3512676 in patients with melanoma or other advanced cancers," *J. Clin. Oncol.* (2009);27:15s (Suppl; abstract 3046).
Van Assche et al., *Curr. Opin. Gastroenterol.*, Jul. 2005, 21: 443-447.
van Elsas, et al., 1999, "Combination Immunotherapy of B16 Melanoma Using Anti-Cytoxic T Lymphocyte-associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation," *J. Exp. Med.*, vol. 190: p. 355-366.
Voskoglou-Nomikos et al., "Clinical predictive value of the in vitro cell line, human xenograft, and mouse allograft preclinical cancer models", Clin. Can. res. 9: 4227-4239 (2003).
Weber JS. "Tumor evasion may occur via expression of regulatory molecules: a case for CTLA-4 in melanoma," J Invest Dermatol. Dec. 2008;128(12):2750-2.
Weber, J., "Review: Anti-CTLA-4 Antibody Ipilimumab: Case studies of clinical response and immune-related adverse events", The Oncologist, 12: 864-872 (2007).
Yang et al., "Ipilimumab (anti-CTLA4 antibody) causes regression of metastatic renal cell cancer associated with enteritis and hypophysitis," *J. Immunother.* (2007);30(8):825-830.
Zenapax® package insert and information, 2005.
U.S. Appl. No. 13/335,232, filed Dec. 22, 2011.
Hainsworth, et al., "Rituximab as First-Line and Maintenance Therapy for Patients with Indolent Non-Hodgkin's Lymphona", *Journal of Clinical Oncology.*, 20(20):4261-4267 (2002).
Van Elsas et al., "Elucidating the autoimmune and antitumor effector mechanisms of a treatment based on cytotoxic T lymphocyte antigen-4 blockade in combination with a B16 melanoma vaccine: comparison of prophylaxis and therapy," *J Exp Med.*, 194(4):481-489 (2001).

* cited by examiner

10D1.3 VH (SEQ ID NO: 2)

| | | | | |
|---|---|---|---|---|
| TGGGGGAGGC | GTGGTCCAGC | CTGGGAGGTC | CCTGAGACTC | TCCTGTGCAG | 50
| CCTCTGGATT | CACCTTCAGT | AGCTATACTA | TGCACTGGGT | CCGCCAGGCT | 100
| CCAGGCAAGG | GGCTGGAGTG | GGTGACATTT | ATATCATATG | ATGGAAACAA | 150
| TAAATACTAC | GCAGACTCCG | TGAAGGGCCG | ATTCACCATC | TCCAGAGACA | 200
| ATTCCAAGAA | CACGCTGTAT | CTGCAAATGA | ACAGCCTGAG | AGCTGAGGAC | 250
| ACGGCTATAT | ATTACTGTGC | GAGGACCGGC | TGGCTGGGGC | CCTTTGACTA | 300
| CTGGGGCCAG | GGAACCCTGG | TCACCGTCTC | CTCAGCCTCC | ACCAAGGGC | 349

FIG. 4A

10D1.3 VK (SEQ ID NO: 3)

| | | | | |
|---|---|---|---|---|
| CTCCAGGCAC | CCTGTCTTTG | TCTCCAGGGG | AAAGAGCCAC | CCTCTCCTGC | 50
| AGGGCCAGTC | AGAGTGTTGG | CAGCAGCTAC | TTAGCCTGGT | ACCAGCAGAA | 100
| ACCTGGCCAG | GCTCCCAGGC | TCCTCATCTA | TGGTGCATTC | AGCAGGGCCA | 150
| CTGGCATCCC | AGACAGGTTC | AGTGGCAGTG | GGTCTGGGAC | AGACTTCACT | 200
| CTCACCATCA | GCAGACTGGA | GCCTGAAGAT | TTTGCAGTGT | ATTACTGTCA | 250
| GCAGTATGGT | AGCTCACCGT | GGACGTTCGG | CCAAGGGACC | AAGGTGGAAA | 300
| TCAAACGAAC | TGTGGCTGCA | C | | | 321

FIG. 4B

SEQ ID NOs: 4, 6 & 8 (respectively)

```
VK A-27
Germline: GAA ATT GTG TTG ACG CAG TCT CCA GGC ACC CTG TCT TTG TCT CCA GGG GAA AGA GCC ACC CTC TCC TGC
1OD1:      --- --- --- --- --- --- --- --- --- --- --- --- --- --- --- --- --- --- --- --- --- --- ---
4B6:       --- --- --- --- --- --- --- --- --- --- --- --- --- --- --- --- --- --- --- --- --- --- ---

CDR1
VK A-27:   AGG GCC AGT CAG AGT GTT AGC AGC TAC TTA GCC TGG TAC CAG CAG AAA CCT GGC CAG GCT CCC AGG
1OD1:      --- --- --- --- --- --- -G- --- --- --- --- --- --- --- --- --- --- --- --- --- --- ---
4B6:       --- --- --- --- --- --- --- --- --- -T- --- --- --- --- --- --- --- --- --- --- --- ---

CDR2
VK A-27:   CTC CTC ATC TAT GGT GCA TCC AGC AGG GCC ACT GGC ATC CCA GAC AGG TTC AGT GGC AGT GGG TCT GGG
1OD1:      --- --- --- --- --- --- -T- --- --- --- --- --- --- --- --- --- --- --- --- --- --- --- ---
4B6:       --- --- --- --- --- --- --- --- --- --- --- --- --- --- --- --- --- --- --- --- --- --- ---

CDR3
VK A-27:   ACA GAC TTC ACT CTC ACC ATC AGC AGA CTG GAG CCT GAA GAT TTT GCA GTG TAT TAC TGT
1OD1:      --- --- --- --- --- --- --- --- --- --- --- --- --- --- --- --- --- --- --- ---
4B6:       --- --- --- --- --- --- --- --- --- --- --- --- --- --- --- --- --- --- --- ---

JK1
VK A-27:   CAG CAG TAT GGT AGC TCA CC   --G TGG ACG TTC GGC CAA GGG ACC AAG GTG GAA ATC AAA C/
1OD1:      --- --- --- --- --- --- --   --- --- --- --- --- --- --- --- --- --- --- --- --- ---
4B6:       --- --- --- --- --- --- --   --- --- --- --- --- --- --- --- --- --- --- --- --- ---
```

SEQ ID NOs: 10 & 12 (respectively)

```
VK L-15
Germline: GAC ATC CAG ATG ACC CAG TCT CCA TCC TCA CTG TCT GCA TCT GTA GGA GAC AGA GTC ACC ATC ACT TGT
1E2:      --- --- --- --- --- --- --- --- --- --- --- --- --- --- --- --- --- --- --- --- --- --- ---

CDR1
VK L-15:  CGG GCG AGT CAG AGT ATT AGC AGC AGC TGG TTA GCC TGG TAT CAG CAG AAA CCA GAG AAA GCC CCT AAG TCC
1E2:      --- --- --- --- --- --- --- --- --- --- --- --- --- --- --- --- --- --- --- --- --- --- --- ---

CDR2
VK L-15:  CTG ATC TAT GCT GCA TCC AGT TTG CAA AGT GGG GTC CCA TCA AGG TTC AGC GGC AGT GGA TCT GGG ACA
1E2:      --- --- --- --- --- --- --- --- --- --- --- --- --- --- --- --- --- --- --- --- --- --- ---
```

FIG. 5

```
VK L-15:  GAT TTC ACT CTC ACC ATC AGC AGC CTG CAG CCT GAA GAT TTT GCA ACT TAT TAC TGC CAA CAG TAT AAT
1E2:      --- --- --- --- --- --- --- --- --- --- --- --- --- --- --- --- --- --- --- --- --- ---
                                                                                      ─────CDR3-

──Jκ1──
VK A-27:  AGT TAC CCT CC     -G ACG TTC GGC CAA GGG ACC AAG GTG GAA ATC AAA C/
1E2:      --- --- --- --     --- --- --- --- --- --- --- --- --- --- --- ---
```

FIG. 5A

SEQ ID NOs: 14, 16 & 18 (respectively)

```
VH 3-30.3
Germline: CAG GTG CAG CTG GTG GAG TCT GGG GGA GGC GTG GTC CAG CCT GGG AGG TCC CTG AGA CTC TCC TGT GCA GCC
10D1:     --- --- --- --- --- --- --- --- --- --- --- --- --- --- --- --- --- --- --- --- --- --- ---
4B6:      --- --- --- --- --- --- --- --- --- --- --- --- --- --- --- --- --- --- --- --- --- --- ---

CDR1
VH 3-30.3: TCT GGA TTC ACC TTC AGT AGC TAT GCT ATG CAC TGG GTC CGC CAG GCT CCA GGC AAG GGG CTG GAG TGG GTG
10D1:      --- --- --- --- --- --- --- --- G-T --- --- --- --- --- --- --- --- --- --- --- --- --- ---
4B6:       --- --- --- --- --- --- --- --- A-- --- --- --- --- --- --- --- --- --- --- --- --- --- ---
                                             CDR2
VH 3-30.3: GCA GTT ATA TCA TAT GAT GGA AGC AAT AAA TAC TAC GCA GAC TCC GTG AAG GGC CGA TTC ACC ATC TCC AGA
10D1:      --- A-- T-- --- --- --- --- --- --- --- --- --- --- --- --- --- --- G-- --- --- --- --- ---
4B6:       --- A-- T-- --- --- --- --- --- --- --- --- --- --- --- --- --- --- --- --- --- --- --- ---

VH 3-30.3: GAC AAT TCC AAG AAC ACG CTG TAT CTG CAA ATG AAC AGC CTG AGA GCT GAG GAC ACG GCT GTG TAT TAC TGT
10D1:      --- --- --- --- --- --- --- --- --- --- --- --- --- --- --- --- --- --- --- --- A-A --- ---
4B6:       --- --- --- --- --- --- --- --- --- C-- --- --- --- --- --- --- --- --- --- --- A-A --- ---
                                                                   CDR3
                                                                   D7-27              JE4b
VH 3-30.3: GCG AGA                                         ACC GGC TGG CTG GGG CCC TTT GAC TAC TGG GGC CAG GGA ACC CTG GTC ACC GTC TCC TCA G/
10D1:      --- ---  ---G --- --- --- --- --- --- --- --- --- --- --- --- --- --- --- --- --- --- --- --- --- --- --- --- --- ---  ---
4B6:       --- ---  ---G --- --- --- --- --- --- --- --- --- --- --- --- --- --- --- --- --- --- --- --- --- --- --- --- --- ---  -/
```

SEQ ID NOs: 20 & 22 (respectively)

```
VH 3-33
Germline: CAG GTG CAG CTG GTG GAG TCT GGG GGA GGC GTG GTC CAG CCT GGG AGG TCC CTG AGA CTC TCC TGT GCA GCG
1E2:      --- --- --- --- --- --- --- --- --- --- --- --- --- --- --- --- --- --- --- --- --- --- ---
                                              CDR1
VH 3-33: TCT GGA TTC ACC TTC AGT AGC TAT GGC ATG CAC TGG GTC CGC CAG GCT CCA GGC AAG GGG CTG GAG TGG GTG
1E2:     --- --- --- --- --- --- --- --- A-- --- --- --- --- --- --- --- --- --- --- --- --- --- ---
                                             CDR2
VH 3-33: GCA GTT ATA TGG TAT GAT GGA AGT AAT AAA TAC TAT GCA GAC TCC GTG AAG GGC CGA TTC ACC ATC TCC AGA
1E2:     --- --- --- --- --- --- --- --- --- --- --- --- --- --- --- --- --- --- --- --- --- --- ---
```

FIG. 6

```
VH 3-33:    GAC AAT TCC AAG AAC ACG CTG TAT CTG CAA ATG AAC AGC CTG AGA GCC GAG GAC ACG GCT GTG TAT TAC TGT
1E2:        --- --- --- --- --- --- --- --- --- --- --- --- --- --- --- --- --- --- --- --- -T- --- --- ---
                                                       CDR3
                                                                  J_H 3b
VH 3-30.3:  GCG AGA GA                                    
1E2:        --- --- -CT CCC AAT TAT ATT GGT GCT TTT GAT GTC TGG GGC CAA GGG ACA ATG GTC ACC GTC TCT TCA G/
```

FIG. 6A

SEQ ID NOs: 5, 7 & 9 (respectively)

```
                                    CDR1                                    CDR2
VK A-27                                                                     GASSRAT
Germline:  EIVLTQSPGTLSLSPGERATLSC  RASQSVSSSYLA  WYQQKPGQAPRLLIY           --------
10D1:      -----------------------  -----G------  ---------------           ---F---
4B6:       -----------------------  ------F-----  ---------------           -------

CDR3
VK A-27:                                          QQYGSS
Germline:  GIPDRFSGSGSGTDFTLTISRLEPEDFAVYYC       ------PWT  FGQGTKVEIK
10D1:      --------------------------------       ---------  ----------
4B6:       --------------------------------       ---------  ----------
```

SEQ ID NOs: 11 & 13 (respectively)

```
                                    CDR1                                    CDR2
VK L-15                                                                     AASSLQS
Germline:  DIQMTQSPSSLSASVGDRVTITC  RASQGISSWLA   WYQQKPEKAPKSLIY            -------
1E2:       -----------------------  -----------   ---------------            -------

CDR3
VK L-15:                                          QQYNSY
Germline:  GVPSRFSGSGSGTDFTLTISSLQPEDFATYYC       ------PPT  FGQGTKVEIK
1E2:       --------------------------------       ---------  ----------
```

FIG. 7

SEQ ID NOs: 15, 17 & 19 (respectively)

```
                              CDR1                        CDR2
VH 3-30.3
Germline: QVQLVESGGGVVQPGRSLRLSCAAGFTFS SYAMH WVRQAPGKGLEWVA VISYDGSNKYYADSVKG
10D1:     ------------------------------ -T--- -------------- ----F-N----------
4B6:      ------------------------------ -T--- -------------T ----F----H-------

CDR3
VH 3-30.3
Germline: RFTISRDNSKNTLYLQMNSLRAEDTAVYYCAR ──────── TGWLGPFDY WGQGTLVTVSS
10D1:     -------------------------------- [------] --------- -----------
4B6:      --------------V----------------- [------] --------- -----------
```

SEQ ID NOs: 21 & 23 (respectively)

```
                              CDR1                        CDR2
VH 3-33
Germline: QVQLVESGGGVVQPGRSLRLSCAASGFTFS SYGMH WVRQAPGKGLEWVA VIWYDGSNKYYADSVKG
1E2:      ------------------------------ ----- -------------- -----------------

CDR3
VH 3-33
Germline: RFTISRDNSKNTLYLQMNSLRAEDTAVYYCAR ──────── APNYIGAFDV WGQGTMVTVSS
1E2:      ------------------------F------- [------] ---------- -----------
```

FIG. 8

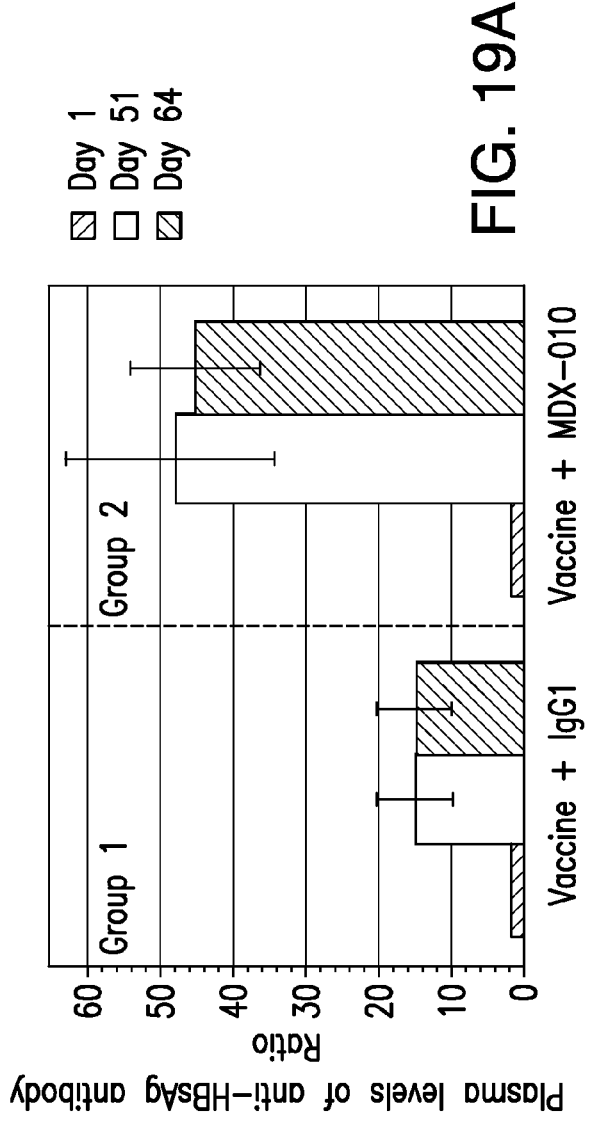
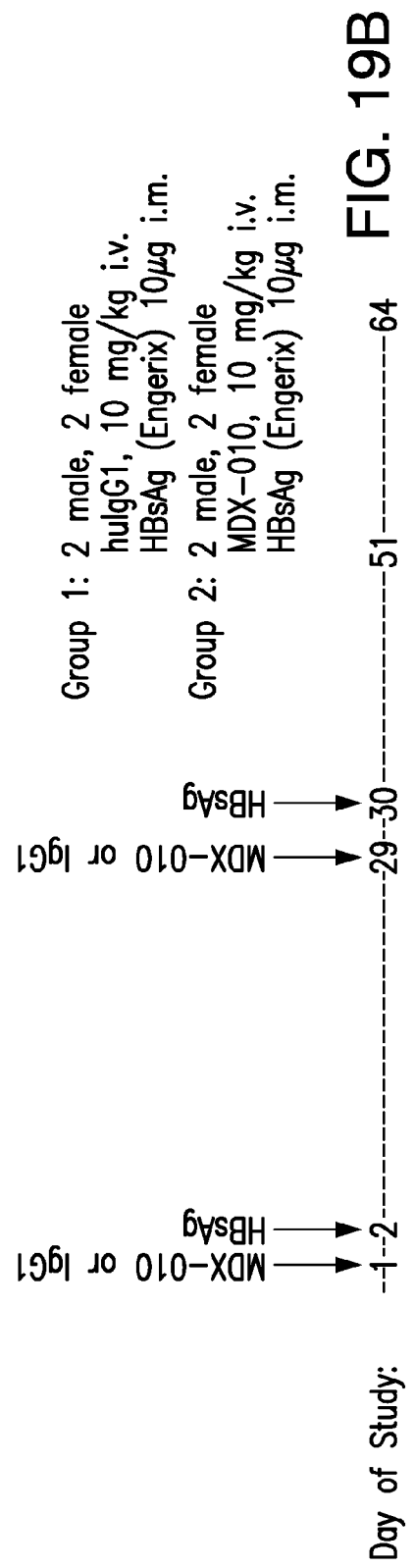

SEQUENCE LISTING

<160> NUMBER OF SEQ ID NOS: 41

<210> SEQ ID NO 1
<211> LENGTH: 3159
<212> TYPE: DNA
<213> ORGANISM: Artificial Sequence
<220> FEATURE:
<223> OTHER INFORMATION: Description of Artificial Sequence:cloning
      vector pGP1k

<400> SEQUENCE: 1

```
aattagcggc cgctgtcgac aagcttcgaa ttcagtatcg atgtggggta cctactgtcc      60
cgggattgcg gatccgcgat gatatcgttg atcctcgagt gcggccgcag tatgcaaaaa     120
aaagcccgct cattaggcgg gctcttggca gaacatatcc atcgcgtccg ccatctccag     180
cagccgcacg cggcgcatct cgggcagcgt tgggtcctgg ccacgggtgc gcatgatcgt     240
gctcctgtcg ttgaggaccc ggctaggctg gcggggttgc cttactggtt agcagaatga     300
atcaccgata cgcgagcgaa cgtgaagcga ctgctgctgc aaaacgtctg cgacctgagc     360
aacaacatga atggtcttcg gtttccgtgt ttcgtaaagt ctggaaacgc ggaagtcagc     420
gccctgcacc attatgttcc ggatctgcat cgcaggatgc tgctggctac cctgtggaac     480
acctacatct gtattaacga agcgctggca ttgaccctga gtgatttttc tctggtcccg     540
ccgcatccat accgccagtt gtttacccte acaacgttcc agtaaccggg catgttcatc     600
atcagtaacc cgtatcgtga gcatcctctc tcgtttcatc ggtatcatta cccccatgaa     660
cagaaattcc cccttacacg gaggcatcaa gtgaccaaac aggaaaaaac cgcccttaac     720
atggcccgct ttatcagaag ccagacatta acgcttctgg agaaactcaa cgagctggac     780
gcggatgaac aggcagacat ctgtgaatcg cttcacgacc acgctgatga gctttaccgc     840
agctgcctcg cgcgtttcgg tgatgacggt gaaaacctct gacacatgca gctcccggag     900
acggtcacag cttgtctgta agcggatgcc gggagcagac aagcccgtca gggcgcgtca     960
gcgggtgttg gcgggtgtcg gggcgcagcc atgacccagt cacgtagcga tagcggagtg    1020
tatactggct taactatgcg gcatcagagc agattgtact gagagtgcac catatgcggt    1080
gtgaaatacc gcacagatgc gtaaggagaa ataccgcat caggcgctct tccgcttcct    1140
cgctcactga ctcgctgcgc tcggtcgttc ggctgcggcg agcggtatca gctcactcaa    1200
aggcggtaat acggttatcc acagaatcag gggataacgc aggaaagaac atgtgagcaa    1260
aaggccagca aaaggccagg aaccgtaaaa aggccgcgtt gctggcgttt ttccataggc    1320
```

```
tccgcccccc tgacgagcat cacaaaaatc gacgctcaag tcagaggtgg cgaaacccga   1380
caggactata aagataccag gcgtttcccc ctggaagctc cctcgtgcgc tctcctgttc   1440
cgaccctgcc gcttaccgga tacctgtccg ccttcctccc ttcgggaagc gtggcgcttt   1500
ctcatagctc acgctgtagg tatctcagtt cggtgtaggt cgttcgctcc aagctgggct   1560
gtgtgcacga accccccgtt cagcccgacc gctgcgcctt atccggtaac tatcgtcttg   1620
agtccaaccc ggtaagacac gacttatcgc cactggcagc agccaggcgc gccttggcct   1680
aagaggccac tggtaacagg attagcagag cgaggtatgt aggcggtgct acagagttct   1740
tgaagtggtg gcctaactac ggctacacta aaggacagtt atttggtatc tgcgctctgc   1800
tgaagccagt taccttcgga aaagagttg gtagctcttg atccggcaaa caaccaccg    1860 ctggtagcgg tggtttttt gtttgcaagc agcagattac gcgcagaaaa aaggatctc    1920 aagaagatcc tttgatcttt tctacggggt ctgacgctca gtggaacgaa aactcacgtt   1980
aagggatttt ggtcatgaga ttatcaaaaa ggatcttcac ctagatcctt ttaaattaaa   2040
aatgaagttt taaatcaatc taagtatat atgagtaaac ttggtctgac agttaccaat    2100
gcttaatcag tgaggcacct atctcagcga tctgtctatt tcgttcatcc atagttgcct   2160 gactcccccgt cgtgtagata actacgatac gggagggctt accatctggc cccagtgctg   2220
caatgatacc gcgagaccca cgctcaccgg ctccagattt atcagcaata aaccagccag   2280
ccggaagggc cgagcgcaga agtggtcctg caactttatc cgcctccatc cagtctatta   2340
attgttgccg ggaagctaga gtaagtagtt cgccagttaa tagtttgcgc aacgttgttg   2400
ccattgctgc aggcatcgtg gtgtcacgct cgtcgtttgg tatggcttca ttcagctccg   2460
gttcccaacg atcaaggcga gttacatgat cccccatgtt gtgcaaaaaa gcggttagct   2520
ccttcggtcc tccgatcgtt gtcagaagta agttggccgc agtgttatca ctcatggtta   2580
tggcagcact gcataattct cttactgtca tgccatccgt aagatgcttt tctgtgactg   2640
gtgagtactc aaccaagtca ttctgagaat agtgtatgcg gcgaccgagt tgctcttgcc   2700
cggcgtcaac acgggataat accgcgccac atagcagaac tttaaaagtg ctcatcattg   2760
gaaaacgttc ttcggggcga aaactctcaa ggatcttacc gctgttgaga tccagttcga   2820
tgtaacccac tcgtgcaccc aactgatctt cagcatcttt tactttcacc agcgtttctg   2880
ggtgagcaaa acaggaagg caaaatgccg caaaaaaggg aataaggcg acacggaaat     2940 gttgaatact catactcttc ctttttcaat attattgaag catttatcag ggttattgtc   3000
tcatgagcgg atacatattt gaatgtattt agaaaaataa acaataggg gttccgcgca    3060 catttccccg aaaagtgcca cctgacgtct aagaaaccat tattatcatg acattaacct   3120
ataaaaatag gcgtatcacg aggccctttc gtcttcaag                          3159
```

<210> SEQ ID NO 2
<211> LENGTH: 349
<212> TYPE: DNA
<213> ORGANISM: Homo sapiens
<220> FEATURE:
<223> OTHER INFORMATION: preliminary sequence for heavy chain fragment
      10D1.3

<400> SEQUENCE: 2

```
tgggggaggc gtggtccagc ctgggaggtc cctgagactc tcctgtgcag cctctggatt    60
caccttcagt agctatacta tgcactgggt ccgccaggct ccaggcaagg gctggagtg    120 ggtgacattt atatcatatg atggaaacaa taaatactac gcagactccg tgaagggccg   180
```
attcaccatc tccagagaca attccaagaa cacgctgtat ctgcaaatga acagcctgag    240
agctgaggac acggctatat attactgtgc gaggaccggc tggctggggc cctttgacta    300
ctggggccag ggaaccctgg tcaccgtctc ctcagcctcc accaagggc               349

<210> SEQ ID NO 3
<211> LENGTH: 321
<212> TYPE: DNA
<213> ORGANISM: Homo sapiens
<220> FEATURE:
<223> OTHER INFORMATION: preliminary sequence for light chain fragment
      10D1.3

<400> SEQUENCE: 3
ctccaggcac cctgtctttg tctccagggg aaagagccac cctctcctgc agggccagtc    60
agagtgttgg cagcagctac ttagcctggt accagcagaa acctggccag gctcccaggc    120
tcctcatcta tggtgcattc agcagggcca ctggcatccc agacaggttc agtggcagtg    180
ggtctgggac agacttcact ctcaccatca gcagactgga gcctgaagat tttgcagtgt    240
attactgtca gcagtatggt agctcaccgt ggacgttcgg ccaagggacc aaggtggaaa    300
tcaaacgaac tgtggctgca c                                             321

<210> SEQ ID NO 4
<211> LENGTH: 287
<212> TYPE: DNA
<213> ORGANISM: Homo sapiens
<220> FEATURE:
<223> OTHER INFORMATION: Vk A-27 germline sequence

<400> SEQUENCE: 4
gaaattgtgt tgacgcagtc tccaggcacc ctgtctttgt ctccagggga aagagccacc    60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacc                 287

<210> SEQ ID NO 5
<211> LENGTH: 95
<212> TYPE: PRT
<213> ORGANISM: Homo sapiens
<220> FEATURE:
<223> OTHER INFORMATION: light chain variable region predicted sequence
      for Vk A-27 germline

<400> SEQUENCE: 5

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser
                 85                  90                  95

<210> SEQ ID NO 6
<211> LENGTH: 325
<212> TYPE: DNA
<213> ORGANISM: Homo sapiens
<220> FEATURE:
<223> OTHER INFORMATION: light chain variable region (Vk), 10D1 from Vk
      A-27

<400> SEQUENCE: 6

```
gaaattgtgt tgacgcagtc tccaggcacc ctgtctttgt ctccagggga aagagccacc      60
ctctcctgca gggccagtca gagtgttggc agcagctact tagcctggta ccagcagaaa     120
cctggccagg ctcccaggct cctcatctat ggtgcattca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgtg acgttcggc      300 caagggacca aggtggaaat caaac                                           325
```

<210> SEQ ID NO 7
<211> LENGTH: 108
<212> TYPE: PRT
<213> ORGANISM: Homo sapiens
<220> FEATURE:
<223> OTHER INFORMATION: light chain variagle region predicted sequence
      for 10D1 from Vk A-27

<400> SEQUENCE: 7

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Gly Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Phe Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105

<210> SEQ ID NO 8
<211> LENGTH: 325
<212> TYPE: DNA
<213> ORGANISM: Homo sapiens
<220> FEATURE:
<223> OTHER INFORMATION: light chain variable region (Vk) 4B6 from Vk A-
      27

<400> SEQUENCE: 8

```
gaaattgtgt tgacgcagtc tccaggcacc ctgtctttgt ctccagggga aagagccacc      60
ctctcctgca gggccagtca gagtgttagc agcagcttct agcctggta ccagcagaaa     120 cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgtg acgttcggc      300 caagggacca aggtggaaat caaac                                           325
```

<210> SEQ ID NO 9
<211> LENGTH: 108
<212> TYPE: PRT
<213> ORGANISM: Homo sapiens
<220> FEATURE:
<223> OTHER INFORMATION: light chain variable region predicted sequence for 4B6 from Vk A-27

<400> SEQUENCE: 9

```
Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Ser
             20                  25                  30
Phe Leu Ala Trp Tyr Gln Gln Lys Pro Gly Gln Ala Pro Arg Leu Leu
         35                  40                  45
Ile Tyr Gly Ala Ser Ser Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Trp Thr Phe Gly Gln Gly Thr Lys Val Glu Ile Lys
            100                 105
```

<210> SEQ ID NO 10
<211> LENGTH: 287
<212> TYPE: DNA
<213> ORGANISM: Homo sapiens
<220> FEATURE:
<223> OTHER INFORMATION: Vk L-15 germline sequence

<400> SEQUENCE: 10

```
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat tcactctca ccatcagcag cctgcagcct     240
gaagattttg caacttatta ctgccaacag tataatagtt accctcc                   287
```

<210> SEQ ID NO 11
<211> LENGTH: 94
<212> TYPE: PRT
<213> ORGANISM: Homo sapiens
<220> FEATURE:
<223> OTHER INFORMATION: light chain variable region predicted sequence for Vk L-15 germline

<400> SEQUENCE: 11

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Gly Ile Ser Ser Trp
             20                  25                  30
Leu Ala Trp Tyr Gln Gln Lys Pro Glu Lys Ala Pro Lys Ser Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Asn Ser Tyr
                 85                  90
```

<210> SEQ ID NO 12
<211> LENGTH: 322
<212> TYPE: DNA
<213> ORGANISM: Homo sapiens
<220> FEATURE:
<223> OTHER INFORMATION: light chain variable region Vk 1E2 from Vk L-15

<400> SEQUENCE: 12

```
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt accctccgac gttcggccaa     300
gggaccaagg tggaaatcaa ac                                              322
```

<210> SEQ ID NO 13
<211> LENGTH: 107
<212> TYPE: PRT
<213> ORGANISM: Homo sapiens
<220> FEATURE:
<223> OTHER INFORMATION: light chain variable region predicted sequence
      for 1E2 from Vk L-15

<400> SEQUENCE: 13

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Pro
                 85                  90                  95

Thr Phe Gly Gln Gly Thr Lys Val Glu Ile Lys
            100                 105
```

<210> SEQ ID NO 14
<211> LENGTH: 294
<212> TYPE: DNA
<213> ORGANISM: Homo sapiens
<220> FEATURE:
<223> OTHER INFORMATION: VH 3-30.3 germline sequence

<400> SEQUENCE: 14

```
caggtgcagc tggtggagtc tgggggaggc gtggtccagc ctgggaggtc cctgagactc      60
tcctgtgcag cctctggatt caccttcagt agctatgcta tgcactgggt ccgccaggct     120
ccaggcaagg ggctggagtg ggtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggctgtgt attactgtgc gaga          294
```

<210> SEQ ID NO 15
<211> LENGTH: 98
<212> TYPE: PRT
<213> ORGANISM: Homo sapiens
<220> FEATURE:
<223> OTHER INFORMATION: heavy chain variable region predicted sequence
      for VH 3-30.3 germline

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 16
<211> LENGTH: 355
<212> TYPE: DNA
<213> ORGANISM: Homo sapiens
<220> FEATURE:
<223> OTHER INFORMATION: heavy chain variable region VH 10D1 from VH 3-
      30.3

<400> SEQUENCE: 16
caggtgcagc tggtggagtc tgggggaggc gtggtccagc ctgggaggtc cctgagactc       60
tcctgtgcag cctctggatt caccttcagt agctatacta tgcactgggt ccgccaggct     120
ccaggcaagg ggctggagtg ggtgacattt atatcatatg atggaaacaa taaatactac     180
gcagactccg tgaagggccg attcaccatc tccagagaca attccaagaa cacgctgtat     240
ctgcaaatga acagcctgag agctgaggac acggctatat attactgtgc gaggaccggc     300
tggctggggc cctttgacta ctggggccag ggaaccctgg tcaccgtctc ctcag          355

<210> SEQ ID NO 17
<211> LENGTH: 118
<212> TYPE: PRT
<213> ORGANISM: Homo sapiens
<220> FEATURE:
<223> OTHER INFORMATION: heavy chain variable region predicted sequence
      for 10D1 from VH 3-30.3

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

```
Ala Arg Thr Gly Trp Leu Gly Pro Phe Asp Tyr Trp Gly Gln Gly Thr
            100                 105                 110
Leu Val Thr Val Ser Ser
        115

<210> SEQ ID NO 18
<211> LENGTH: 355
<212> TYPE: DNA
<213> ORGANISM: Homo sapiens
<220> FEATURE:
<223> OTHER INFORMATION: heavy chain variable region VH 4B6 from VH 3-
      30.3

<400> SEQUENCE: 18
caggtgcagc tggtggagtc tgggggaggc gtggtccagc ctggagggtc cctgagactc      60
tcctgtgcag cctctggatt caccttcagt agctatacta tgcactgggt ccgccaggct     120
ccaggcaagg ggctggagtg ggtgacattt atatcatatg atggaagcaa taaacactac     180
gcagactccg tgaagggccg attcaccgtc tccagagaca attccaagaa cacgctgtat     240
ctgcaaatga acagcctgag agctgaggac acggctatat attactgtgc gaggaccggc     300
tggctggggc cctttgacta ctggggccag ggaaccctgg tcaccgtctc ctcag          355

<210> SEQ ID NO 19
<211> LENGTH: 118
<212> TYPE: PRT
<213> ORGANISM: Homo sapiens
<220> FEATURE:
<223> OTHER INFORMATION: heavy chain variable region predicted sequence
      for 4B6 from VH 3-30.3

<400> SEQUENCE: 19

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Thr Met His Trp Val Arg Gln Ala Pro Gly Lys Gly Leu Glu Trp Val
         35                  40                  45

Thr Phe Ile Ser Tyr Asp Gly Ser Asn Lys His Tyr Ala Asp Ser Val
     50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 20
<211> LENGTH: 296
<212> TYPE: DNA
<213> ORGANISM: Homo sapiens
<220> FEATURE:
<223> OTHER INFORMATION: VH 3-33 germline sequence

<400> SEQUENCE: 20
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
```

```
gcagactccg tgaagggccg attcaccatc tccagagaca attccaagaa cacgctgtat    240
ctgcaaatga acagcctgag agccgaggac acggctgtgt attactgtgc gagaga        296
```

<210> SEQ ID NO 21
<211> LENGTH: 98
<212> TYPE: PRT
<213> ORGANISM: Homo sapiens
<220> FEATURE:
<223> OTHER INFORMATION: heavy chain variable region predicted sequence
      for VH 3-33 germline

<400> SEQUENCE: 21

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 22
<211> LENGTH: 358
<212> TYPE: DNA
<213> ORGANISM: Homo sapiens
<220> FEATURE:
<223> OTHER INFORMATION: heavy chain variable region VH 1E2 from VH 3-33

<400> SEQUENCE: 22

```
caggtgcagc tggtggagtc tgggggaggc gtggtccagc ctggaggtc cctgagactc     60 tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt tttactgtgc gagagctccc   300
aattatattg gtgctttga tgtctggggc caagggacaa tggtcaccgt ctcttcag     358
```

<210> SEQ ID NO 23
<211> LENGTH: 119
<212> TYPE: PRT
<213> ORGANISM: Homo sapiens
<220> FEATURE:
<223> OTHER INFORMATION: heavy chain variable region predicted sequence
      for 1E2 from VH 3-33

<400> SEQUENCE: 23

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Phe Tyr Cys
                 85                  90                  95

Ala Arg Ala Pro Asn Tyr Ile Gly Ala Phe Asp Val Trp Gly Gln Gly
            100                 105                 110

Thr Met Val Thr Val Ser Ser
        115

<210> SEQ ID NO 24
<211> LENGTH: 12
<212> TYPE: PRT
<213> ORGANISM: Homo sapiens
<220> FEATURE:
<223> OTHER INFORMATION: light chain CDR1 (HuMab 10D1)

<400> SEQUENCE: 24

Arg Ala Ser Gln Ser Val Gly Ser Ser Tyr Leu Ala
 1               5                  10

<210> SEQ ID NO 25
<211> LENGTH: 12
<212> TYPE: PRT
<213> ORGANISM: Homo sapiens
<220> FEATURE:
<223> OTHER INFORMATION: light chain CDR1 (HuMab 4B6)

<400> SEQUENCE: 25

Arg Ala Ser Gln Ser Val Ser Ser Ser Phe Leu Ala
 1               5                  10

<210> SEQ ID NO 26
<211> LENGTH: 11
<212> TYPE: PRT
<213> ORGANISM: Homo sapiens
<220> FEATURE:
<223> OTHER INFORMATION: light chain CDR1 (HuMab 1E2)

<400> SEQUENCE: 26

Arg Ala Ser Gln Gly Ile Ser Ser Trp Leu Ala
 1               5                  10

<210> SEQ ID NO 27
<211> LENGTH: 5
<212> TYPE: PRT
<213> ORGANISM: Homo sapiens
<220> FEATURE:
<223> OTHER INFORMATION: heavy chain CDR1 (HuMab 10D1, 4B6)

<400> SEQUENCE: 27

Ser Tyr Thr Met His
 1               5

<210> SEQ ID NO 28
<211> LENGTH: 5
<212> TYPE: PRT
<213> ORGANISM: Homo sapiens
<220> FEATURE:
<223> OTHER INFORMATION: heavy chain CDR1 (HuMab 1E2)

<400> SEQUENCE: 28

Ser Tyr Gly Met His
 1               5
```

<210> SEQ ID NO 29
<211> LENGTH: 7
<212> TYPE: PRT
<213> ORGANISM: Homo sapiens
<220> FEATURE:
<223> OTHER INFORMATION: light chain CDR2 (HuMab 10D1)

<400> SEQUENCE: 29

Gly Ala Phe Ser Arg Ala Thr
 1               5

<210> SEQ ID NO 30
<211> LENGTH: 7
<212> TYPE: PRT
<213> ORGANISM: Homo sapiens
<220> FEATURE:
<223> OTHER INFORMATION: light chain CDR2 (HuMab 4B6)

<400> SEQUENCE: 30

Gly Ala Ser Ser Arg Ala Thr
 1               5

<210> SEQ ID NO 31
<211> LENGTH: 7
<212> TYPE: PRT
<213> ORGANISM: Homo sapiens
<220> FEATURE:
<223> OTHER INFORMATION: light chain CDR2 (HuMab 1E2)

<400> SEQUENCE: 31

Ala Ala Ser Ser Leu Gln Ser
 1               5

<210> SEQ ID NO 32
<211> LENGTH: 17
<212> TYPE: PRT
<213> ORGANISM: Homo sapiens
<220> FEATURE:
<223> OTHER INFORMATION: heavy chain CDR2 (HuMab 10D1)

<400> SEQUENCE: 32

Phe Ile Ser Tyr Asp Gly Asn Asn Lys Tyr Tyr Ala Asp Ser Val Lys
 1               5                  10                  15

Gly

<210> SEQ ID NO 33
<211> LENGTH: 17
<212> TYPE: PRT
<213> ORGANISM: Homo sapiens
<220> FEATURE:
<223> OTHER INFORMATION: heavy chain CDR2 (HuMab 4B6)

<400> SEQUENCE: 33

Phe Ile Ser Tyr Asp Gly Ser Asn Lys His Tyr Ala Asp Ser Val Lys
 1               5                  10                  15

Gly

<210> SEQ ID NO 34
<211> LENGTH: 17
<212> TYPE: PRT
<213> ORGANISM: Homo sapiens
<220> FEATURE:
<223> OTHER INFORMATION: heavy chain CDR2 (HuMab 1E2)

```
<400> SEQUENCE: 34

Val Ile Trp Tyr Asp Gly Ser Asn Lys Tyr Tyr Ala Asp Ser Val Lys
1               5                   10                  15
Gly

<210> SEQ ID NO 35
<211> LENGTH: 9
<212> TYPE: PRT
<213> ORGANISM: Homo sapiens
<220> FEATURE:
<223> OTHER INFORMATION: light chain CDR3 (HuMab 10D1, 4B6)

<400> SEQUENCE: 35

Gln Gln Tyr Gly Ser Ser Pro Trp Thr
1               5

<210> SEQ ID NO 36
<211> LENGTH: 9
<212> TYPE: PRT
<213> ORGANISM: Homo sapiens
<220> FEATURE:
<223> OTHER INFORMATION: light chain CDR3 (HuMab 1E2)

<400> SEQUENCE: 36

Gln Gln Tyr Asn Ser Tyr Pro Pro Thr
1               5

<210> SEQ ID NO 37
<211> LENGTH: 9
<212> TYPE: PRT
<213> ORGANISM: Homo sapiens
<220> FEATURE:
<223> OTHER INFORMATION: heavy chain CDR3 (HuMab 10D1, 4B6)

<400> SEQUENCE: 37

Thr Gly Trp Leu Gly Pro Phe Asp Tyr
1               5

<210> SEQ ID NO 38
<211> LENGTH: 10
<212> TYPE: PRT
<213> ORGANISM: Homo sapiens
<220> FEATURE:
<223> OTHER INFORMATION: heavy chain CDR3 (MuMab 1E2)

<400> SEQUENCE: 38

Ala Pro Asn Tyr Ile Gly Ala Phe Asp Val
1               5                   10

<210> SEQ ID NO 39
<211> LENGTH: 3881
<212> TYPE: DNA
<213> ORGANISM: Artificial Sequence
<220> FEATURE:
<223> OTHER INFORMATION: Description of Artificial Sequence: kappa light
      chain plasmid pCK7-96

<400> SEQUENCE: 39
tcttccgctt cctcgctcac tgactcgctg cgctcggtcg ttcggctgcg gcgagcggta      60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc ccctggaag ctccctcgtg     300
```

-continued

| | |
|---|---|
| cgctctcctg ttccgaccct gccgcttacc ggatacctgt ccgcctttct cccttcggga | 360 |
| agcgtggcgc tttctcatag ctcacgctgt aggtatctca gttcggtgta ggtcgttcgc | 420 |
| tccaagctgg gctgtgtgca cgaaccccc gttcagcccg accgctgcgc cttatccggt | 480 |
| aactatcgtc ttgagtccaa cccggtaaga cacgacttat cgccactggc agcagccact | 540 |
| ggtaacagga ttagcagagc gaggtatgta ggcggtgcta cagagttctt gaagtggtgg | 600 |
| cctaactacg gctacactag aaggacagta tttggtatct gcgctctgct gaagccagtt | 660 |
| accttcggaa aaagagttgg tagctcttga tccggcaaac aaaccaccgc tggtagcggt | 720 |
| ggttttttg tttgcaagca gcagattacg cgcagaaaaa aaggatctca agaagatcct | 780 |
| ttgatctttt ctacggggtc tgacgctcag tggaacgaaa actcacgtta agggattttg | 840 |
| gtcatgagat tatcaaaaag gatcttcacc tagatccttt taaattaaaa atgaagtttt | 900 |
| aaatcaatct aaagtatata tgagtaaact tggtctgaca gttaccaatg cttaatcagt | 960 |
| gaggcaccta tctcagcgat ctgtctattt cgttcatcca tagttgcctg actccccgtc | 1020 |
| gtgtagataa ctacgatacg ggagggctta ccatctggcc ccagtgctgc aatgataccg | 1080 |
| cgagacccac gctcaccggc tccagattta tcagcaataa accagccagc cggaagggcc | 1140 |
| gagcgcagaa gtggtcctgc aactttatcc gcctccatcc agtctattaa ttgttgccgg | 1200 |
| gaagctagag taagtagttc gccagttaat agtttgcgca acgttgttgc cattgctaca | 1260 |
| ggcatcgtgg tgtcacgctc gtcgtttggt atggcttcat tcagctccgg ttcccaacga | 1320 |
| tcaaggcgag ttacatgatc ccccatgttg tgcaaaaaag cggttagctc cttcggtcct | 1380 |
| ccgatcgttg tcagaagtaa gttggccgca gtgttatcac tcatggttat ggcagcactg | 1440 |
| cataattctc ttactgtcat gccatccgta agatgctttt ctgtgactgg tgagtactca | 1500 |
| accaagtcat tctgagaata gtgtatgcgg cgaccgagtt gctcttgccc ggcgtcaata | 1560 |
| cgggataata ccgcgccaca tagcagaact ttaaaagtgc tcatcattgg aaaacgttct | 1620 |
| tcggggcgaa aactctcaag gatcttaccg ctgttgagat ccagttcgat gtaacccact | 1680 |
| cgtgcaccca actgatcttc agcatctttt actttcacca gcgtttctgg gtgagcaaaa | 1740 |
| acaggaaggc aaaatgccgc aaaaaaggga ataagggcga cacggaaatg ttgaatactc | 1800 |
| atactcttcc tttttcaata ttattgaagc atttatcagg gttattgtct catgagcgga | 1860 |
| tacatatttg aatgtattta gaaaaataaa caaatagggg ttccgcgcac atttccccga | 1920 |
| aaagtgccac ctgacgtcta agaaaccatt attatcatga cattaaccta taaaaatagg | 1980 |
| cgtatcacga ggccctttcg tctcgcgcgt ttcggtgatg acggtgaaaa cctctgacac | 2040 |
| atgcagctcc cggagacggt cacagcttgt ctgtaagcgg atgccgggag cagacaagcc | 2100 |
| cgtcagggcg cgtcagcggg tgttggcggg tgtcggggct ggcttaacta tgcggcatca | 2160 |
| gagcagattg tactgagagt gcaccatatg cggtgtgaaa taccgcacag atgcgtaagg | 2220 |
| agaaaatacc gcatcaggcg ccattcgcca ttcaggctgc gcaactgttg ggaagggcga | 2280 |
| tcggtgcggg cctcttcgct attacgccag ctggcgaaag gggatgtgc tgcaaggcga | 2340 |
| ttaagttggg taacgccagg gttttcccag tcacgacgtt gtaaaacgac ggccagtgcc | 2400 |
| aagctagcgg ccgcggtcca accaccaatc tcaaagcttg gtaccgggga gcctgttatc | 2460 |
| ccagcacagt cctggaagag gcacagggga ataaaagcg gacggaggct ttccttgact | 2520 |
| cagccgctgc ctggtcttct tcagacctgt tctgaattct aaactctgag ggggtcggat | 2580 |
| gacgtggcca ttctttgcct aaagcattga gtttactgca aggtcagaaa agcatgcaaa | 2640 |
| gccctcagaa tggctgcaaa gagctccaac aaaacaattt agaactttat taaggaatag | 2700 |

-continued

| | |
|---|---|
| ggggaagcta ggaagaaact caaaacatca agattttaaa tacgcttctt ggtctccttg | 2760 |
| ctataattat ctgggataag catgctgttt tctgtctgtc cctaacatgc cctgtgatta | 2820 |
| tccgcaaaca acacacccaa gggcagaact tgttactta aacaccatcc tgtttgcttc | 2880 |
| tttcctcagg aactgtggct gcaccatctg tcttcatctt cccgccatct gatgagcagt | 2940 |
| tgaaatctgg aactgcctct gttgtgtgcc tgctgaataa cttctatccc agagaggcca | 3000 |
| aagtacagtg gaaggtggat aacgccctcc aatcgggtaa ctcccaggag agtgtcacag | 3060 |
| agcaggacag caaggacagc acctacagcc tcagcagcac cctgacgctg agcaaagcag | 3120 |
| actacgagaa acacaaagtc tacgcctgcg aagtcaccca tcagggcctg agctcgcccg | 3180 |
| tcacaaagag cttcaacagg ggagagtgtt agagggagaa gtgcccccac ctgctcctca | 3240 |
| gttccagcct gacccctcc catcctttgg cctctgaccc ttttccaca ggggacctac | 3300 |
| ccctattgcg gtcctccagc tcatctttca cctcaccccc ctcctcctcc ttggctttaa | 3360 |
| ttatgctaat gttggaggag aatgaataaa taaagtgaat cttttgcacct gtggtttctc | 3420 |
| tctttcctca atttaataat tattatctgt tgtttaccaa ctactcaatt tctcttataa | 3480 |
| gggactaaat atgtagtcat cctaaggcgc ataaccattt ataaaaatca tccttcattc | 3540 |
| tattttaccc tatcatcctc tgcaagacag tcctccctca aacccacaag ccttctgtcc | 3600 |
| tcacagtccc ctgggccatg gatcctcaca tcccaatccg cggccgcaat tcgtaatcat | 3660 |
| ggtcatagct gtttcctgtg tgaaattgtt atccgctcac aattccacac aacatacgag | 3720 |
| ccggaagcat aaagtgtaaa gcctggggtg cctaatgagt gagctaactc acattaattg | 3780 |
| cgttgcgctc actgcccgct ttccagtcgg gaaacctgtc gtgccagctg cattaatgaa | 3840 |
| tcggccaacg cgcggggaga ggcggtttgc gtattgggcg c | 3881 |

<210> SEQ ID NO 40
<211> LENGTH: 4723
<212> TYPE: DNA
<213> ORGANISM: Artificial Sequence
<220> FEATURE:
<223> OTHER INFORMATION: Description of Artificial Sequence:gamma1 heavy
      chain plasmid pCG7-96

<400> SEQUENCE: 40

| | |
|---|---|
| gaactcgagc agctgaagct ttctggggca ggccaggcct gaccttggct ttggggcagg | 60 |
| gaggggcta aggtgaggca ggtggcgcca gccaggtgca cacccaatgc ccatgagccc | 120 |
| agacactgga cgctgaacct cgcggacagt taagaaccca ggggcctctg cgccctgggc | 180 |
| ccagctctgt cccacaccgc ggtcacatgg caccacctct cttgcagcct ccaccaaggg | 240 |
| cccatcggtc ttccccctgg cacctcctc caagagcacc tctgggggca gcggccct | 300 |
| gggctgcctg gtcaaggact acttccccga accggtgacg gtgtcgtgga actcaggcgc | 360 |
| cctgaccagc ggcgtgcaca ccttcccggc tgtcctacag tcctcaggac tctactccct | 420 |
| cagcagcgtg gtgaccgtgc cctccagcag cttgggcacc cagacctaca tctgcaacgt | 480 |
| gaatcacaag cccagcaaca ccaaggtgga caagaaagtt ggtgagaggc cagcacaggg | 540 |
| agggagggtg tctgctggaa gccaggctca gcgctcctgc ctggacgcat ccggctatg | 600 |
| cagccccagt ccagggcagc aaggcaggcc ccgtctgcct cttcacccgg aggcctctgc | 660 |
| ccgcccact catgctcagg gagagggtct tctggctttt ccccaggct ctgggcaggc | 720 |
| acaggctagg tgcccctaac ccaggccctg cacacaaagg ggcaggtgct gggctcagac | 780 |
| ctgccaagag ccatatccgg gaggaccctg cccctgacct aagcccaccc caaaggccaa | 840 |

```
actctccact ccctcagctc ggacaccttc tctcctccca gattccagta actcccaatc      900
ttctctctgc agagcccaaa tcttgtgaca aaactcacac atgccaccg tgcccaggta       960 agccagccca ggcctcgccc tccagctcaa ggcgggacag gtgccctaga gtagcctgca    1020
tccagggaca ggccccagcc gggtgctgac acgtccacct ccatctcttc ctcagcacct    1080
gaactcctgg ggggaccgtc agtcttcctc ttcccccaa aacccaagga caccctcatg     1140
atctcccgga cccctgaggt cacatgcgtg gtggtggacg tgagccacga agaccctgag    1200
gtcaagttca actggtacgt ggacggcgtg gaggtgcata atgccaagac aaagccgcgg    1260
gaggagcagt acaacagcac gtaccgtgtg gtcagcgtcc tcaccgtcct gcaccaggac    1320
tggctgaatg gcaaggagta caagtgcaag gtctccaaca aagccctccc agcccccatc    1380
gagaaaacca tctccaaagc caaaggtggg acccgtgggg tgcgagggcc acatggacag    1440
aggccggctc ggcccaccct ctgccctgag agtgaccgct gtaccaacct ctgtccctac    1500
agggcagccc cgagaaccac aggtgtacac cctgccccca tcccgggatg agctgaccaa    1560
gaaccaggtc agcctgacct gcctggtcaa aggcttctat cccagcgaca tcgccgtgga    1620
gtgggagagc aatgggcagc cggagaacaa ctacaagacc acgcctcccg tgctggactc    1680
cgacggctcc ttcttcctct acagcaagct caccgtggac aagagcaggt ggcagcaggg    1740
gaacgtcttc tcatgctccg tgatgcatga ggctctgcac aaccactaca cgcagaagag    1800
cctctccctg tctccgggta aatgagtgcg acggccggca agccccgct ccccgggctc     1860 tcgcggtcgc acgaggatgc ttggcacgta ccccctgtac atacttcccg ggcgcccagc    1920
atggaaataa agcacccagc gctgccctgg gccctgcga gactgtgatg gttctttcca     1980
cgggtcaggc cgagtctgag gcctgagtgg catgagggag gcagagcggg tcccactgtc    2040
cccacactgg cccaggctgt gcaggtgtgc ctgggccccc tagggtgggg ctcagccagg    2100
ggctgccctc ggcagggtgg gggatttgcc agcgtggccc tccctccagc agcacctgcc    2160
ctgggctggg ccacgggaag ccctaggagc ccctggggac agacacacag cccctgcctc    2220
tgtaggagac tgtcctgttc tgtgagcgcc cctgtcctcc cgacctccat gcccactcgg    2280
gggcatgcct gcaggtcgac tctagaggat ccccgggtac cgagctcgaa ttcatcgatg    2340
atatcagatc tgccggtctc cctatagtga gtcgtattaa tttcgataag ccaggttaac    2400
ctgcattaat gaatcggcca acgcgcgggg agaggcggtt tgcgtattgg gcgctcttcc    2460
gcttcctcgc tcactgactc gctgcgctcg gtcgttcggc tgcggcgagc ggtatcagct    2520
cactcaaagg cggtaatacg gttatccaca gaatcagggg ataacgcagg aaagaacatg    2580
tgagcaaaag gccagcaaaa ggccaggaac cgtaaaaagg ccgcgttgct ggcgtttttc    2640
cataggctcc gcccccctga cgagcatcac aaaaatcgac gctcaagtca gaggtggcga    2700
aacccgacag gactataaag ataccaggcg tttccccctg gaagctccct cgtgcgctct    2760
cctgttccga ccctgccgct taccggatac ctgtccgcct ttctcccttc gggaagcgtg    2820
gcgctttctc aatgctcacg ctgtaggtat ctcagttcgg tgtaggtcgt tcgctccaag    2880
ctgggctgtg tgcacgaacc ccccgttcag cccgaccgct gcgccttatc cggtaactat    2940
cgtcttgagt ccaacccggt aagacacgac ttatcgccac tggcagcagc cactggtaac    3000
aggattagca gagcgaggta tgtaggcggt gctacagagt tcttgaagtg gtggcctaac    3060
tacggctaca ctagaaggac agtatttggt atctgcgctc tgctgaagcc agttaccttc    3120
ggaaaaagag ttggtagctc ttgatccggc aaacaaacca ccgctggtag cggtggtttt    3180
tttgtttgca agcagcagat tacgcgcaga aaaaaaggat ctcaagaaga tcctttgatc    3240
```

```
ttttctacgg ggtctgacgc tcagtggaac gaaaactcac gttaagggat tttggtcatg    3300
agattatcaa aaaggatctt cacctagatc cttttaaatt aaaaatgaag ttttaaatca    3360
atctaaagta tatatgagta aacttggtct gacagttacc aatgcttaat cagtgaggca    3420
cctatctcag cgatctgtct atttcgttca tccatagttg cctgactccc cgtcgtgtag    3480
ataactacga tacgggaggg cttaccatct ggccccagtg ctgcaatgat accgcgagac    3540
ccacgctcac cggctccaga tttatcagca ataaaccagc cagccggaag ggccgagcgc    3600
agaagtggtc ctgcaacttt atccgcctcc atccagtcta ttaattgttg ccgggaagct    3660
agagtaagta gttcgccagt taatagtttg cgcaacgttg ttgccattgc tacaggcatc    3720
gtggtgtcac gctcgtcgtt tggtatggct tcattcagct ccggttccca acgatcaagg    3780
cgagttacat gatcccccat gttgtgcaaa aaagcggtta gctccttcgg tcctccgatc    3840
gttgtcagaa gtaagttggc cgcagtgtta tcactcatgg ttatggcagc actgcataat    3900
tctcttactg tcatgccatc cgtaagatgc ttttctgtga ctggtgagta ctcaaccaag    3960
tcattctgag aatagtgtat gcggcgaccg agttgctctt gcccggcgtc aatacgggat    4020
aataccgcgc cacatagcag aactttaaaa gtgctcatca ttggaaaacg ttcttcgggg    4080
cgaaaactct caaggatctt accgctgttg agatccagtt cgatgtaacc cactcgtgca    4140
cccaactgat cttcagcatc ttttactttc accagcgttt ctgggtgagc aaaaacagga    4200
aggcaaaatg ccgcaaaaaa gggaataagg gcgacacgga aatgttgaat actcatactc    4260
ttcctttttc aatattattg aagcatttat cagggttatt gtctcatgag cggatacata    4320
tttgaatgta tttagaaaaa taaacaaata ggggttccgc gcacatttcc ccgaaaagtg    4380
ccacctgacg tctaagaaac cattattatc atgacattaa cctataaaaa taggcgtatc    4440
acgaggccct ttcgtctcgc gcgtttcggt gatgacggtg aaaacctctg acacatgcag    4500
ctcccggaga cggtcacagc ttgtctgtaa gcggatgccg ggagcagaca agcccgtcag    4560
ggcgcgtcag cgggtgttgg cgggtgtcgg ggctggctta actatgcggc atcagagcag    4620
attgtactga gagtgcacca tatggacata ttgtcgttag aacgcggcta caattaatac    4680
ataaccttat gtatcataca catacgattt aggtgacact ata    4723
```

<210> SEQ ID NO 41
<211> LENGTH: 4694
<212> TYPE: DNA
<213> ORGANISM: Artificial Sequence
<220> FEATURE:
<223> OTHER INFORMATION: Description of Artificial Sequence:gamma4 heavy
      chain plasmid pG4HE

<400> SEQUENCE: 41

```
gaactcgagc agctgaagct ttctggggca ggccgggcct gactttggct gggggcaggg      60 aggggctaa ggtgacgcag gtggcgccag ccaggtgcac acccaatgcc catgagccca     120
gacactggac cctgcatgga ccatcgcgga tagacaagaa ccgaggggcc tctgcgccct     180
gggcccagct ctgtcccaca ccgcggtcac atggcaccac ctctcttgca gcttccacca     240
agggcccatc cgtcttcccc ctggcgccct gctccaggag cacctccgag agcacagccg     300
ccctgggctg cctggtcaag gactacttcc ccgaaccggt gacggtgtcg tggaactcag     360
gcgccctgac cagcggcgtg cacaccttcc cggctgtcct acagtcctca ggactctact     420
ccctcagcag cgtggtgacc gtgccctcca gcagcttggg cacgaagacc tacacctgca     480
acgtagatca caagcccagc aacaccaagg tggacaagag agttggtgag aggccagcac     540
```

```
agggagggag ggtgtctgct ggaagccagg ctcagccctc ctgcctggac gcaccccggc    600
tgtgcagccc cagcccaggg cagcaaggca tgccccatct gtctcctcac ccggaggcct    660
ctgaccaccc cactcatgct cagggagagg gtcttctgga ttttccacc aggctccggg     720
cagccacagg ctggatgccc ctaccccagg ccctgcgcat acaggggcag gtgctgcgct    780
cagacctgcc aagagccata tccgggagga ccctgcccct gacctaagcc caccccaaag    840
gccaaactct ccactccctc agctcagaca ccttctctcc tcccagatct gagtaactcc    900
caatcttctc tctgcagagt ccaaatatgg tccccatgc ccatcatgcc caggtaagcc     960
aacccaggcc tcgccctcca gctcaaggcg ggacaggtgc cctagagtag cctgcatcca   1020
gggacaggcc ccagccgggt gctgacgcat ccacctccat ctcttcctca gcacctgagt   1080
tcctgggggg accatcagtc ttcctgttcc cccaaaacc caaggacact ctcatgatct    1140
cccggacccc tgaggtcacg tgcgtggtgg tggacgtgag ccaggaagac cccgaggtcc   1200
agttcaactg gtacgtggat ggcgtggagg tgcataatgc caagacaaag ccgcgggagg   1260
agcagttcaa cagcacgtac cgtgtggtca gcgtcctcac cgtcctgcac caggactggc   1320
tgaacggcaa ggagtacaag tgcaaggtct ccaacaaagg cctcccgtcc tccatcgaga   1380
aaaccatctc caaagccaaa ggtgggaccc acggggtgcg agggccacat ggacagaggt   1440
cagctcggcc caccctctgc cctgggagtg accgctgtgc caacctctgt ccctacaggg   1500
cagccccgag agccacaggt gtacaccctg ccccatccc aggaggagat gaccaagaac    1560
caggtcagcc tgacctgcct ggtcaaaggc ttctaccca gcgacatcgc cgtggagtgg    1620
gagagcaatg ggcagccgga gaacaactac aagaccacgc ctcccgtgct ggactccgac   1680
ggctccttct cctctacag caggctaacc gtggacaaga gcaggtggca ggaggggaat    1740
gtcttctcat gctccgtgat gcatgaggct ctgcacaacc actacacaca gaagagcctc   1800
tccctgtctc tgggtaaatg agtgccaggg ccggcaagcc ccgctcccc gggctctcgg    1860
ggtcgcgcga ggatgcttgg cacgtacccc gtctacatac ttcccaggca cccagcatgg   1920
aaataaagca cccaccactg ccctgggccc ctgtgagact gtgatggttc tttccacggg   1980
tcaggccgag tctgaggcct gagtgacatg agggaggcag agcgggtccc actgtcccca   2040
cactggccca ggctgtgcag gtgtgcctgg gccacctagg gtgggctca gccaggggct    2100
gccctcggca gggtgggga tttgccagcg tggccctccc tccagcagca gctgccctgg    2160
gctgggccac gggaagccct aggagcccct ggggacagac acacagcccc tgcctctgta   2220
ggagactgtc ctgtcctgtg agcgcccgt cctccgaccc ccatgccca ctcgggggga    2280
tccccgggta ccgagctcga attcatcgat gatatcagat ctgccggtct ccctatagtg   2340
agtcgtatta atttcgataa gccaggttaa cctgcattaa tgaatcggcc aacgcgcggg   2400
gagaggcggt ttgcgtattg ggcgctcttc cgcttcctcg ctcactgact cgctgcgctc   2460
ggtcgttcgg ctgcggcgag cggtatcagc tcactcaaag gcggtaatac ggttatccac   2520
agaatcaggg gataacgcag gaaagaacat gtgagcaaaa ggccagcaaa aggccaggaa   2580
ccgtaaaaag gccgcgttgc tggcgttttt ccataggctc cgcccccctg acgagcatca   2640
caaaaatcga cgctcaagtc agaggtggcg aaacccgaca ggactataaa gataccaggc   2700
gtttccccct ggaagctccc tcgtgcgctc tcctgttccg accctgccgc ttaccggata   2760
cctgtccgcc tttctccctt cgggaagcgt ggcgctttct caatgctcac gctgtaggta   2820
tctcagttcg gtgtaggtcg ttcgctccaa gctgggctgt gtgcacgaac cccccgttca   2880
gcccgaccgc tgcgccttat ccggtaacta tcgtcttgag tccaacccgg taagacacga   2940
```

-continued

```
cttatcgcca ctggcagcag ccactggtaa caggattagc agagcgaggt atgtaggcgg    3000
tgctacagag ttcttgaagt ggtggcctaa ctacggctac actagaagga cagtatttgg    3060
tatctgcgct ctgctgaagc cagttacctt cggaaaaaga gttggtagct cttgatccgg    3120
caaacaaacc accgctggta gcggtggttt ttttgtttgc aagcagcaga ttacgcgcag    3180
aaaaaaagga tctcaagaag atcctttgat cttttctacg gggtctgacg ctcagtggaa    3240
cgaaaactca cgttaaggga ttttggtcat gagattatca aaaaggatct tcacctagat    3300
ccttttaaat taaaaatgaa gttttaaatc aatctaaagt atatatgagt aaacttggtc    3360
tgacagttac caatgcttaa tcagtgaggc acctatctca gcgatctgtc tatttcgttc    3420
atccatagtt gcctgactcc ccgtcgtgta gataactacg atacgggagg gcttaccatc    3480
tggccccagt gctgcaatga taccgcgaga cccacgctca ccggctccag atttatcagc    3540
aataaaccag ccagccggaa gggccgagcg cagaagtggt cctgcaactt tatccgcctc    3600
catccagtct attaattgtt gccgggaagc tagagtaagt agttcgccag ttaatagttt    3660
gcgcaacgtt gttgccattg ctacaggcat cgtggtgtca cgctcgtcgt ttggtatggc    3720
ttcattcagc tccggttccc aacgatcaag gcgagttaca tgatccccca tgttgtgcaa    3780
aaaagcggtt agctccttcg gtcctccgat cgttgtcaga agtaagttgg ccgcagtgtt    3840
atcactcatg gttatggcag cactgcataa ttctcttact gtcatgccat ccgtaagatg    3900
cttttctgtg actggtgagt actcaaccaa gtcattctga gaatagtgta tgcggcgacc    3960
gagttgctct tgcccggcgt caatacggga taataccgcg ccacatagca gaactttaaa    4020
agtgctcatc attggaaaac gttcttcggg gcgaaaactc tcaaggatct taccgctgtt    4080
gagatccagt tcgatgtaac ccactcgtgc acccaactga tcttcagcat cttttacttt    4140
caccagcgtt tctgggtgag caaaaacagg aaggcaaaat gccgcaaaaa agggaataag    4200
ggcgacacgg aaatgttgaa tactcatact cttcctttt caatattatt gaagcattta    4260
tcagggttat tgtctcatga gcggatacat atttgaatgt atttagaaaa ataaacaaat    4320
aggggttccg cgcacatttc cccgaaaagt gccacctgac gtctaagaaa ccattattat    4380
catgacatta acctataaaa ataggcgtat cacgaggccc tttcgtctcg cgcgtttcgg    4440
tgatgacggt gaaaacctct gacacatgca gctcccggag acggtcacag cttgtctgta    4500
agcggatgcc gggagcagac aagcccgtca gggcgcgtca gcgggtgttg gcgggtgtcg    4560
gggctggctt aactatgcgg catcagagca gattgtactg agagtgcacc atatggacat    4620
attgtcgtta gaacgcggct acaattaata cataaccta tgtatcatac acatacgatt    4680
taggtgacac tata                                                      4694
```

HUMAN CTLA-4 ANTIBODIES AND THEIR USES

REFERENCE TO RELATED APPLICATIONS

This application is a continuation of U.S. patent application Ser. No. 13/198,263, filed Aug. 4, 2011, issued as U.S. Pat. No. 8,318,916, which is a divisional of U.S. patent application Ser. No. 12/564,756, filed Sep. 22, 2009, issued as U.S. Pat. No. 8,017,114, which is a continuation of U.S. patent application Ser. No. 09/948,939, filed Sep. 7, 2001, issued as U.S. Pat. No. 7,605,238, which is a continuation-in-part of U.S. patent application Ser. No. 09/644,668, filed Aug. 24, 2000, issued as U.S. Pat. No. 6,984,720, which claims the priority to U.S. provisional patent application Ser. No. 60/150,452, filed Aug. 24, 1999, the contents of all of which are hereby incorporated by reference.

SEQUENCE LISTING

The specification further incorporates by references the Sequence Listing submitted via EFS on Feb. 5, 2013. The Sequence Listing text file, identified as 0773750957seglist-.txt, is 43,293 bytes and was created on Oct. 11, 2012. The Sequence Listing, electronically filed, does not extend beyond the scope of the specification and does not contain new matter.

FIELD OF THE INVENTION

The present invention relates generally to molecular immunology and the treatment of human diseases. In particular, it relates to novel human sequence antibodies against human CTLA-4 and methods of treating human diseases and infections using these antibodies.

BACKGROUND OF THE INVENTION

The vertebrate immune system requires multiple signals to achieve optimal immune activation; see, e.g., Janeway, Cold Spring Harbor Symp. Quant. Biol. 54:1-14 (1989); Paul William. E., ed. Raven Press, N.Y., Fundamental Immunology, 4th edition (1998), particularly chapters 12 and 13, pages 411 to 478. Interactions between T lymphocytes (T cells) and antigen presenting cells (APC) are essential to the immune response. Levels of many cohesive molecules found on T cells and APC's increase during an immune response (Springer et al., A. Rev. Immunol. 5:223-252 (1987); Shaw and Shimuzu, Current Opinion in Immunology, Eds. Kindt and Long, 1:92-97 (1988)); and Hemler, Immunology Today 9:109-113 (1988)). Increased levels of these molecules may help explain why activated APC's are more effective at stimulating antigen-specific T cell proliferation than are resting APC's (Kaiuchi et al., J. Immunol. 131:109-114 (1983); Kreiger et al., J. Immunol. 135:2937-2945 (1985); McKenzie, J. Immunol. 141:2907-2911 (1988); and Hawrylowicz and Unanue, J. Immunol. 141:4083-4088 (1988)).

T cell immune response is a complex process that involves cell-cell interactions (Springer et al., A. Rev. Immunol. 5:223-252 (1987)), particularly between T and accessory cells such as APC's, and production of soluble immune mediators (cytokines or lymphokines) (Dinarello (1987) New Engl. Jour. Med. 317:940-945; Sallusto (1997) J. Exp. Med. 179:1109-1118). This response is regulated by several T-cell surface receptors, including the T-cell receptor complex (Weiss (1986) Ann. Rev. Immunol. 4:593-619) and other "accessory" surface molecules (Allison (1994) Curr. Opin. Immunol. 6:414-419; Springer (1987) supra). Many of these accessory molecules are naturally occurring cell surface differentiation (CD) antigens defined by the reactivity of monoclonal antibodies on the surface of cells (McMichael, Ed., Leukocyte Typing III, Oxford Univ. Press, Oxford, N.Y. (1987)).

Early studies suggested that B lymphocyte activation requires two signals (Bretscher (1970) Science 169:1042-1049) and now it is believed that all lymphocytes require two signals for their optimal activation, an antigen specific or clonal signal, as well as a second, antigen non-specific signal. (Janeway, supra). Freeman (1989) J. Immunol. 143:2714-2722) isolated and sequenced a cDNA clone encoding a B cell activation antigen recognized by MAb B7 (Freeman (1987) J. Immunol. 138:3260). COS cells transfected with this cDNA have been shown to stain by both labeled MAb B7 and MAb BB-1 (Clark (1986) Human Immunol. 16:100-113; Yokochi (1981) J. Immunol. 128:823; Freeman et al., (1989) supra; Freeman et al. (1987), supra). In addition, expression of this antigen has been detected on cells of other lineages, such as monocytes (Freeman et al., supra).

T helper cell (Th) antigenic response requires signals provided by APCs. The first signal is initiated by interaction of the T cell receptor complex (Weiss, J. Clin. Invest. 86:1015 (1990)) with antigen presented in the context of class II major histocompatibility complex (MHC) molecules on the APC (Allen, Immunol. Today 8:270 (1987)). This antigen-specific signal is not sufficient to generate a full response, and in the absence of a second signal may actually lead to clonal inactivation or anergy (Schwartz, Science 248:1349 (1990)), The requirement for a second "costimulatory" signal provided by the MHC has been demonstrated in a number of experimental systems (Schwartz, supra; Weaver and Unanue, Immunol. Today 11:49 (1990)). The molecular nature of this second signal is not completely understood, although it is clear in some cases that both soluble molecules such as interleukin (IL)-1 (Weaver and Unanue, supra) and membrane receptors involved in intercellular adhesion (Springer, Nature 346:425 (1990)) can provide costimulatory signals.

CD28 antigen, a homodimeric glycoprotein of the immunoglobulin superfamily (Aruffo and Seed, Proc. Natl. Acad. Sci. 84:8573-8577 (1987)), is an accessory molecule found on most mature human T cells (Damle et al., J. Immunol. 131:2296-2300 (1983)). Current evidence suggests that this molecule functions in an alternative T cell activation pathway distinct from that initiated by the T-cell receptor complex (June et al., Mol. Cell. Biol. 7:4472-4481 (1987)). Monoclonal antibodies (MAbs) reactive with CD28 antigen can augment T cell responses initiated by various polyclonal stimuli (reviewed by June et al., supra). These stimulatory effects may result from MAb-induced cytokine production (Thompson et al., Proc, Natl. Acad. Sci. 86:1333-1337 (1989); and Lindsten et al., Science 244:339-343 (1989)) as a consequence of increased mRNA stabilization (Lindsten et al. (1989), supra). Anti-CD28 mAbs can also have inhibitory effects, i.e., they can block autologous mixed lymphocyte reactions (Damle et al., Proc. Natl. Acad. Sci. 78:5096-6001 (1981)) and activation of antigen-specific T cell clones (Lesslauer et al., Eur. J. Immunol. 16:1289-1296 (1986)).

Some studies have indicated that CD28 is a counter-receptor for the B cell activation antigen, BBB-1 (Linsley et al., Proc. Natl. Acad. Sci. USA 87:5031-5035 (1990)). The B7/BB-1 antigen is hereafter referred to as the "B7 antigen". The B7 ligands are also members of the immunoglobulin superfamily but have, in contrast to CD28, two Ig domains in their extracellular region, an N-terminal variable (V)-like domain followed by a constant (C)-like domain.

Delivery of a non-specific costimulatory signal to the T cell requires at least two homologous B7 family members found on APC's, B7-1 (also called B7, B7.1, or CD80) and B7-2 (also called B7.2 or CD86), both of which can deliver costimulatory signals to T cells via CD28. Costimulation through CD28 promotes T cell activation.

Using genetic fusions of the extracellular portions of B7 antigen and CD28 receptor, and Immunoglobulin (Ig) C.gamma.1 (constant region heavy chains), interactions between CD28 and B7 antigen have been characterized (Linsley et al., *J. Exp. Med.* 173:721-730 (1991)). Immobilized B7Ig fusion protein, as well as B7 positive CHO cells, have been shown to costimulate T cell proliferation.

T cell stimulation with B7 positive CHO cells also specifically stimulates increased levels of transcripts for IL-2. Additional studies have shown that anti-CD28 MAb inhibited IL-2 production induced in certain T cell leukemia cell lines by cellular interactions with a B cell leukemia line (Kohno et al., Cell. Immunol. 131-1-10 (1990)).

CD28 has a single extracellular variable region (V)-like domain (Aruffo and Seed, supra). A homologous molecule, CTLA-4 has been identified by differential screening of a murine cytolytic-T cell cDNA library (Brunet (1987) *Nature* 328:267-270).

CTLA-4 is a T cell surface molecule that was originally identified by differential screening of a murine cytolytic T cell cDNA library (Brunet et al., *Nature* 328:267-270 (1987)). CTLA-4 is also a member of the immunoglobulin (Ig) superfamily; CTLA-4 comprises a single extracellular Ig domain. CTLA-4 transcripts have been found in T cell populations having cytotoxic activity, suggesting that CTLA-4 might function in the cytolytic response (Brunet et al., supra; Brunet et al., Immunol. Rev. 103-21-36 (1988)). Researchers have reported the cloning and mapping of a gene for the human counterpart of CTLA-4 (Dariavach et al., *Eur. J. Immunol.* 18:1901-1905 (1988)) to the same chromosomal region (2q33-34) as CD28 (Lafage-Pochitaloff et al., *Immunogenetics* 31:198-201 (1990)). Sequence comparison between this human CTLA-4 DNA and that encoding CD28 proteins reveals significant homology of sequence, with the greatest degree of homology in the juxtamembrane and cytoplasmic regions (Brunet et al., 1988, supra; Dariavach et al., 1988, supra).

Some studies have suggested that CTLA-4 has an analogous function as a secondary costimulator (Linsley et al., *J. Exp. Med.* 176:1595-1604 (1992); Wu et al., *J Exp. Med.* 185:1327-1335 (1997) Lindsley, P. et al. U.S. Pat. Nos. 5,977, 318; 5,968,510; 5,885,796; and 5,885,579). However, others have reported that CTLA-4 has an opposing role as a dampener of T cell activation (Krummel (1995) *J. Exp. Med.* 182: 459-465); Krummel et al., *Int'l Immunol.* 8:519-523 (1996); Chambers et al., *Immunity.* 7:885-895 (1997)). It has been reported that CTLA-4 deficient mice suffer from massive lymphoproliferation (Chambers et al., supra). It has been reported that CTLA-4 blockade augments T cell responses in vitro (Walunas et al.,*Immunity.* 1:405-413 (1994)) and in vivo (Kearney (1995) *J. Immunol.* 155:1032-1036), exacerbates antitumor immunity (Leach (1996) *Science.* 271:1734-1736), and enhances an induced autoimmune disease (Luhder (1998) *J. Exp. Med.* 187:427-432). It has also been reported that CTLA-4 has an alternative or additional impact on the initial character of the T cell immune response (Chambers (1997) *Curr. Opin. Immunol.* 9:396-404; Bluestone (1997) *J. Immunol.* 158:1989-1993; Thompson (1997) *Immunity* 7:445-450). This is consistent with the observation that some autoimmune patients have autoantibodies to CTLA-4. It is possible that CTLA-4 blocking antibodies have a pathogenic role in these patients (Matsui (1999) J. Immunol. 162:4328-4335).

Non-human CTLA-4 antibodies have be used in the various studies discussed above. However, one of the major impediments facing the development of in vivo therapeutic and diagnostic applications for antibodies in humans is the intrinsic immunogenicity of non-human immunoglobulins. For example, when immunocompetent human patients are administered therapeutic doses of rodent monoclonal antibodies, the patients produce antibodies against the rodent immunoglobulin sequences; these human anti-mouse antibodies (HAMA) neutralize the therapeutic antibodies and can cause acute toxicity. These and other deficiencies in the previous antibodies are overcome by the provision of human antibodies to CTLA-4 by the present invention.

SUMMARY OF THE INVENTION

The present invention provides a human sequence antibody that specifically binds to human. CTLA-4 and a human sequence antibody that specifically binds to human CTLA-4 which is substantially free of non-immunoglobulin associated human proteins.

In a related aspect, the invention also provides a therapeutically-effective human sequence antibody that specifically binds to human CTLA-4. In some embodiments, the therapeutically-effective human sequence antibody binds to CTLA-4 on the cell surface of normal human T cells. In other embodiments, the T cell subpopulations marked by CD antigens CD4, CD8, CD25, and CD69 remain stable during and subsequent to the administration of the therapeutically-effective human sequence antibody. In other embodiments, the therapeutically-effective human sequence antibody binds CTLA-4 on the cell surface of normal human T cells. In other embodiments, the human sequence antibody is well-tolerated in a patient.

Also provided is a composition of polyclonal antibodies comprising a plurality of human sequence antibodies that specifically bind to human CTLA-4. The composition of polyclonal antibodies can comprise at least about 2, 5, 10, 50, 100, 500 or 1000 different human sequence antibodies that specifically bind to human CTLA-4.

The invention also provides human sequence antibodies that specifically bind to human CTLA-4 and which block binding of human CTLA-4 to human B7 or do not block binding of human CTLA-4 to human B7.

The invention also provides human sequence antibodies that bind to human CTLA-4 with an equilibrium association constant (Ka) of at least $10^8$ $M^{-1}$. Also provided are human sequence antibodies that bind to human CTLA-4 with an equilibrium association constant (Ka) of at least $10^9 M^{-1}$.

The invention also provides human sequence antibodies that specifically bind to human CTLA-4 that block binding of human CTLA-4 to human B7 by at least about 10%, 20%, 30%, 40%, 50%, 60%, 70%, 80%, 90%, 99%, or 100%.

The invention also provides human sequence antibodies that specifically bind to human CTLA-4 having an antibody heavy chain of either IgG or IgM. The IgG antibody heavy chain can be IgG1, IgG2, IgG3 or IgG4. The invention also provides human sequence antibodies wherein the antibody light chain is a kappa light chain. The human sequence antibody can be encoded by human IgG heavy chain and human kappa light chain nucleic acids that comprise nucleotide sequences in their variable regions as set forth in SEQ ID NO:2 through SEQ ID NO:23, respectively.

The invention also provides a human sequence antibody wherein the human sequence antibody is encoded by human IgG heavy chain and human kappa light chain nucleic acids that comprise nucleotide sequences in their variable regions as set forth in SEQ ID NO:16 and SEQ ID NO:6, respectively.

The invention also provides a human sequence antibody wherein the human sequence antibody is encoded by human IgG heavy chain and human kappa light chain nucleic acids that comprise nucleotide sequences in their variable regions as set forth in SEQ ID NO:18 and SEQ ID NO:8, respectively.

The invention also provides a human sequence antibody wherein the human sequence antibody is encoded by human IgG heavy chain and human kappa light chain nucleic acids that comprise nucleotide sequences in their variable regions as set forth in SEQ ID NO:22 and SEQ ID NO:12, respectively.

The invention also provides a human sequence antibody wherein the human sequence antibody is encoded by heavy chain and light chain variable region amino acid sequences as set for the in SEQ ID NO:17 and SEQ ID NO:7, respectively.

The invention provides a human sequence antibody wherein the human sequence antibody is encoded by heavy chain and light chain variable region amino acid sequences as set for the in SEQ ID NO:19 and SEQ ID NO:9, respectively.

The invention also provides a human sequence antibody wherein the human sequence antibody is encoded by heavy chain and light chain variable region amino acid sequences as set for the in SEQ ID NO:23 and SEQ ID NO:13, respectively.

The invention provides a human sequence antibody wherein the human sequence antibody is encoded by human IgG heavy chain and human kappa light chain nucleic acids comprising variable heavy and light chain sequences from V gene segments VH 3-303 and VK A-27, respectively.

The invention also provides a human sequence antibody wherein the human sequence antibody is encoded by human IgG heavy chain and human kappa light chain nucleic acids comprising variable heavy and light chain sequences from V gene segments VH 3-33 and VK L-15, respectively.

Some human sequence antibodies of the invention comprise heavy chain CDR1, CDR2, and CDR3 sequences, SYTMH (SEQ ID NO:27), FISYDGNNKYYADSVKG (SEQ ID NO:32) and TGWLGPFDY (SEQ ID NO:37), respectively, and light chain CDR1, CDR2, and CDR3 sequences, RASQSVGSSYLA (SEQ ID NO:24), GAFSRAT (SEQ ID NO:29), and QQYGSSPWT (SEQ ID NO:35), respectively.

Some human sequence antibodies of the invention comprise heavy chain CDR1, CDR2, and CDR3 sequences, SYTMH (SEQ ID NO:27), FISYDGSNKHYADSVKG (SEQ ID NO:33) and TGWLGPFDY (SEQ ID NO:37), respectively, and light chain CDR1, CDR2, and CDR3 sequences, RASQSVSSSFLA (SEQ ID NO:25), GASSRAT (SEQ ID NO:30), and QQYGSSPWT (SEQ ID NO:35), respectively.

Other human sequence antibodies of the invention comprise heavy chain CDR1, CDR2, and CDR3 sequences, SYGMH (SEQ ID NO:28), VIWYDGSNKYYADSVKG (SEQ ID NO:34) and APNYIGAFDV (SEQ ID NO:38), respectively, and light chain CDR1, CDR2, and CDR3 sequences, RASQGISSWLA (SEQ ID NO:26), AASSLQS (SEQ ID NO:31), and QQYNSYPPT (SEQ ID NO:36), respectively.

The invention also provides human sequence antibodies that specifically bind to human CTLA-4, wherein said human sequence antibody is produced by a transgenic non-human animal. The transgenic non-human animal can be a mouse.

The invention also provides a human sequence antibody that specifically bind to human CTLA-4 that is a Fab fragment.

The invention provides a polyvalent complex comprising at least two human sequence antibodies each of which specifically binds to human CTLA-4. The two different antibodies can be linked to each other covalently or non-covalently.

The invention provides a nucleic acid encoding a heavy chain of a human sequence antibody. The nucleic acid can comprise a nucleotide sequence as set forth in SEQ ID NO:1.

The invention provides a transgenic non-human animal having a genome comprising a human sequence heavy chain transgene and a human sequence light chain transgene, which animal has been immunized with a human CTLA-4, or a fragment or an analog thereof, whereby the animal expresses human sequence antibodies to the human CTLA-4. The transgenic non-human animal can be a transgenic mouse. The transgenic mouse can comprise HCo7 or HCo12.

The invention provides a hybridoma cell line comprising a B cell obtained from a transgenic non-human animal having a genome comprising a human sequence heavy chain transgene and a human sequence light chain transgene, wherein the hybridoma produces a human sequence antibody that specifically binds to human CTLA-4. In a related embodiment, the hybridoma secretes a human sequence antibody that specifically binds human CTLA-4 or binding fragment thereof, wherein the antibody is selected from the group consisting of: a human sequence antibody comprising heavy chain heavy chain CDR1, CDR2, and CDR3 sequences, SYTMH (SEQ ID NO:27), FISYDGNNKYYADSVKG (SEQ ID NO:32) and TGWLGPFDY (SEQ ID NO:37), respectively, and light chain CDR1, CDR2, and CDR3 sequences, RASQSVGSSYLA (SEQ ID NO:24), GAFSRAT (SEQ ID NO:29), and QQYGSSPWT (SEQ ID NO:35), respectively, and heavy chain and light chain variable region amino acid sequences as set forth in SEQ ID NO:17 and SEQ ID NO:7, respectively; a human sequence antibody comprising heavy chain CDR1, CDR2, and CDR3 sequences, SYTMH (SEQ ID NO:27), FISYDGSNKHYADSVKG (SEQ ID NO:33) and TGWLGPFDY (SEQ ID NO:37), respectively, and light chain CDR1, CDR2, and CDR3 sequences, RASQSVSSSFLA (SEQ ID NO:25), GASSRAT (SEQ ID NO:30), and QQYGSSPWT (SEQ ID NO:35), respectively, and heavy chain and light chain variable region amino acid sequences as set forth in SEQ ID NO:19 and SEQ ID NO:9, respectively; or a human sequence antibody of claim 1, comprising heavy chain CDR1, CDR2, and CDR3 sequences, SYGMH (SEQ ID NO:28), VIWYDGSNKYYADSVKG (SEQ ID NO:34) and APNYIGAFDV (SEQ ID NO:38), respectively, and light chain CDR1, CDR2, and CDR3 sequences, RASQGISSWLA (SEQ ID NO:26), AASSLQS (SEQ ID NO:31), and QQYNSYPPT (SEQ ID NO:36), respectively, and heavy chain and light chain variable region amino acid sequences as set forth in SEQ ID NO:23 and SEQ ID NO:13, respectively.

The invention provides a pharmaceutical composition comprising a human sequence antibody that specifically binds to human CTLA-4 and a pharmaceutically acceptable carrier. The pharmaceutical composition can further comprise an agent effective to induce an immune response against a target antigen. Also provided are chemotherapeutic agents. In addition, antibodies to immunosuppressive molecules are also provided.

The invention provides a method for inducing, augmenting or prolonging an immune response to an antigen in a patient, comprising administering to the patient an effective dosage of a human sequence antibody that specifically binds to human CTLA-4, wherein the antibody blocks binding of human CTLA-4 to human B7. The antigen can be a tumor antigen, or the antigen can be from a pathogen. The tumor antigen can also be telomerase. The pathogen can be a virus, a bacterium, a fungus or a parasite. The pathogen can also be an HIV. This method can further comprise administering the antigen, or a fragment or an analog thereof, to the patient, whereby the antigen in combination with the human sequence antibody induces, augments or prolongs the immune response. The antigen can be a tumor antigen or a component of an amyloid formation in the patient, such as a patient suffering from Alzheimer's disease and the antigen is AB peptide. This method can further comprise administering a cytokine to the patient.

The invention provides a method of suppressing an immune response in a patient, comprising administering to the patient an effective dosage of a polyvalent preparation comprising at least two human sequence antibodies to human CTLA-4 linked to each other. The invention also provides a method of suppressing an immune response in a patient, comprising administering to the patient an effective dosage of a polyclonal preparation comprising at least two human sequence antibodies to human CTLA-4.

The present invention further provides isolated or recombinant human sequence antibodies and human monoclonal antibodies which specifically bind to human CTLA-4, as well as compositions containing one or a combination of such antibodies. Some of the human sequence antibodies of the invention are characterized by binding to human CTLA-4 with high affinity, and/or by blocking the interaction of human CTLA-4 with its ligand, the human B7-1 and B7-2 molecules. Accordingly, the human sequence antibodies and the human monoclonal antibodies of the invention can be used as diagnostic or therapeutic agents in vivo and in vitro.

The human sequence antibodies of the invention can encompass various antibody isotypes, or mixtures thereof, such as IgG1, IgG2, IgG3, IgG4, IgM, IgA1, IgA2, IgAsec, IgD, and IgE. Typically, they include IgG1 (e.g., IgG1k) and IgM isotypes. The human sequence antibodies can be full-length (e.g., an IgG1 or IgG4 antibody) or can include only an antigen-binding portion (e.g., a Fab, F(ab')2, Fv or a single chain Fv fragment). Some human sequence antibodies are recombinant human sequence antibodies. Some human sequence antibodies are produced by a hybridoma which includes a B cell obtained from a transgenic non-human animal, e.g., a transgenic mouse, having a genome comprising a human heavy chain transgene and a human light chain transgene. The hybridoma can be made by, e.g., fusing the B cell to an immortalized cell. Some human sequence antibodies of the invention are produced by hybridomas referred to as 4C8, 4E10, 4E10.5, 5A8, 5C4, 5C4.1.3, 5D7, 5D7.1, 5E10, 5E10.12, 5G1, 5G1.4, 6A10, 6C9, 6C9.6, 6D9, 6D9.7, 6G4, 7E4, 7E4.4, 7E6, 7118, 8E8, 8E8.4, 8F8, 8F8.19, 8H1, 9810, 9A10.1, 9B9, 9C1, 9G5, 105B, 10B5.8, 10B9, 10B9.2, 10D1, 10D1.3, 10E11, 10E4, 10E4.5, 11B4, 11D10, 11E4, 11E4.1, 11E8, 11F10, 11F11, 11F9, 11O1, 11G1.5, 1C7, 1H8.8, 2A7, 2A7.6, 2E2, 2E2,7, 2E7, 2E7.2, 2G1, 2G1.2, 3C12, 3E10, 3E10.5, 3E6, 3E6.0, 3F10, 4A1, 4B6 and 4B6.12. Suffixes after the decimal point indicate different clonal isolates of the same hybridoma cell lines.

Some human sequence anti-CTLA-4 antibodies of the present invention can be characterized by one or more of the following properties: a) specificity for human CTLA-4 (specifically binding to human CTLA-4); b) a binding affinity to human CTLA-4 with an equilibrium association constant ($K_a$) of at least about $10^7 M^{-1}$, or about $10^9 M^{-1}$, or about $10^{10} M^{-1}$ to $10^{11} M^{-1}$ or higher; c) a kinetic association constant ($k_a$) of at least about $10^3$, about $10^4$, or about $10^5$ $m^{-1}s^{-1}$; and/or, d) a kinetic disassociation constant ($k_d$) of at least about $10^3$, about $10^4$, or about $10^5$ $m^{-1}s^{-1}$.

In another aspect, the invention provides nucleic acid molecules encoding the human sequence antibodies, or antigen-binding portions, of the invention. Accordingly, recombinant expression vectors that include the antibody-encoding nucleic acids of the invention, and host cells transfected with such vectors, are also encompassed by the invention, as are methods of making the antibodies of the invention by culturing these host cells.

In yet another aspect, the invention provides isolated B-cells from a transgenic non-human animal, e.g., a transgenic mouse, which are capable of expressing various isotypes (e.g., IgG, IgA and/or IgM) of human monoclonal antibodies that specifically bind to human CTLA-4. The isolated B cells can be obtained from a transgenic non-human animal, e.g., a transgenic mouse, which has been immunized with a purified or enriched preparation of human CTLA-4 antigen (or antigenic fragment thereof) and/or cells expressing human CTLA-4. The transgenic non-human animal, e.g., a transgenic mouse, can have a genome comprising a human heavy chain transgene and a human light chain transgene. The isolated B-cells can be immortalized to provide a source (e.g., a hybridoma) of human monoclonal antibodies to human CTLA-4.

Accordingly, the present invention also provides a hybridoma capable of producing human monoclonal antibodies that specifically bind to human CTLA-4. The hybridoma can include a B cell obtained from a transgenic non-human animal, e.g., a transgenic mouse, having a genome comprising a human heavy chain transgene and a human light chain transgene fused to an immortalized cell. The transgenic non-human animal can be immunized with a purified or enriched preparation of human CTLA-4 antigen and/or cells expressing human CTLA-4 to generate antibody-producing hybridomas.

In yet another aspect, the invention provides a transgenic non-human animal, such as a transgenic mouse, which express human monoclonal antibodies (also referred to herein as a "HuMAb-Mouse™") that specifically bind to human CTLA-4. The transgenic non-human animal can be a transgenic mouse having a genome comprising a human heavy chain transgene and a human light chain transgene. The transgenic non-human animal can be immunized with a purified or enriched preparation of CTLA-4 antigen (or antigenic fragment thereof) and/or cells expressing the human CTLA-4. The transgenic non-human animal, e.g., the transgenic mouse, can be capable of producing multiple isotypes of human monoclonal antibodies to human CTLA-4 (e.g., IgG, IgA and/or IgM) by undergoing V-D-J recombination and isotype switching. Isotype switching may occur by, e.g., classical or non-classical isotype switching.

In another aspect, the present invention provides methods for producing human sequence antibodies and human sequence monoclonal antibodies that specifically react with human CTLA-4. Some methods of the invention include immunizing a transgenic non-human animal, e.g., a transgenic mouse, having a genome comprising a human heavy chain transgene and a human light chain transgene, with a purified or enriched preparation of human CTLA-4 antigen and/or cells expressing human CTLA-4. B cells (e.g., splenic B cells) of the animal can then be obtained and fused with myeloma cells to form immortal, hybridoma cells that secrete human monoclonal antibodies against human CTLA-4.

Anti-human CTLA-4 human monoclonal antibodies of the invention, or antigen binding portions thereof (e.g., Fab), can be derivatized or linked to another functional molecule, e.g., another peptide or protein (e.g., an Fab' fragment). For example, an antibody or antigen-binding portion of the invention can be functionally linked (e.g., by chemical coupling, genetic fusion, noncovalent association or otherwise) to one or more other molecular entities. For example, the human sequence anti-CTLA-4 antibody, or antigen binding fragment thereof, can be conjugated to a therapeutic moiety, e.g., a cytotoxic drug, an enzymatically active toxin, or a fragment thereof, a radioisotope, or a small molecule anti-cancer drug. The antibodies of the invention can also be conjugated to cytotoxic pharmaceuticals, e.g., radiolabeled with a cytotoxic agents, such as, e.g., $^{131}$I (e.g., Shen (1997) Cancer 80(12 Suppl):2553-2557), copper-67 (e.g., Deshpande (1988) J. Nucl. Med. 29:217-225) or, e.g., conjugation to the ribosome inactivating protein gelonin (e.g., Boyle (1996) J. of Immunol. 18:221-230).

In another aspect, the present invention provides compositions, e.g., pharmaceutical and diagnostic compositions, comprising a pharmaceutically acceptable carrier and at least one human monoclonal antibody of the invention, or an antigen-binding portion thereof, which specifically binds to human CTLA-4. Some compositions comprise a combination of the human sequence antibodies or antigen-binding portions thereof, preferably each of which binds to a distinct epitope. Compositions, e.g., pharmaceutical compositions, comprising a combination of at least one human sequence antibodies or at least one human monoclonal antibody of the invention, or antigen-binding portions thereof, and at least one bispecific or multispecific molecule of the invention, are also within the scope of the invention.

For in vivo methods, the antibody, or antigen-binding portion thereof (or a bispecific or multispecific molecule of the invention), can be administered to a human subject suffering from a T-cell-related disease, or a disease that can be ameliorated or prevented by augmenting or suppressing or prolonging an immune response.

Human sequence monoclonal antibody and human sequence antibody compositions of the invention also can be administered in combination with other known therapies, e.g., an anti-cancer therapy. Accordingly, the invention provides a method for treating cancer in a subject comprising administering a therapeutically effective amount of a pharmaceutical composition of a human sequence antibody together with a pharmaceutical carrier to the subject. Some such methods include a vaccine. Some such vaccines include a tumor cell vaccine, a GM-CSF-modified tumor cell vaccine, or an antigen-loaded dendritic cell vaccine. In some such methods, the cancer is prostate cancer, melanoma, or epithelial cancer.

Human sequence antibodies to human CTLA-4 can be used in methods of treatment requiring either stimulation of immune responses or suppression. The former indication is treated using antibodies that block binding of human CTLA-4 to human B7. Diseases amenable to treatment by stimulation, augmentation of prolonging of immune responses including cancer, including cancers of the prostate, kidney or colon, pathogenic infections, diseases associated with auto-antigens, e.g., amyloidogenic diseases, including Alzheimer's disease, and diseases with inflammatory or allergic components. Immunosuppression is achieved using a polyvalent preparation comprising at least two different antibodies to human CTLA-4 that are linked to each other. Diseases amenable to treatment include graft versus host disease, host versus graft disease, autoimmune diseases and inflammation.

In yet another aspect, the present invention provides a method for detecting in vitro or in vivo the presence of human CTLA-4 antigen in a sample, e.g., for diagnosing a human CTLA-4-related disease. In some methods, this is achieved by contacting a sample to be tested, along with a control sample, with a human sequence antibody or a human monoclonal antibody of the invention, or an antigen-binding portion thereof (or a bispecific or multispecific molecule), under conditions that allow for formation of a complex between the antibody and human CTLA-4. Complex formation is then detected (e.g., using an ELISA) in both samples, and any statistically significant difference in the formation of complexes between the samples is indicative the presence of human CTLA-4 antigen in the test sample.

A further understanding of the nature and advantages of the present invention may be realized by reference to the remaining portions of the specification, the figures and claims.

All publications, figures, GenBank Accession references (sequences), ATCC Deposits, patents and patent applications cited herein are hereby expressly incorporated by reference for all purposes to the same extent as if each was so individually denoted.

BRIEF DESCRIPTION OF THE DRAWINGS

FIG. 1A) Schematic diagram of the genomic structure of the µ locus. The filled boxes represent the µ exons; FIG. 1B) Schematic diagram of the CmD targeting vector. The dotted lines denotes those genomic µ sequences included in the construct. Plasmid sequences are not shown; FIG. 1C) Schematic diagram of the targeted locus in which the neo cassette has been inserted into µl. The box at the lower right shows those RFLP's diagnostic of homologous recombination between the targeting construct and the µ locus. The RFLP's were detected by Southern blot hybridization using probe A, the 915 bp Sac I fragment is shown in FIG. 1C.

FIGS. 4A-B show preliminary nucleotide sequence data for the heavy (FIG. 4A; SEQ ID NO:2) and light chain (FIG. 4B; SEQ ID NO:4) fragment of the anti-CTLA-4 antibody 10D1.3.

FIGS. 5 and 5A show the nucleotide sequences of the light chain variable Regions ($V_K$) of Anti-Human CTLA-4 Antibodies. The anti-CTLA-4 antibodies 10D1 (SEQ ID NO:6) and 4B6 (SEQ ID NO:8) derived from the $V_K$ A-27 germline sequence (SEQ ID NO:4) are depicted at the top of FIG. 5. The anti-CTLA-4 antibody 1E2 (SEQ ID NO:12) derived from the $V_K$ L-15 germline sequence (SEQ ID NO:10) is shown at the bottom of FIG. 5 and FIG. 5A. The $V_K$ sequences of three anti-CTLA-4 antibodies are aligned with their germline encoded $V_K$ gene sequences. The complementary determining residues (CDR) are labeled. Dashes denote sequence identity.

FIGS. 6 and 6A show the nucleotide sequences of the heavy chain variable Regions ($V_H$) of Anti-Human CTLA-4 Antibodies. The anti-CTLA-4 antibodies 10D1 (SEQ ID NO:16) and 4B6 (SEQ ID NO:18) derived from the $V_H$ 3-30.3 germline sequence (SEQ ID NO:14) are depicted at the top of FIG. 6. The anti-CTLA-4 antibody 1 E2 (SEQ ID NO:22)

derived from the $V_H$ 3-33 germline sequence (SEQ ID NO:20) is shown at the bottom of FIG. 6 and FIG. 6A. The $V_H$ sequences of three anti-CTLA-4 antibodies are aligned with their germline encoded sequences. The complementary determining residues (CDR) are labeled. Dashes denote sequence identity.

FIG. 7 shows the predicted amino acid sequences of the light chain Variable Regions of Anti-Human CTLA-4 Antibodies. The predicted amino acid $V_K$ sequences of the anti-CTLA-4 antibodies described in FIG. 5 are shown. The anti-CTLA-4 antibodies 10D1 (SEQ ID NO:7) and 4B6 (SEQ ID NO:9) derived from the $V_K$ A-27 germline sequence (SEQ ID NO:5) are depicted at the top of the Figure. The anti-CTLA-4 antibody 1E2 (SEQ ID NO:13) derived from the $V_K$ L-15 germline sequence (SEQ ID NO:11) is shown at the bottom of the Figure.

FIG. 8 shows the predicted amino acid sequences of the heavy chain Variable Regions of Anti-Human CTLA-4 Antibodies. The predicted amino acid $V_H$ sequences of the anti-CTLA-4 antibodies described in FIG. 6 are shown. The anti-CTLA-4 antibodies 10D1 (SEQ ID NO:17) and 4B6 (SEQ ID NO:19) derived from the $V_H$ 3-30.3 germline sequence (SEQ ID NO:15) are depicted at the top of the Figure. The anti-CTLA-4 antibody 1 E2 (SEQ ID NO:23) derived from the $V_H$ 3-33 germline sequence (SEQ ID NO:21) is shown at the bottom of the Figure.

Figure 9:
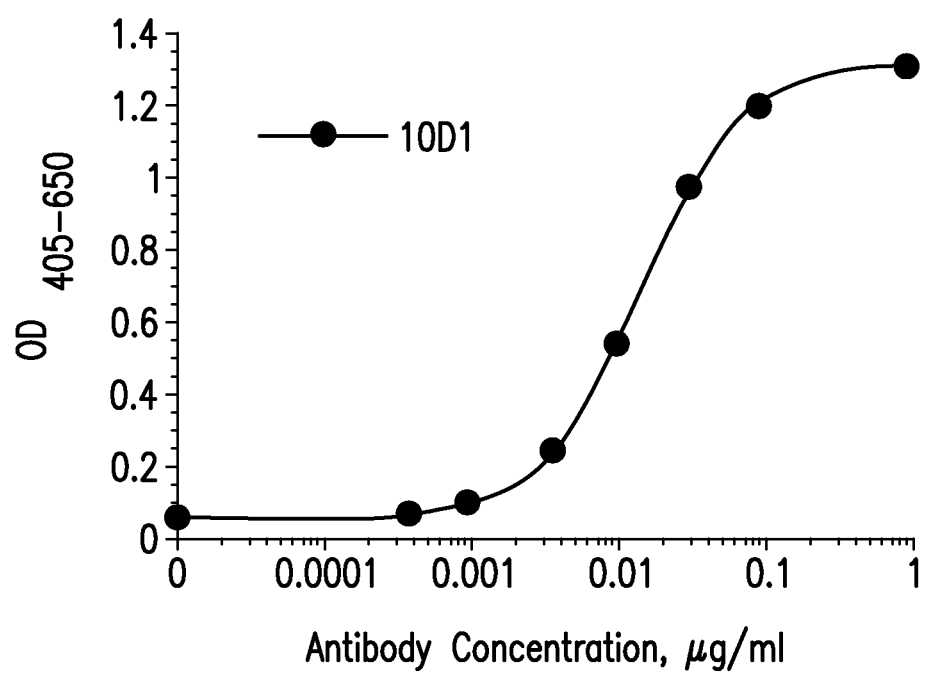

FIG. 9 shows the results of binding experiments of MAb 10D1 to recombinant human CTLA-4 by ELISA. MAb 10D1 binds with dose-dependent and saturating kinetics to purified recombinant CTLA-4.

Figure 10:
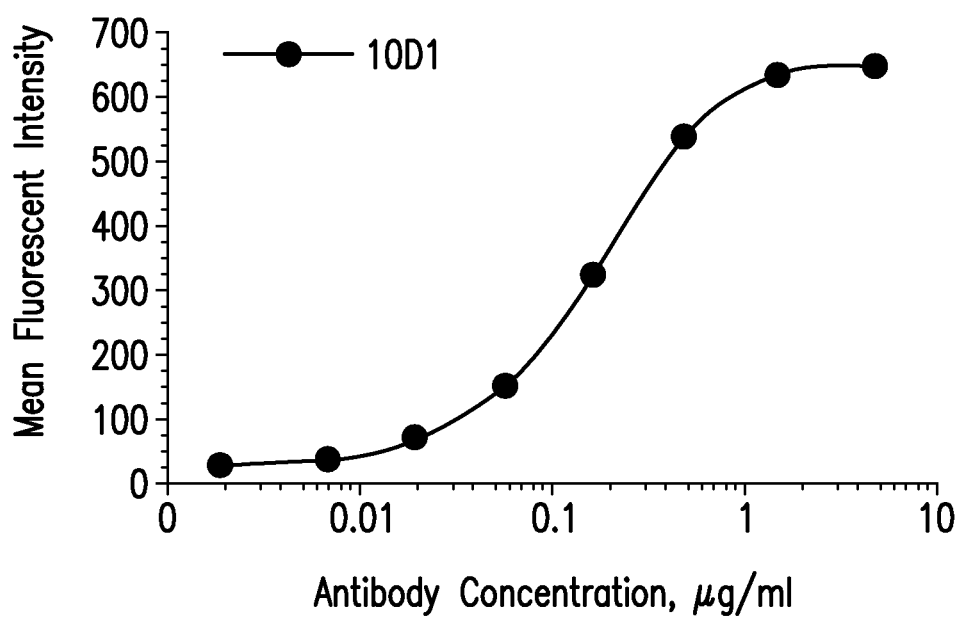

FIG. 10 shows the binding of 10D1 to a CTLA4-expressing T-cell line. These data show that MAb 10D1 binds with dose-dependent and saturating kinetics to cells expressing CTLA-4.

Figure 11:
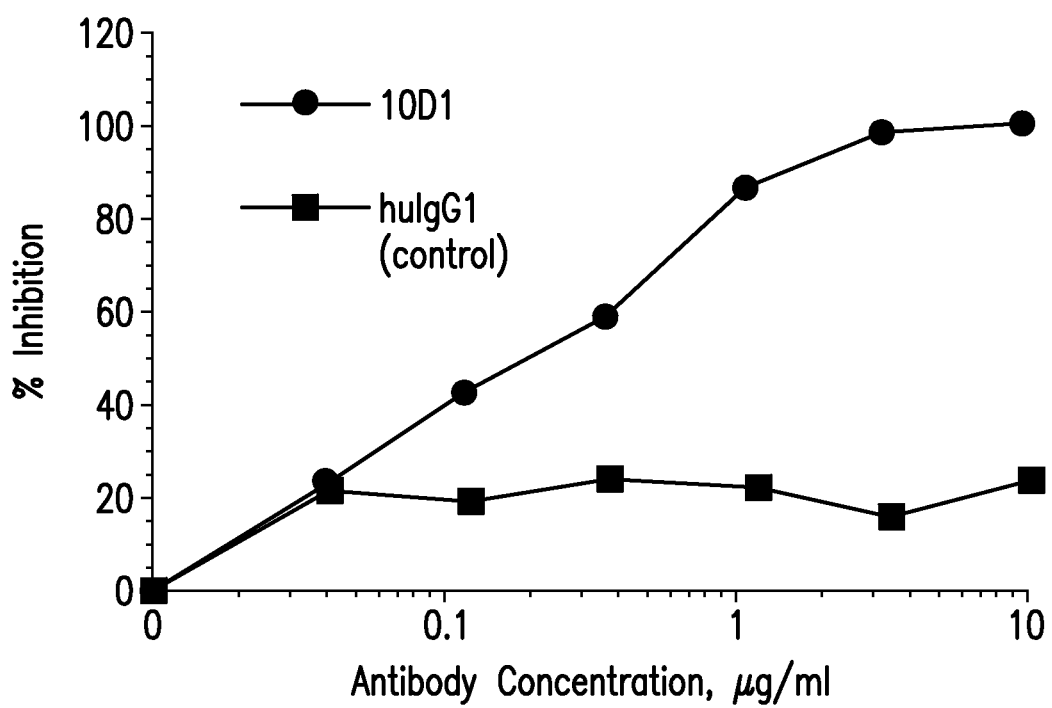

FIG. 11 shows inhibition of binding of human B7.21 g to CTLA4-expressing T-cells. These data show that MAb 10D1 can efficiently block B7.2 binding to CTLA-4 as compared to a control human MAb.

Figure 12:
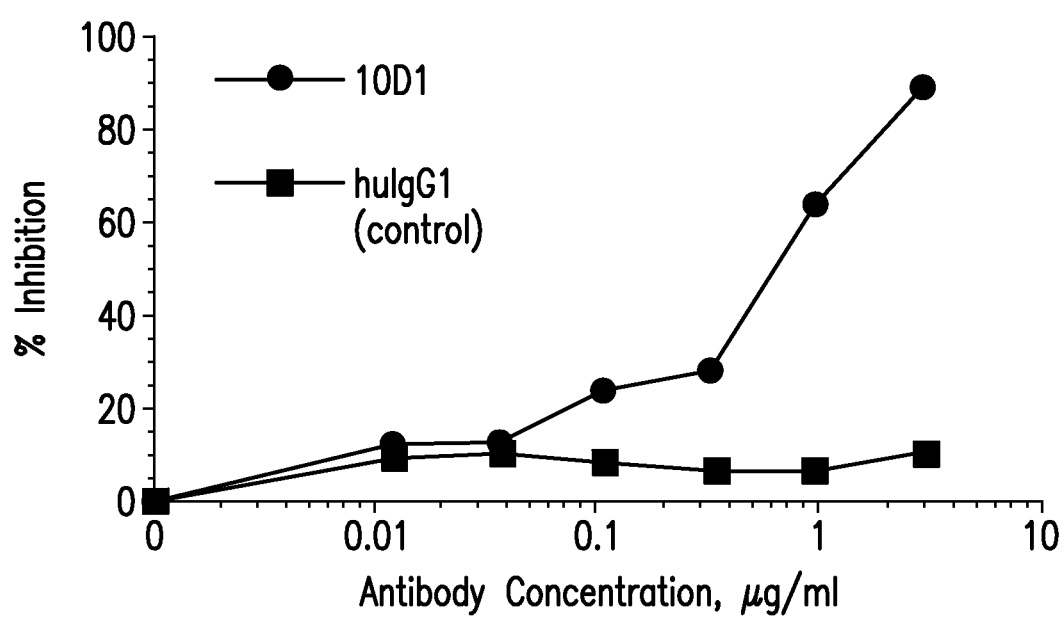

FIG. 12 shows the results for blocking CTLA4-FITC binding to murine B7.1-expressing cells. These data show that MAb 10D1 can efficiently block CTLA-4 binding to B7.1 as compared to a control human MAb.

Figure 13A:
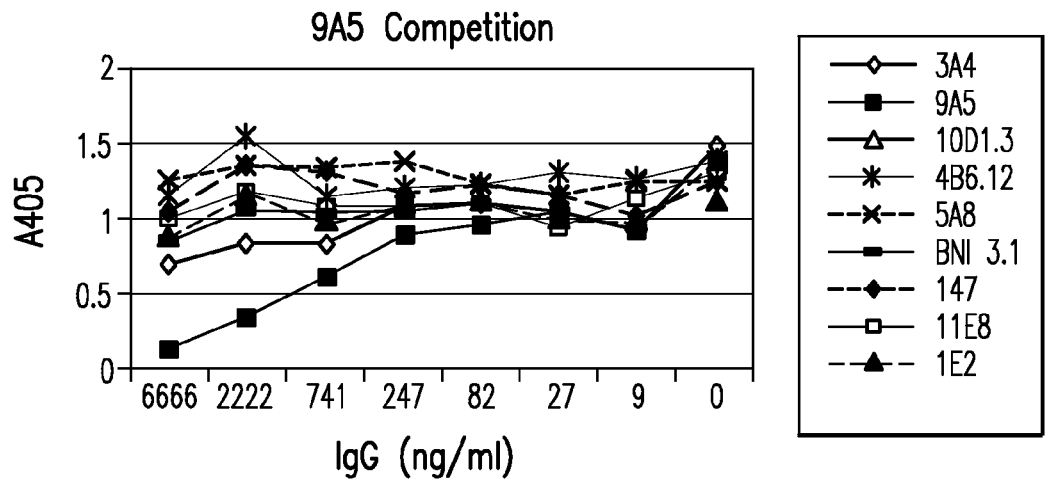
Figure 13B:
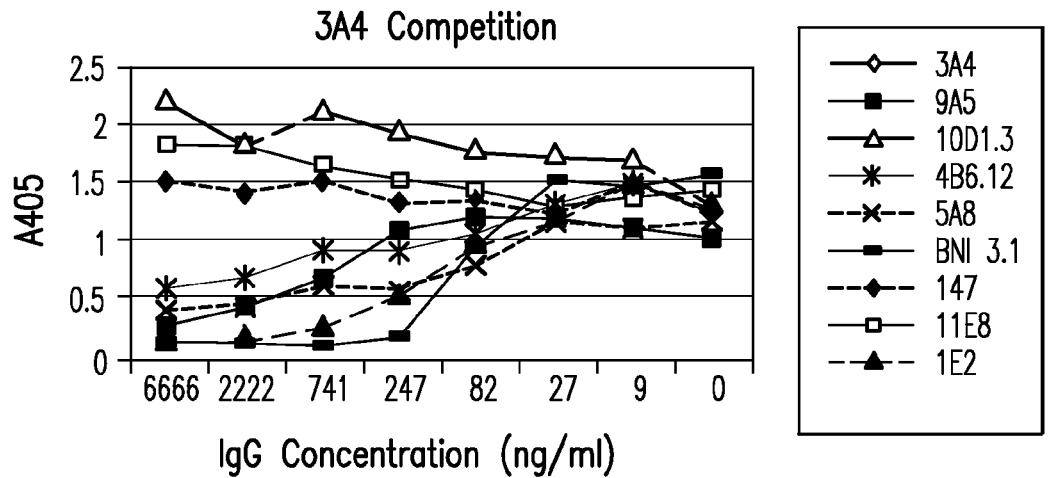
Figure 13C:
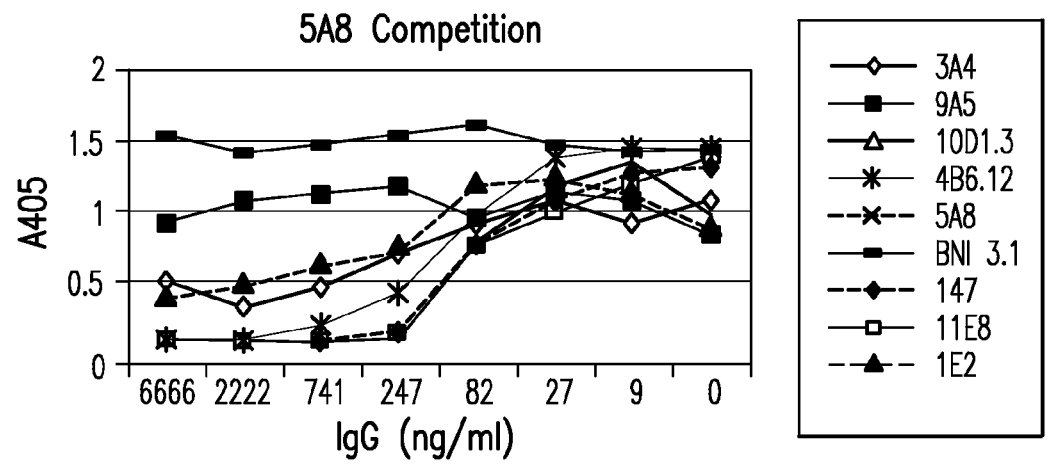
Figure 13D:
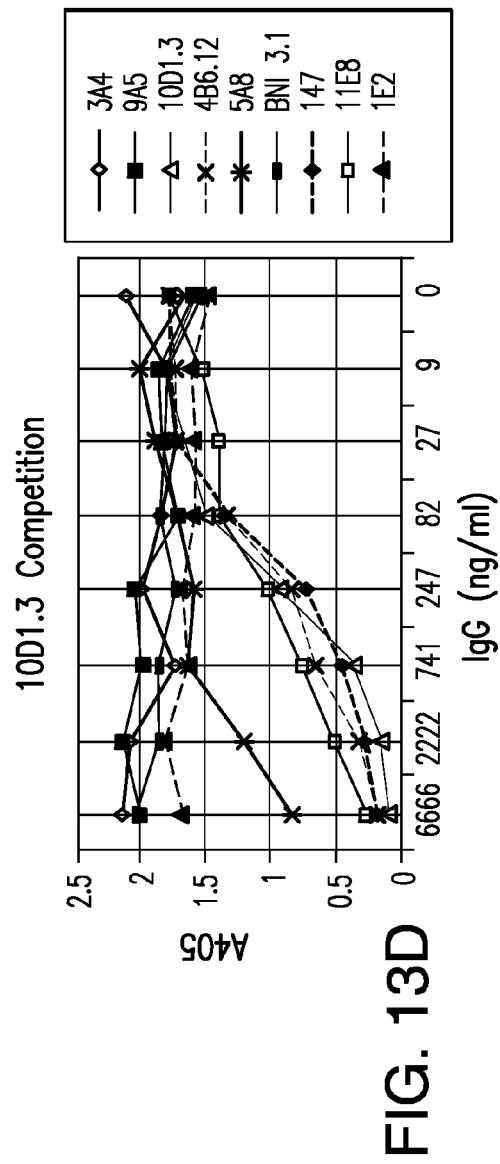
Figure 13E:
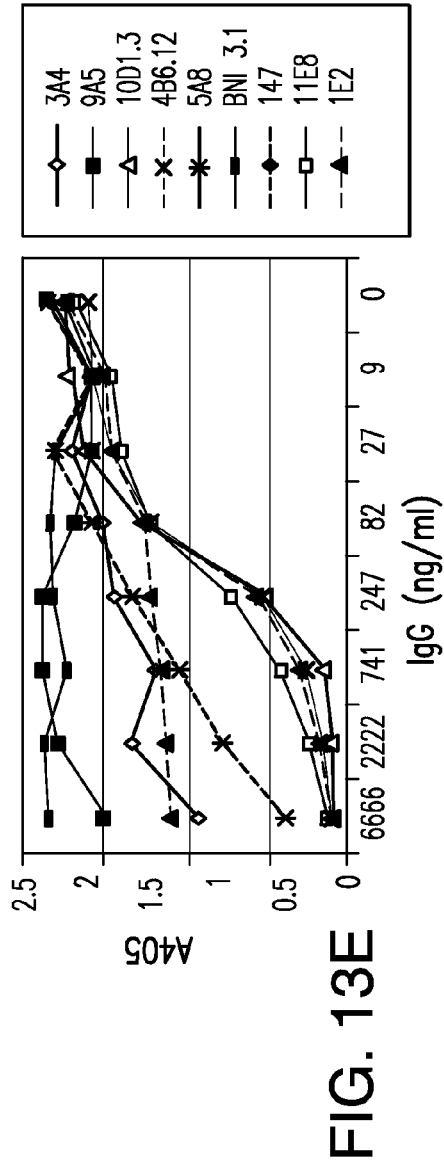
Figure 13F:
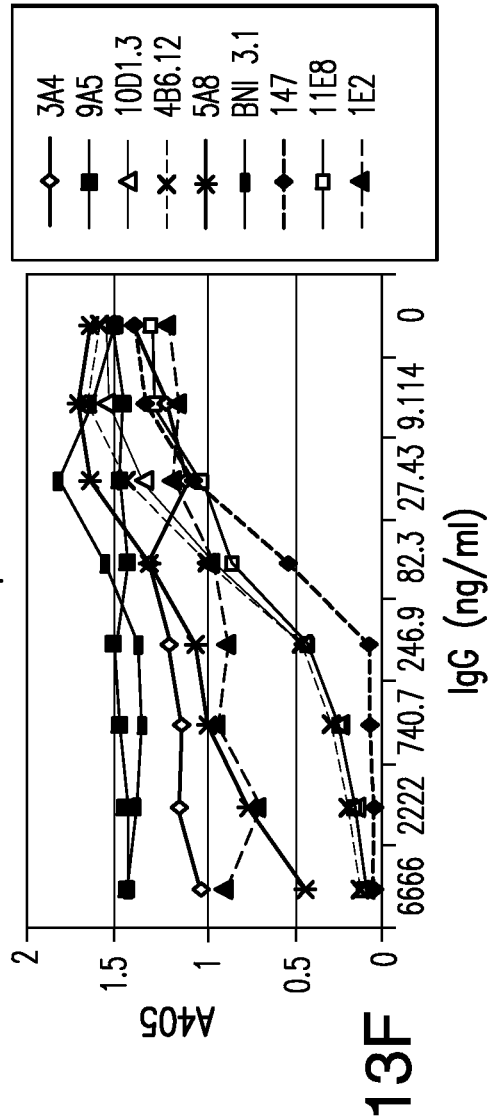
Figure 13G:
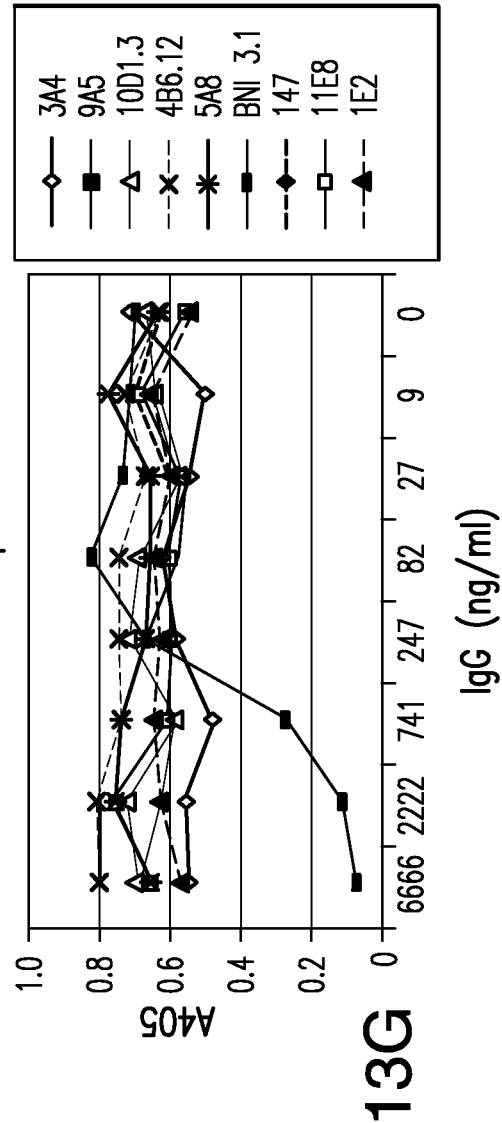

FIGS. 13A-G show competitive ELISAs of anti-CTLA-4 human MAbs demonstrating epitope group classifications. FIG. 13(A) shows results of antibody 9A5 competitive ELISA. FIG. 13(B) shows results of antibody 3A4 competitive ELISA. FIG. 13(C) shows results of antibody 5A8 competitive ELISA. FIG. 13(D) shows results of antibody 10D1.3 competitive ELISA. FIG. 13(E) shows results of antibody 486.12 competitive ELISA. FIG. 13(F) shows results of antibody 147 competitive ELISA. FIG. 13(G) shows results of antibody BNI 3.1 competitive ELISA.

Figure 14A:
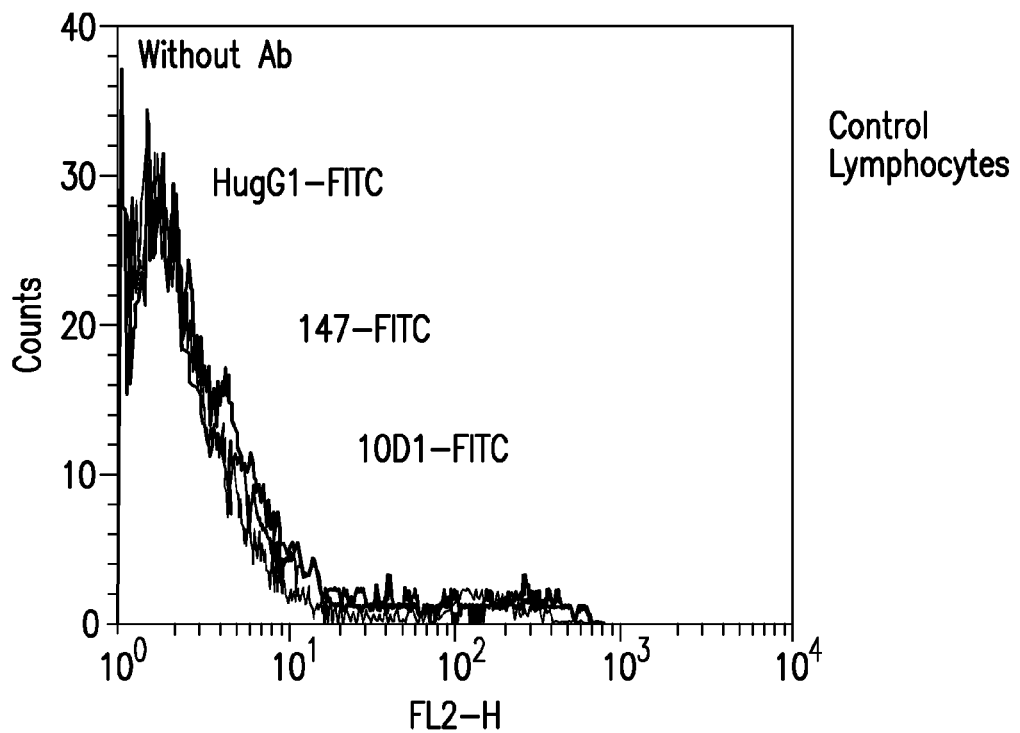
Figure 14B:
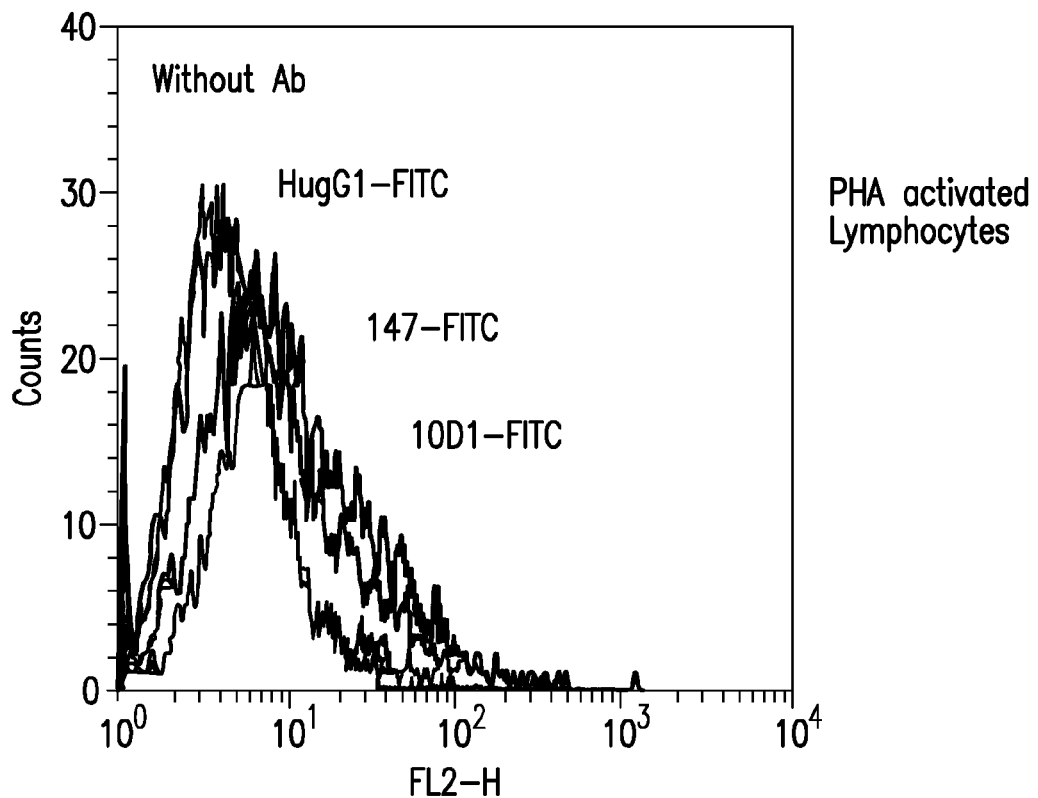

FIGS. 14A-B show CTLA-4 expression on PHA-stimulated T-cells. Activated T cells express low but detectable levels of CTLA-4 at the cell surface, as shown in FIG. 14B, and control T cells do not (FIG. 14A).

Figure 15:
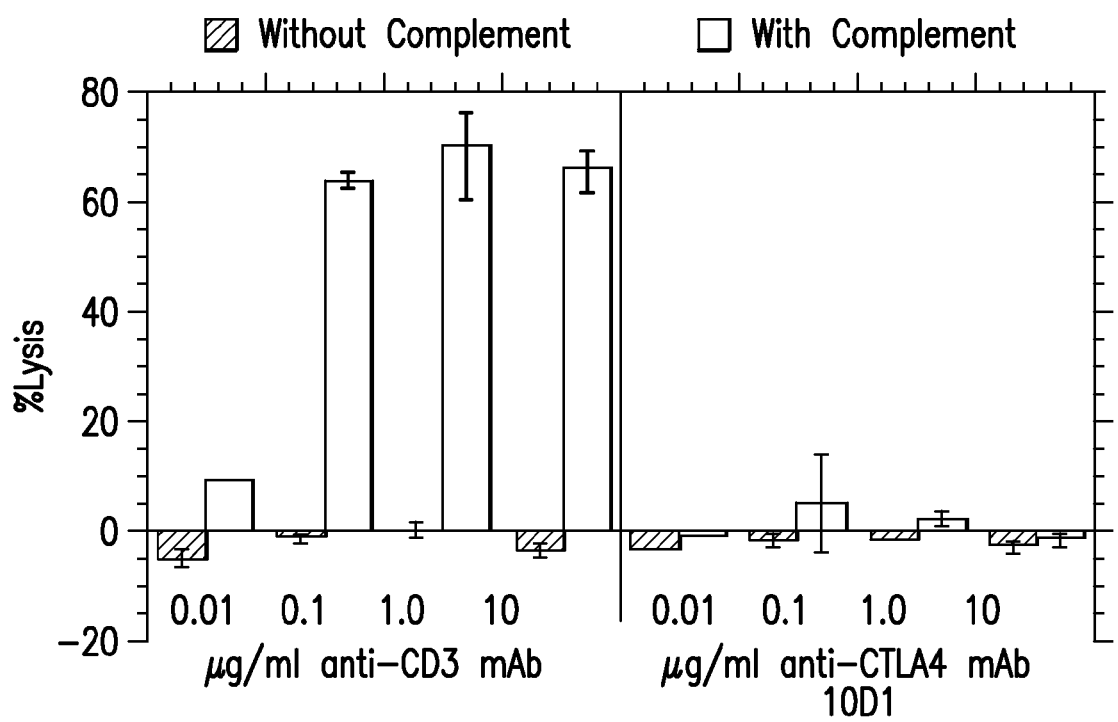

FIG. 15 shows the results of MAb 10D1 in Complement Dependent Lysis of Activated T Cells. No lysis of PHA-activated T cells is observed.

Figure 16:
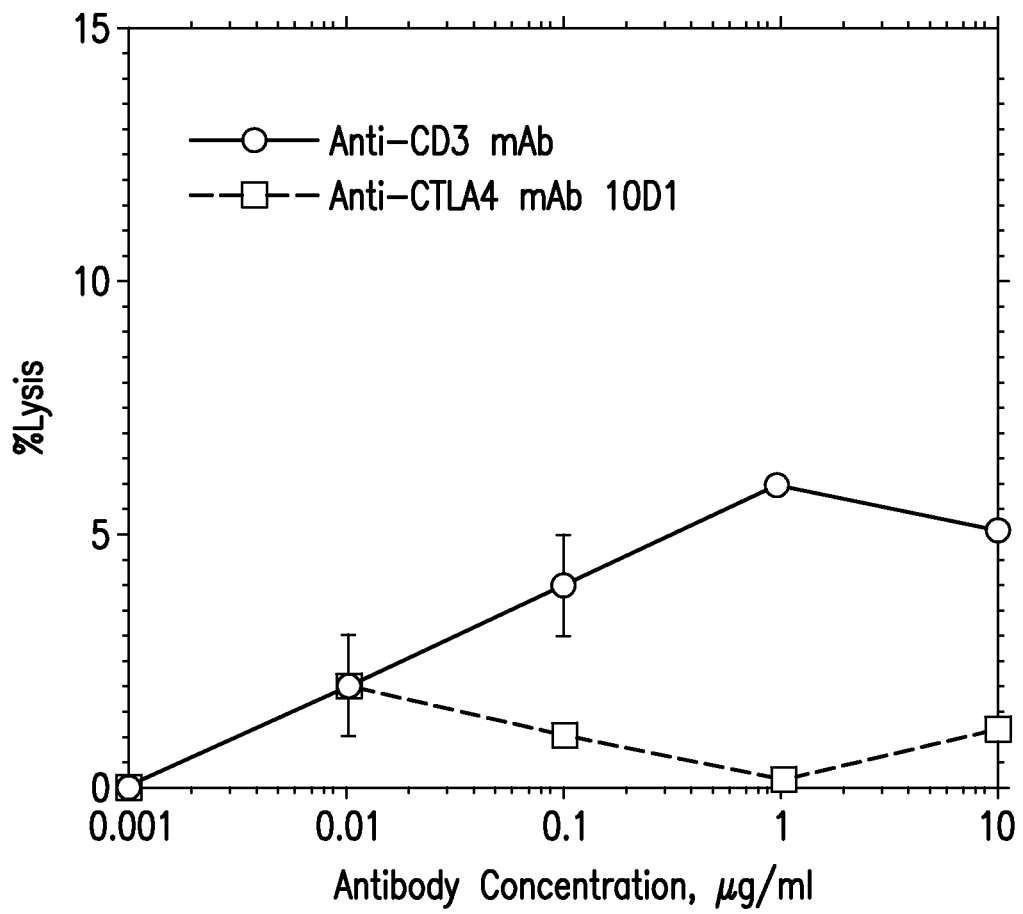

FIG. 16 shows the results of MAb 10D1 in Antibody-Dependent Lysis of Activated T Cells. No lysis of PHA-activated T cells is observed with 10D1 and mononuclear cells.

Figure 17A:
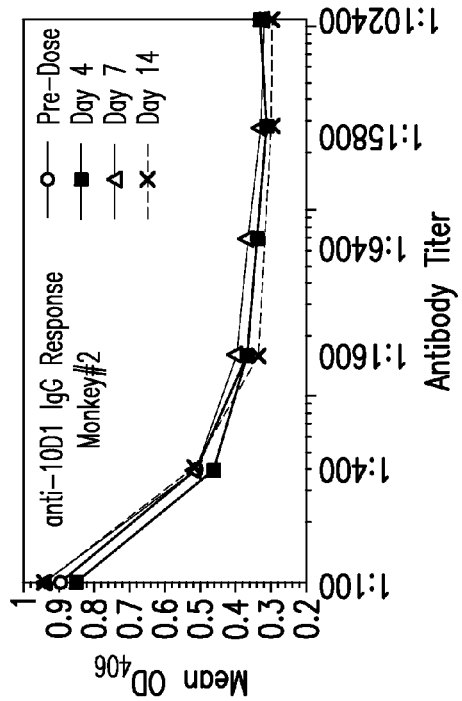
Figure 17B:
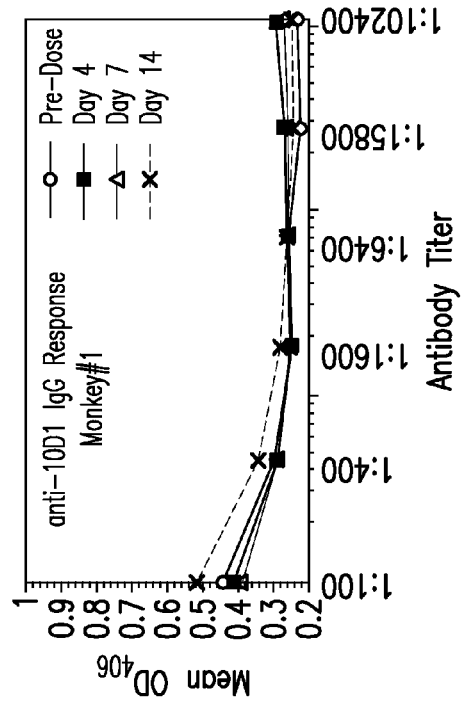
Figure 17C:
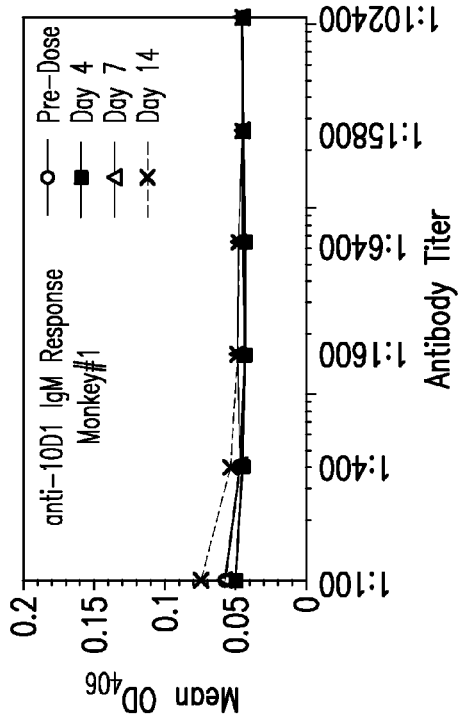
Figure 17D:
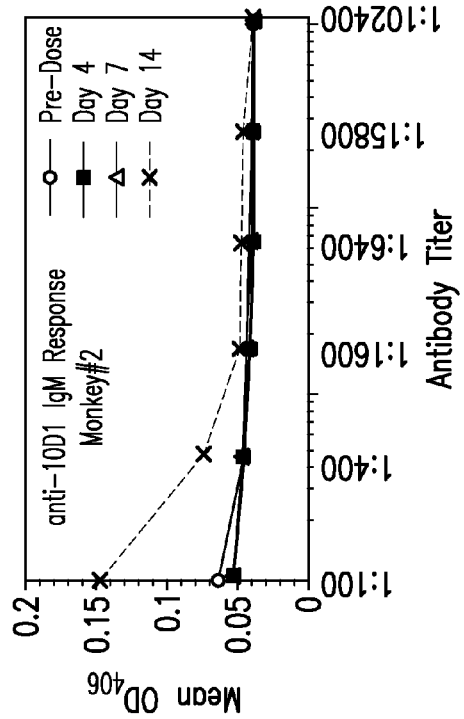

FIGS. 17A-D show anti-10D1 IgM and IgG responses in cynomolgus monkeys injected with 10D1 antibody. FIGS. 17A and 17C show anti-10D1 IgM response. FIGS. 17B and 17D show anti-10D1 IgG response. No significant antibody response to 10D1 is observed.

Figure 18:
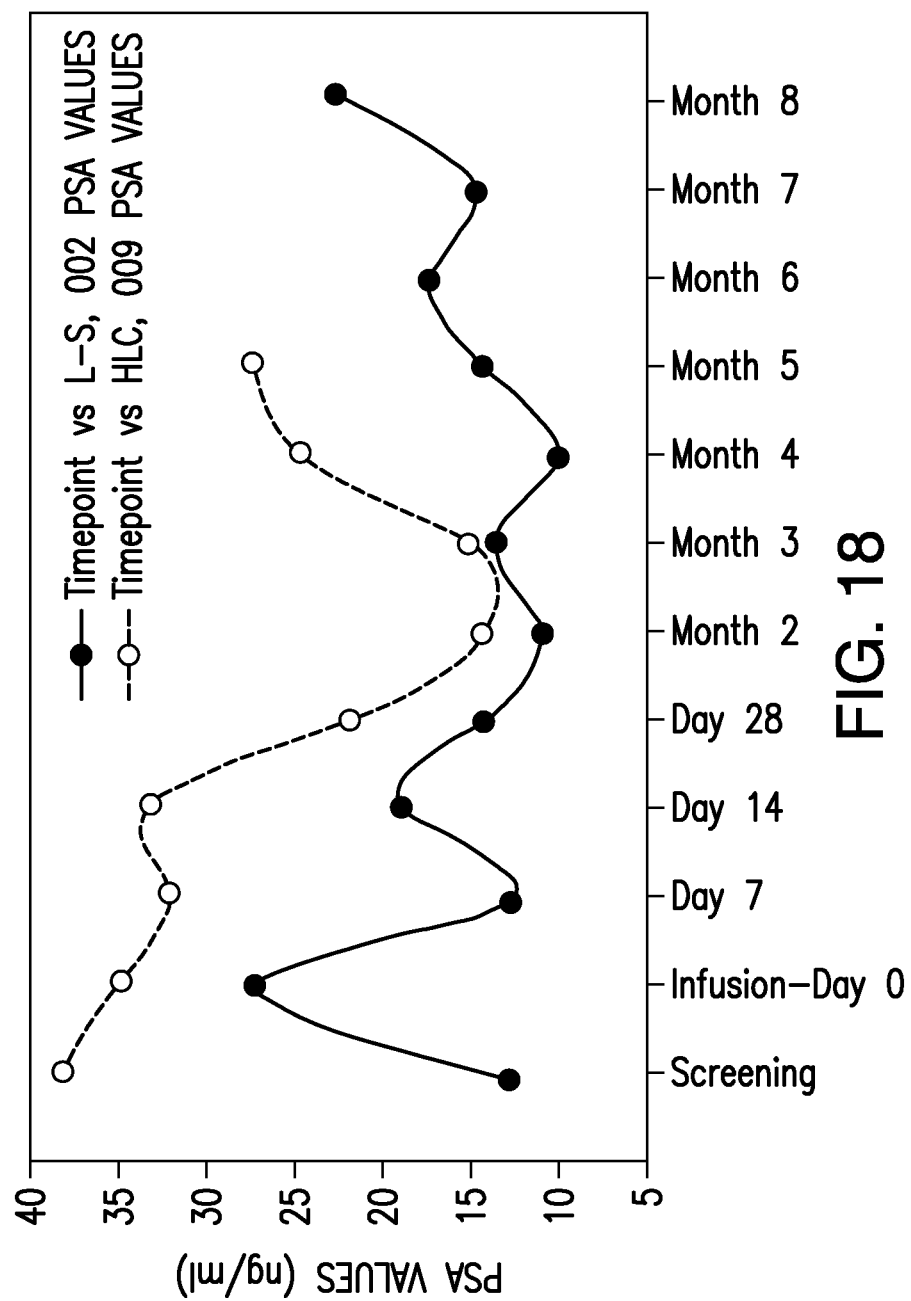

FIG. 18 shows prostate specific antigen (PSA) levels in ng/ml in two human patients at various time points after infusion of an anti-CTLA4 antibody at day 0.

FIGS. 19A-B show the plasma levels of anti-HbsAg antibody in primates treated with either a HbsAg vaccine in combination with the anti-CTLA4 antibody 10D1 or the vaccine in combination with a control IgG1 antibody.

Figure 20:
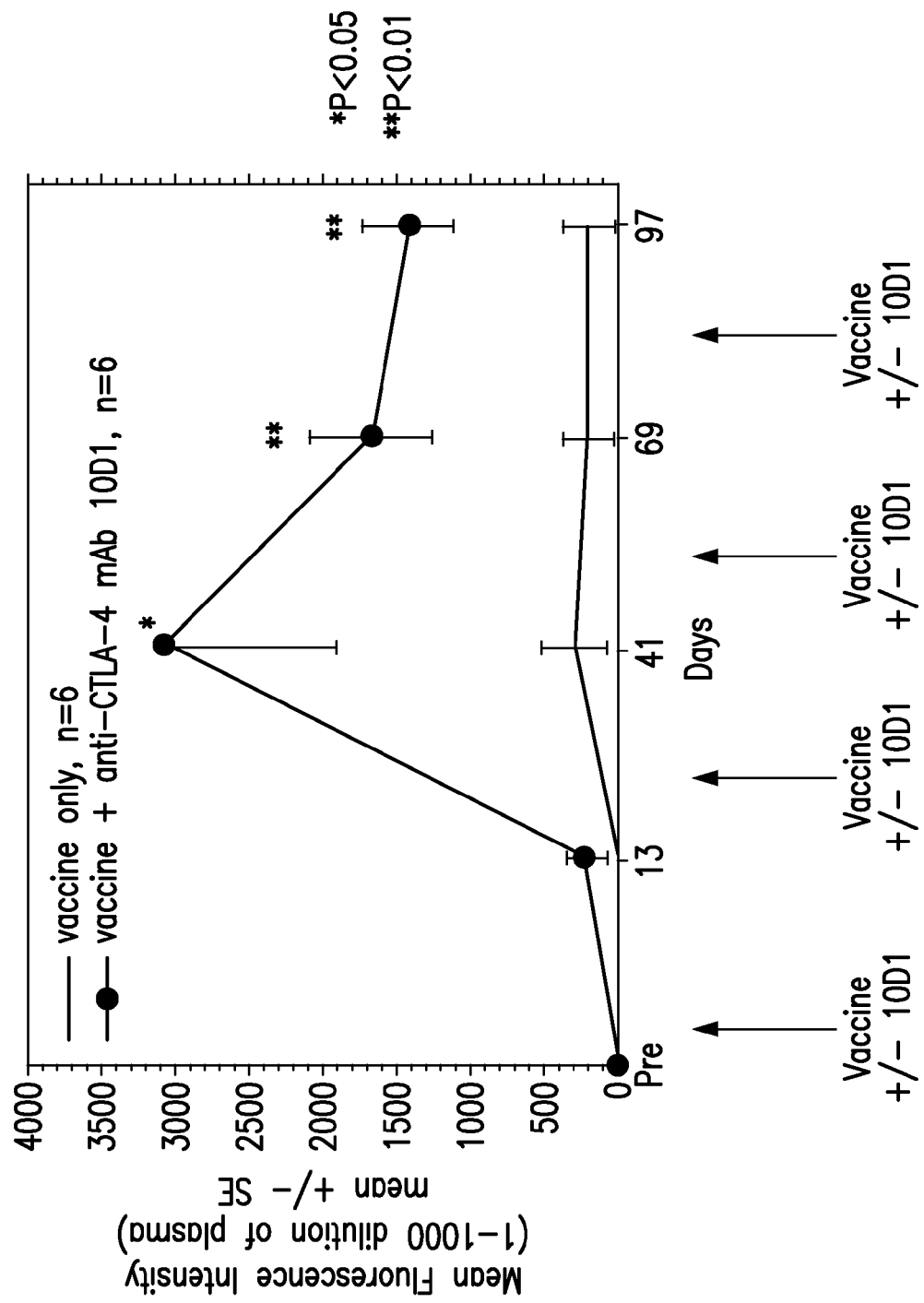

FIG. 20 shows the level of antibody responses to a melanoma cell vaccine in primates treated with either the vaccine alone (open circles) or with the vaccine in combination with the anti-CTLA4 antibody 10D1 (closed circles).

Figure 21:
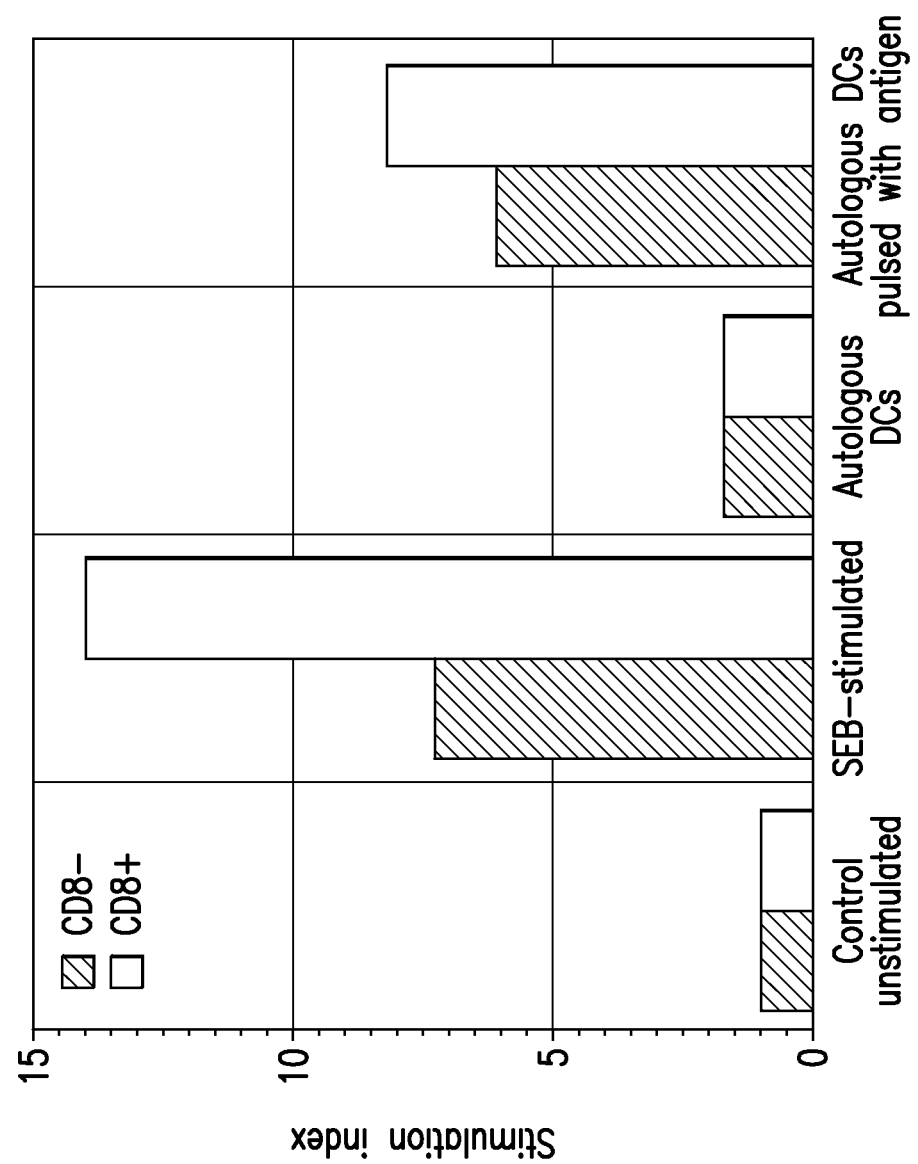

FIG. 21 shows antigen-specific T cell proliferation in a primate vaccinated with a melanoma cell vaccine in combination with the anti-CTLA4 antibody 10D1.

DETAILED DESCRIPTION

The present invention provides novel antibody-based therapies for treating and diagnosing diseases characterized by expression, particularly over-expression, or activation of, particularly overactivation, of human CTLA-4 and/or related molecules. Therapies of the invention employ human sequence antibodies, human sequence monoclonal antibodies, or antigen-binding portions thereof, which bind to an epitope present on human CTLA-4. These human sequence anti-CTLA-4 antibodies can act as functional antagonists (e.g., inhibiting the ability of CTLA-4 to bind ligand or to activate the cell, e.g., by inhibiting its ability to transmit a signal to the cell) or agonists (e.g., to simulate the effect of ligand).

The human sequence antibodies of the invention can be produced in a non-human transgenic animal, e.g., a transgenic mouse, capable of producing multiple isotypes of human (e.g., monoclonal or polyclonal) antibodies to human CTLA-4 IgG, IgA and/or IgE) by undergoing V-D-J recombination and isotype switching. Accordingly, various aspects of the invention include antibodies and antibody fragments, and pharmaceutical compositions thereof, as well as non-human transgenic animals, and B-cells and hybridomas for making such monoclonal antibodies. Methods of using the antibodies of the invention to detect a cell expressing human CTLA-4 or a related, cross-reactive growth factor receptor, or to inhibit growth, differentiation and/or motility of a cell expressing human CTLA-4, either in vitro or in vivo, are also encompassed by the invention.

Except when noted, the terms "patient" or "subject" are used interchangeably and refer to mammals such as human patients and non-human primates, as well as experimental animals such as rabbits, rats, and mice, and other animals.

The term "treating" includes the administration of the compounds or agents of the present invention to prevent or delay the onset of the symptoms, complications, or biochemical indicia of a disease, alleviating the symptoms or arresting or inhibiting further development of the disease, condition, or disorder (e.g., autoimmune disease). Treatment may be prophylactic (to prevent or delay the onset of the disease, or to prevent the manifestation of clinical or subclinical symptoms thereof) or therapeutic suppression or alleviation of symptoms after the manifestation of the disease.

In general, the phrase "well tolerated" refers to the absence of adverse changes in health status that occur as a result of the treatment and would affect treatment decisions.

The term "lymphocyte" as used herein has the normal meaning in the art, and refers to any of the mononuclear, nonphagocytic leukocytes, found in the blood, lymph, and lymphoid tissues, i.e., B and T lymphocytes.

The phrase "subpopulations of T lymphocytes" or "T cell subset(s)" refers to T lymphocytes or T cells characterized by the expression of particular cell surface markers (see Barclay, A. N. et al., (eds.), 1997, The Leukocyte Antigen Facts Book, 2nd. edition, Academic Press, London, United Kingdom). The term "stable" in reference to T cells refers to the fact that the frequency or percentage of a T cell subset does not change over the course or duration of the administration of an agent.

The terms "cytotoxic T lymphocyte-associated antigen-4," "CTLA-4," "CTLA4," "CTLA-4 antigen" and "CD152" (see, e.g., Murata (1999) Am. J. Pathol. 155:453-460) are used interchangeably, and include variants, isoforms, species homologs of human CTLA-4, and analogs having at least one common epitope with CTLA-4 (see, e.g., Balzano (1992) Int. J. Cancer Suppl. 7:28-32).

The complete cDNA sequence of human CTLA-4 has the Genbank accession number L15006. The region of amino acids 1-37 is the leader peptide; 38-161 is the extracellular V-like domain; 162-187 is the transmembrane domain; and 188-223 is the cytoplasmic domain. Variants of the nucleotide sequence have been reported, including a G to A transition at position 49, a C to T transition at position 272, and an A to G transition at position 439. The complete DNA sequence of mouse CTLA-4 has the EMBL accession number X05719 (Brunet et al. (1987) Nature 328:267-270). The region of amino acids 1-35 is the leader peptide.

The complete DNA sequence of human B7-1 (CD80) has the Genbank accession number X60958; the accession number for the mouse sequence is X60958; the accession number for the rat sequence is U05593. The complete cDNA sequence of human B7-2 (CD86) has the Genbank accession number L25259; the accession number for the mouse sequence is L25606.

The genes encoding CD28 have been extensively characterized. The chicken mRNA sequence has the Genbank accession number X67915. The rat mRNA sequence has the Genbank accession number X55288. The human mRNA sequence has the Genbank accession number J02988. The mouse mRNA sequence has the Genbank accession number M34536.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind CTLA-4. Examples of binding include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al. (1988) Science 242:423-426; and Huston et al. (1988) Proc. Natl. Acad. Sci. USA 85:5879-5883). Such single chain antibodies are included by reference to the term "antibody" Fragments can be prepared by recombinant techniques or enzymatic or chemical cleavage of intact antibodies.

A bispecific antibody has two different binding specificities, see. e.g., U.S. Pat. Nos. 5,922,845 and 5,837,243; Zeilder (1999) J. Immunol. 163:1246-1252; Somasundaram (1999) Hum. Antibodies 9:47-54; Keler (1997) Cancer Res. 57:4008-4014. For example, the invention provides bispecific antibodies having one binding site for a cell surface antigen, such as human CTLA-4, and a second binding site for an Fe receptor on the surface of an effector cell. The invention also provides multispecific antibodies, which have at least three binding sites. The term "bispecific antibodies" further includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (See, e.g., Holliger, P., et al., (1993) Proc. Natl. Acad. Sci. USA 90:6444-6448; Poljak, R. J., et al., (1994) Structure 2:1121-1123).

The term "human sequence antibody" includes antibodies having variable and constant regions (if present) derived from human germline immunoglobulin sequences. The human sequence antibodies of the invention may include amino acid residues not encoded by human germline immunoglobulin sequences (e.g., mutations introduced by random or site-specific mutagenesis in vitro or by somatic mutation in vivo). However, the term "human sequence antibody", as used herein, is not intended to include antibodies in which CDR sequences derived from the germline of another mammalian species, such as a mouse, have been grafted onto human framework sequences (i.e., humanized antibodies).

The terms "monoclonal antibody" or "monoclonal antibody composition" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "diclonal antibody" refers to a preparation of at least two antibodies to human CTLA-4. Typically, the different antibodies bind different epitopes.

The term "oligoclonal antibody" refers to a preparation of 3 to 100 different antibodies to human CTLA-4. Typically, the antibodies in such a preparation bind to a range of different epitopes.

The term "polyclonal antibody" refers to a preparation of more than 1 (two or more) different antibodies to human CTLA-4. Such a preparation includes antibodies binding to a range of different epitopes.

The invention provides human sequence antibodies to human CTLA-4 which block or antagonize signals transduced by the human CTLA-4 receptor. Some of these antibodies can bind to an epitope on human CTLA-4 so as to inhibit CTLA-4 from interacting with a human B7 counter-receptor. Because interaction of human CTLA-4 with human B7 transduces a signal leading to inactivation of T-cells bearing the human CTLA-4 receptor, antagonism of the interaction effectively induces, augments or prolongs the activation of T cells bearing the human CTLA-4 receptor, thereby prolonging or augmenting an immune response. A "blocking antibody" refers to an antibody that reduces the binding of soluble human CTLA-4 to cell-expressed human B7 ligand by at least 10%, 20%, 30%, 40%, 50%, 60%, 70%, 80%, 90%, 99% or 99.9% under conditions in which the ratio of antibody combining site to human CTLA-4 ligand binding site is greater than 1:1 and the concentration of antibody is greater than $10^{-8}$ M.

Other antibody preparations, sometimes referred to as multivalent preparations, bind to human CTLA-4 in such a manner as to crosslink multiple human CTLA-4 receptors on the same cell. Cross-linking of receptor has the same or similar effect to binding of human CTLA-4 to human B7. Thus, cross-linking of receptors effectively agonizes the human CTLA-4 response resulting in immunosuppression.

Cross-linking can also be accomplished by combining soluble divalent antibodies having different epitope specificities. These polyclonal antibody preparations comprise at least two pairs of heavy and light chains binding to different epitopes on human CTLA-4 such that an immunosuppressing signal can be transduced as a result of human CTLA-4 crosslinking.

The term "recombinant human antibody" includes all human sequence antibodies of the invention that are prepared, expressed, created or isolated by recombinant means, such as antibodies isolated from an animal (e.g., a mouse) that is transgenic for human immunoglobulin genes (described further in Section I, below); antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

A "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

The term "substantially pure" or "isolated" means an object species (e.g., an antibody of the invention) has been identified and separated and/or recovered from a component of its natural environment such that the object species is the predominant species present (i.e., on a molar basis it is more abundant than any other individual species in the composition); a "substantially pure" or "isolated" composition also means where the object species comprises at least about 50 percent (on a molar basis) of all macromolecular species present. A substantially pure or isolated composition can also comprise more than about 80 to 90 percent by weight of all macromolecular species present in the composition. An isolated object species (e.g., antibodies of the invention) can also be purified to essential homogeneity (contaminant species cannot be detected in the composition by conventional detection methods) wherein the composition consists essentially of derivatives of a single macromolecular species. An isolated antibody to human CTLA-4 can be substantially free of other antibodies that lack binding to human CTLA-4 and bind to a different antigen. An isolated antibody that specifically binds to an epitope, isoform or variant of human CTLA-4 may, however, have cross-reactivity to other related antigens, e.g., from other species (e.g., CTLA-4 species homologs). Moreover, an isolated antibody of the invention be substantially free of other cellular material (e.g., non-immunoglobulin associated proteins) and/or chemicals.

"Specific binding" refers to antibody binding to a predetermined antigen. The phrase "specifically (or selectively) binds" to an antibody refers to a binding reaction that is determinative of the presence of the protein in a heterogeneous population of proteins and other biologics. Typically, the antibody binds with an association constant ($K_a$) of at least about $1\times10^6$ M$^{-1}$ or $10^7$ M$^{-1}$, or about $10^8$M$^{-1}$ to $10^9$ M$^{-1}$, or about $10^{10}$ M$^{-1}$ to $10^{11}$ M$^{-1}$ or higher, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The phrase "specifically bind(s)" or "bind(s) specifically" when referring to a peptide refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions may require a binding moiety that is selected for its specificity for a particular target antigen. A variety of assay formats may be used to select ligands that are specifically reactive with a particular protein. For example, solid-phase ELISA immunoassays, immunoprecipitation, Biacore and Western blot are used to identify peptides that specifically react with CTLA-4. Typically a specific or selective reaction will be at least twice background signal or noise and more typically more than 10 times background.

The term "high affinity" for an IgG antibody refers to an equilibrium association constant ($K_a$) of at least about $10^7 M^{-1}$, at least about $10^8 M^{-1}$, at least about $10^9 M^{-1}$, at least about $10^{10} M^1$, at least about $10^{11} M^{-1}$, or at least about $10^{12} M^{-1}$ or greater, e.g., up to $10^{13} M^{-1}$ or $10^{14} M^{-1}$ or greater. However, "high affinity" binding can vary for other antibody isotypes.

The term "$K_a$", as used herein, is intended to refer to the equilibrium association constant of a particular antibody-antigen interaction. This constant has units of 1/M.

The term "$K_d$", as used herein, is intended to refer to the equilibrium dissociation constant of a particular antibody-antigen interaction. This constant has units of M.

The term "$k_a$", as used herein, is intended to refer to the kinetic association constant of a particular antibody-antigen interaction. This constant has units of 1/Ms The term "$k_d$", as used herein, is intended to refer to the kinetic dissociation constant of a particular antibody-antigen interaction. This constant has units of 1/s.

"Particular antibody-antigen interactions" refers to the experimental conditions under which the equilibrium and kinetic constants are measured.

"Isotype" refers to the antibody class (e.g., IgM or IgG1) that is encoded by heavy chain constant region genes.

"Isotype switching" refers to the phenomenon by which the class, or isotype, of an antibody changes from one Ig class to one of the other Ig classes.

"Nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ (δ-associated deletion), Alternative non-classical switching mechanisms, such as intertransgene and/or interchromosomal recombination, among others, may occur and effectuate isotype switching.

The term "switch sequence" refers to those DNA sequences responsible for switch recombination. A "switch donor" sequence, typically a p. switch region, are 5' (i.e., upstream) of the construct region to be deleted during the switch recombination. The "switch acceptor" region are between the construct region to be deleted and the replacement constant region (e.g., γ, ε, etc.). As there is no specific site where recombination always occurs, the final gene sequence is not typically predictable from the construct.

"Glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the non-human transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus has at least one recombined heptamer/nonamer homology element.

The term "unrearranged" or "germline configuration" in reference to a V segment refers to the configuration wherein the V segment is not recombined so as to be immediately adjacent to a D or J segment.

The term "nucleic acid" is intended to include DNA molecules and RNA molecules. A nucleic acid can be single-stranded or double-stranded.

The term "isolated nucleic acid" in reference to nucleic acids encoding antibodies or antibody portions (e.g., VH, VL, CDR3) that bind to CTLA-4, is intended to refer to a nucleic acid in which the nucleotide sequences encoding the antibody or antibody portion are free of other nucleotide sequences encoding antibodies or antibody portions that bind antigens other than CTLA-4, which other sequences may naturally flank the nucleic acid in human genomic DNA. SEQ ID NOS: 4-23 comprise the nucleotide and amino acid sequences comprising the heavy chain (VH) and light chain (VL) variable regions of the 10D1, 4B6 and 1E2 human anti-CTLA-4 monoclonal antibodies of the invention.

The term "substantially identical," in the context of two nucleic acids or polypeptides refers to two or more sequences or subsequences that have at least about 80%, about 90, about 95% or higher nucleotide or amino acid residue identity, when compared and aligned for maximum correspondence, as measured using the following sequence comparison method and/or by visual inspection. For example, the invention provides nucleic acids having sequences that are substantially identical to SEQ ID NO:1, SEQ ID NO:2. Such "substantially identical" sequences are typically considered to be homologous. The "substantial identity" can exist over a region of sequence that is at least about 50 residues in length, over a region of at least about 100 residues, or over a region at least about 150 residues, or over the full length of the two sequences to be compared. As described below, any two antibody sequences can only be aligned in one way, by using the numbering scheme in Kabat. Therefore, for antibodies, percent identity has a unique and well-defined meaning.

Amino acids from the variable regions of the mature heavy and light chains of immunoglobulins are designated Hx and Lx respectively, where x is a number designating the position of an amino acid according to the scheme of Kabat, *Sequences of Proteins of Immunological Interest* (National Institutes of Health, Bethesda, Md., 1987 and 1991). Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Likewise, nucleic acids encoding antibody chains are aligned when the amino acid sequences encoded by the respective nucleic acids are aligned according to the Kabat numbering convention.

The phrase "selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least at about 10 times background. In one embodiment, a nucleic acid can be determined to be within the scope of the invention (e.g., is substantially identical to SEQ ID NO:1 or SEQ ID NO:2) by its ability to hybridize under stringent conditions to a nucleic acid otherwise determined to be within the scope of the invention (such as the exemplary sequences described herein).

The phrase "stringent hybridization conditions" refers to conditions under which a probe will hybridize to its target subsequence, typically in a complex mixture of nucleic acid, but not to other sequences in significant amounts (a positive signal (e.g., identification of a nucleic acid of the invention) is about 10 times background hybridization). Stringent conditions are sequence-dependent and will be different in different circumstances. Longer sequences hybridize specifically at higher temperatures. An extensive guide to the hybridization of nucleic acids is found An extensive guide to the hybridization of nucleic acids is found in e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at T, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide as described in Sambrook (cited below). For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. For selective or specific hybridization, a positive signal (e.g., identification of a nucleic acid of the invention) is about 10 times background hybridization. Stringent hybridization conditions that are used to identify nucleic acids within the scope of the invention include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. In the present invention, genomic DNA or cDNA comprising nucleic acids of the invention can be identified in standard Southern blots under stringent conditions using the nucleic acid sequences disclosed here. Additional stringent conditions for such hybridizations (to identify nucleic acids within the scope of the invention) are those which include a hybridization in a buffer of 40% formamide, 1 M NaCl, 1% SDS at 37° C.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

The nucleic acids of the invention be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. see, e.g., Sambrook, Tijssen and Ausubel. The nucleic acid sequences of the invention and other nucleic acids used to practice this invention, whether RNA, cDNA, genomic DNA, or hybrids thereof, may be isolated from a variety of sources, genetically engineered, amplified, and/or expressed recombinantly. Any recombinant expression system can be used, including, in addition to bacterial, e.g., yeast, insect or mammalian systems. Alternatively, these nucleic acids can be chemically synthesized in vitro. Techniques for the manipulation of nucleic acids, such as, e.g., subcloning into expression vectors, labeling probes, sequencing, and hybridization are well described in the scientific and patent literature, see, e.g., Sambrook, Tijssen and Ausubel. Nucleic acids can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immunofluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "minilocus transgene" refers to a transgene that comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptides of the invention can be made detectable, e.g., by incorporating a radiolabel into the peptide, and used to detect antibodies specifically reactive with the peptide).

The term "sorting" in the context of cells as used herein to refers to both physical sorting of the cells, as can be accomplished using, e.g., a fluorescence activated cell sorter, as well as to analysis of cells based on expression of cell surface markers, e.g., FACS analysis in the absence of sorting.

The phrase "immune cell response" refers to the response of immune system cells to external or internal stimuli (e.g., antigen, cytokines, chemokines, and other cells) producing biochemical changes in the immune cells that result in immune cell migration, killing of target cells, phagocytosis, production of antibodies, other soluble effectors of the immune response, and the like.

The terms "T lymphocyte response" and "T lymphocyte activity" are used here interchangeably to refer to the component of immune response dependent on T lymphocytes (i.e., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

The term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

Components of an immune response may be detected in vitro by various methods that are well known to those of ordinary skill in the art. For example, (1) cytotoxic T lymphocytes can be incubated with radioactively labeled target cells and the lysis of these target cells detected by the release of radioactivity, (2) helper T lymphocytes can be incubated with antigens and antigen presenting cells and the synthesis and secretion of cytokines measured by standard methods (Windhagen A; et al., 1995, Immunity 2(4): 373-80), (3) antigen presenting cells can be incubated with whole protein antigen and the presentation of that antigen on MHC detected by either T lymphocyte activation assays or biophysical methods (Harding et al., 1989, Proc. Natl. Acad. Sci., 86: 4230-4), (4) mast cells can be incubated with reagents that cross-link their Fc-epsilon receptors and histamine release measured by enzyme immunoassay (Siraganian, et al., 1983, TIPS 4: 432-437).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., 1988, Blood 72: 1310-5); (3) the proliferation of peripheral blood mononuclear cells in response to mitogens or mixed lymphocyte reaction can be measured using $^3H$-thymidine; (4) the phagocitic capacity of granulocytes, macrophages, and other phagocytes in PBMCs can be measured by placing PMBCs in wells together with labeled particles (Peters et al., 1988); and (5) the differentation of immune system cells can be measured by labeling PBMCs with antibodies to CD molecules such as CD4 and CD8 and measuring the fraction of the PBMCs expressing these markers.

As used herein, the phrase "signal transduction pathway" or "signal transduction event" refers to at least one biochemical reaction, but more commonly a series of biochemical reactions, which result from interaction of a cell with a stimulatory compound or agent. Thus, the interaction of a stimulatory compound with a cell generates a "signal" that is transmitted through the signal transduction pathway, ultimately resulting in a cellular response, e.g., an immune response described above.

A signal transduction pathway refers to the biochemical relationship between a variety of signal transduction molecules that play a role in the transmission of a signal from one portion of a cell to another portion of a cell. Signal transduction molecules of the present invention include, for example, MAb 147.1 of the invention. As used herein, the phrase "cell surface receptor" includes molecules and complexes of molecules capable of receiving a signal and the transmission of such a signal across the plasma membrane of a cell. An example of a "cell surface receptor" of the present invention is the T cell receptor (TCR) or the B7 ligands of CTLA-4.

A signal transduction pathway in a cell can be initiated by interaction of a cell with a stimulator that is inside or outside of the cell. If an exterior (i.e., outside of the cell) stimulator (e.g., an MHC-antigen complex on an antigen presenting cell) interacts with a cell surface receptor (e.g., a T cell receptor), a signal transduction pathway can transmit a signal across the cell's membrane, through the cytoplasm of the cell, and in some instances into the nucleus. If an interior (e.g., inside the cell) stimulator interacts with an intracellular signal transduction molecule, a signal transduction pathway can result in transmission of a signal through the cell's cytoplasm, and in some instances into the cell's nucleus.

Signal transduction can occur through, e.g., the phosphorylation of a molecule; non-covalent allosteric interactions; complexing of molecules; the conformational change of a molecule; calcium release; inositol phosphate production; proteolytic cleavage; cyclic nucleotide production and diacylglyceride production. Typically, signal transduction occurs through phosphorylating a signal transduction molecule.

The term "nonspecific T cell activation" refers to the stimulation of T cells independent of their antigenic specificity.

Production of Human Antibodies to CTLA-4

The monoclonal antibodies (mAbs) and the human sequence antibodies of the invention can be produced by a variety of techniques, including conventional monoclonal antibody methodology e.g., the standard somatic cell hybridization technique of Kohler and Milstein, *Nature* 256: 495 (1975). Any technique for producing monoclonal antibody can be employed e.g., viral or oncogenic transformation of B lymphocytes. One animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known (see, e.g., Harlow and Lane (1988), *Antibodies, A Laboratory Manual*, Cold Spring Harbor Laboratory Press, Cold Spring Harbor N.Y.).

Human monoclonal antibodies and human sequence antibodies directed against human CTLA-4 can be generated using transgenic mice carrying a human immune system rather than the mouse system. These transgenic mice, also referred to herein as "HuMAb-Mouse™", contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368(6474): 856-859 and U.S. Pat. No. 5,770,429). Accordingly, the mice exhibit reduced expression of mouse IgM or K, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci.* 764:536-546). The preparation of transgenic mice is described in detail Section II below and in Taylor, L. et al., (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al., (1994) *J. Immunol.* 152:2912-2920; Lonberg et al., (1994) *Nature* 368(6474): 856-859; Lonberg, N. (1994) *Handbook of Experimental Pharmacology* 113:49-101; Taylor, L. et al., (1994) *International Immunology* 6: 579-591; Lonberg, N. and Huszar, D. (1995) Intern. Rev. Immunol, Vol. 13: 65-93; Harding, F. and Lonberg, N. (1995) *Ann. N.Y. Acad. Sci.* 764:536-546; Fishwild, D. et al. (1996) *Nature Biotechnology* 14: 845-851. See further, U.S. Pat. Nos. 5,625,126 and 5,770,429, both to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992. Alternatively, the CMD and HCo12 transgenes, described in Examples 1 and 2, below, can be used to generate human anti-CTLA-4 antibodies.

Detailed procedures to generate fully human monoclonal antibodies to CTLA-4 are described in the Examples below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-CTLA-4 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes.

To purify human anti-CTLA-4 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Fluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected human anti-CTLA-4 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CTLA-4 coated-ELISA plates as described above. Biotinylated MAb binding can be detected with a strep-avidin-alkaline phosphatase probe.

To determine the isotype of purified antibodies, isotype ELISAs can be performed. Wells of microtiter plates can be coated with 1 µg/ml of anti-human IgG overnight at 4° C. After blocking with 1% BSA, the plates are reacted with 1 µg/ml or less of monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To demonstrate binding of monoclonal antibodies to live cells expressing the CTLA-4, flow cytometry can be used. Briefly, cell lines expressing CTLA-4 (grown under standard growth conditions) are mixed with various concentrations of monoclonal antibodies in PBS containing 0.1% BSA and 10% fetal calf serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CTLA-4 human IgGs can be further tested for reactivity with CTLA-4 antigen by Western blotting. Briefly, cell extracts from cells expressing CTLA-4 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Production of Transgenic Non-Human Animals that Generate Human Monoclonal Anti-CTLA-4 Antibodies The present invention also provides transgenic non-human animals, e.g., a transgenic mice, which are capable of expressing human monoclonal antibodies that specifically bind to CTLA-4. High affinity human sequence antibodies are also provided. Some transgenic non-human animals, e.g., the transgenic mice, have a genome comprising a human heavy chain transgene and a light chain transgene. Some transgenic non-human animals are immunized with a purified or enriched preparation of CTLA-4 antigen and/or cells expressing CTLA-4. Some transgenic non-human animals are capable of producing multiple isotypes of human monoclonal antibodies to CTLA-4 (e.g., IgG, IgA and/or IgE) by undergoing V-D-J recombination and isotype switching. Isotype switching may occur by, e.g., classical or non-classical isotype switching.

The design of a transgenic non-human animal that responds to foreign antigen stimulation with a heterologous antibody repertoire, requires that the heterologous immunoglobulin transgenes contained within the transgenic animal function correctly throughout the pathway of B-cell development. In some mice, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in transgenic animal in which the endogenous immunoglobulin loci of the transgenic animals are functionally disrupted, the transgene need not activate allelic exclusion. Further, in transgenic animals in which the transgene comprises a functionally rearranged heavy and/or light chain immunoglobulin gene, the second criteria of functional gene rearrangement is unnecessary, at least for that transgene which is already rearranged. For background on molecular immunology, See, e.g., *Fundamental Immunology*, 4th edition (1998), Paul, William E., ed. Lippencott-Raven Press, N.Y.

Some transgenic non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one CH gene. In addition, the heavy chain transgene can contain functional isotype switch sequences, which are capable of supporting isotype switching of a heterologous transgene encoding multiple CH genes in the B-cells of the transgenic animal. Such switch sequences can be those which occur naturally in the germline immunoglobulin locus from the species that serves as the source of the transgene CH genes, or such switch sequences can be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences can be isolated and cloned by conventional cloning methods, or can be synthesized de novo from overlapping synthetic oligonucleotides designed on the basis of published sequence information relating to immunoglobulin switch region sequences (Mills et al., *Nucl. Acids Res.* 15:7305-7316 (1991); Sideras et al., *Intl. Immunol.* 1:631-642 (1989).

For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to CTLA-4 antigen.

Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. The transgene may comprise a minilocus.

Some transgenic animals used to generate human antibodies to CTLA-4 contain at least one, typically 2-10, and sometimes 25-50 or more copies of the transgene described in Example 37 of U.S. Pat. No. 5,770,429, or the transgene described in Example 2 below (e.g., HCo12), at least one copy of a light chain transgene described in Examples 38 of U.S. Pat. No. 5,770,429, two copies of the Cmu deletion described in Example 1 below, and two copies of the Jkappa deletion described in Example 9 of U.S. Pat. No. 5,770,429. The resultant animals are injected with antigens and used for production of human monoclonal antibodies against these antigens.

Some transgenic animals exhibit immunoglobulin production with a significant repertoire, ideally substantially similar to that of a native mouse. Thus, for example, animals in which the endogenous Ig genes have been inactivated, the total immunoglobulin levels range from about 0.1 to about 10 mg/ml of serum.

The immunoglobulins expressed by the transgenic mice typically recognize about one-half or more of highly antigenic proteins, e.g., *staphylococcus* protein A. Typically, the immunoglobulins exhibit an association constant for preselected antigens of at least about $10^7 M^{-1}$, $10^8 M^{-1}$, $10^9 M^{-1}$, $10^{10} M^{-1}$, $10^{11} M^{-1}$, $10^{12} M^{-1}$, $10^{13} M^{-1}$, or greater.

The transgenic mice of the present invention can be immunized with a purified or enriched preparation of human CTLA-4 antigen (or antigenic fragment thereof) and/or cells expressing human CTLA-4 as described previously. The mice produce B cells that undergo class-switching via intratransgene switch recombination (cis-switching) and express immunoglobulins reactive with CTLA-4. The immunoglobulins can be human sequence antibodies, wherein the heavy and light chain polypeptides are encoded by human transgene sequences, which may include sequences derived by somatic mutation and V region recombinatorial joints, as well as germline-encoded sequences; these human sequence immunoglobulins can be referred to as being substantially identical to a polypeptide sequence encoded by a human VL or VH gene segment and a human JL or JH segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies frequently have some variable region sequences (and less frequently constant region sequences) which are not encoded by human V, D, or J gene segments as found in the human transgene(s) in the germline of the mice. Typically, such non-germline sequences (or individual nucleotide positions) cluster in or near CDRs, or in regions where somatic mutations are known to cluster.

The human sequence antibodies which bind to the predetermined antigen can result from isotype switching, such that human antibodies comprising a human sequence γ chain (such as γ1, γ2, γ3, or γ4) and a human sequence light chain (such as kappa or lambda) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. Some high affinity human sequence antibodies have equilibrium association constants of at least about $1\times10^7$ $M^{-1}$, or at least about $1\times10^8$ $M^{-1}$, or more than about $1\times10^9$ $M^{-1}$, or $5\times10^9$ $M^{-1}$ to $1\times10^{11}$ $M^{-1}$ or greater.

Another aspect of the invention pertains to the B cells from such mice which can be used to generate hybridomas expressing human monoclonal antibodies which bind with high affinity (e.g., having association constant of greater than $10^7 M^{-1}$) to CTLA-4. These hybridomas are used to generate a composition comprising an immunoglobulin having an association constant (Ka) of at least $10^7$ $M^{-1}$ for binding CTLA-4. Such immunoglobulin contains a human sequence light chain composed of a light chain variable region having a polypeptide sequence which is substantially identical to a polypeptide sequence encoded by a human Vκ or Vλ gene segment and a human Jκ or Jλ segment, and a light chain constant region having a polypeptide sequence which is substantially identical to a polypeptide sequence encoded by a human Cκ or Cλ gene segment. It also contains a human sequence heavy chain composed of a heavy chain variable region having a polypeptide sequence which is substantially identical to a polypeptide sequence encoded by a human VH gene segment, optionally a D region, and a human JH segment, and a constant region having a polypeptide sequence which is substantially identical to a polypeptide sequence encoded by a human CH gene segment.

The invention also provides human monoclonal antibodies and human sequence antibodies to human CTLA-4 derivatized or linked to another functional molecule, e.g., another peptide or protein (e.g., a cytokine, a cytotoxic agent, an immune stimulatory or inhibitory agent, a Fab' fragment, and the like, as discussed above) to generate a bispecific or multispecific molecule which binds to multiple binding sites or target epitopes. For example, an antibody or antigen-binding portion of the invention can be functionally linked (e.g., by chemical coupling, genetic fusion, noncovalent association or otherwise) to one or more other binding molecules, such as another antibody, antibody fragment, peptide or binding mimetic.

Accordingly, the present invention includes bispecific and multispecific composition comprising at least one human sequence antibody or antigen binding fragment with a first binding specificity for human CTLA-4 and a second binding specificity for a second target epitope. The second target epitope can be an Fc receptor, e.g., human FcγRI or a human Fcγ receptor. Therefore, the invention includes bispecific and multispecific molecules capable of binding both to FcγR1, FcγR or FcεR. expressing effector cells (e.g., monocytes, macrophages or polymorphonuclear cells (PMNs)), and to target cells expressing human CTLA-4. These multispecific (e.g., bispecific or multispecific) molecules target human CTLA-4 expressing cells to effector cells, and trigger Fc receptor-mediated effector cell activities, such as phagocytosis of a human CTLA-4-expressing cells, antibody dependent cell-mediated cytotoxicity (ADCC), cytokine release, or generation of superoxide anion.

The bispecific and multispecific molecules of the invention can comprise a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in, e.g., Ladner et al. U.S. Pat. No. 4,946,778. Bispecific and multispecific molecules of the invention can comprise a binding specificity for an FcγR or an FcγR present on the surface of an effector cell, and a second binding specificity for a target cell antigen, e.g., human CTLA-4.

The binding specificity for an Fc receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRIII (CD16). For example, the Fcγ receptor can be a human high affinity FcγRI. The human FcγRI is a 72 kDa molecule, which shows high affinity for monomeric IgG ($10^8$ to $10^9$ M$^{-1}$).

The production and characterization of these preferred monoclonal antibodies are described by Fanger et al. in PCT application WO 88/00052 and in U.S. Pat. No. 4,954,617. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are MAb 22, MAb 32, MAb 44, MAb 62 and MAb 197. The hybridoma producing MAb 32 is available from the American Type Culture Collection, ATCC Accession No. HB9469. Anti-FcγRI MAb 22, F(ab')$_2$ fragments of MAb 22, and can be obtained from Medarex, Inc. (Annandale, N.J.). In other embodiments, the anti-Fcγ receptor antibody is a humanized form of monoclonal antibody 22 (H22). The production and characterization of the H22 antibody is described in Graziano (1995) J. Immunol. 155:4996-5002 and PCT/US93/10384, The H22 antibody producing cell line was deposited at the American Type Culture Collection on Nov. 4, 1992 under the designation HA022CL1 and has the accession no. CRL 11177.

The binding specificity for an Fc receptor can also be provided by an antibody that binds to a human IgA receptor, e.g., an Fc-alpha receptor (FcαR (CD89)). Preferably, the antibody binds to a human IgA receptor at a site that is not blocked by endogenous IgA. The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5\times 10^7$ M$^{-1}$) for both IgA1 and IgA2, which is increased upon exposure to cytokines such as G-CSF or GM-CSF (Morton (1996) Critical Reviews in Immunology 16:423-440). Four FcαRI-specific monoclonal antibodies, identified as A3, A59, A62 and A77, which bind FcαRI outside the IgA ligand binding domain, have been described by, e.g., Monteiro (1992) J. Immunol. 148:1764.

Bispecific and multispecific molecules of the invention can further comprise a binding specificity which recognizes, e.g., binds to, a target cell antigen, e.g. human CTLA-4. The binding specificity is provided by a human sequence antibody or a human monoclonal antibody of the present invention.

An "effector cell specific antibody" as used herein refers to an antibody or functional antibody fragment that binds the Fe receptor of effector cells. Preferred antibodies for use in the subject invention bind the Fe receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. An effector cell can also phagocytose a target antigen, target cell, or microorganism.

The expression of a particular FcR on an effector cell can be regulated by humoral factors such as cytokines. For example, expression of FcγRI has been found to be up-regulated by interferon gamma (IFN-γ). This enhanced expression increases cytotoxic activity (including, e.g., phagocytosis) by FcγRI-bearing cells against target cells.

"Target cell" shall mean any undesirable cell in a subject (e.g., a human or animal) that can be targeted by a composition (e.g., a human sequence antibody or a human monoclonal antibody of the invention, a bispecific or a multispecific molecule of the invention). The target cell can be a cell expressing or overexpressing human CTLA-4. Cells expressing human CTLA-4 can include tumor cells, e.g. lymphomas.

In addition to human sequence antibodies and human monoclonal antibodies of the invention, other antibodies can be also be employed in the bispecific or multispecific molecules of the invention, including, e.g., murine, chimeric and humanized monoclonal antibodies.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See, e.g., Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better (1988) Science 240:1041-1043; Liu (1987) PNAS 84:3439-3443; Liu (1987) J. Immunol. 139:3521-3526; Sun (1987) PNAS 84:214-218; Nishimura (1987) Cane. Res. 47:999-1005; Wood (1985) Nature 314:446-449; Shaw (1988) J. Natl. Cancer Inst. 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison (1985) *Science* 229:1202-1207 and by Oi (1986) *BioTechniques* 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones (1986) Nature 321:552-525; Verhoeyan et al, 1988 Science 239:1534; and Beidler (1988) J. Immunol. 141:4053-4060.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fe receptor. An antibody can be humanized by any method, which is capable of replacing at least a portion of a CDR of a human antibody with a CDR derived from a non-human antibody. Winter describes a method which may be used to prepare the humanized antibodies of the present invention, see UK Patent Application GB 2188638A, filed on Mar. 26, 1987. The human CDRs may be replaced with non-human CDRs using oligonucleotide site-directed mutagenesis as described in, e.g., WO 94/10332 entitled, *Humanized Antibodies to Fc Receptors for Immunoglobulin G on Human Mononuclear Phagocytes.*

Chimeric and humanized antibodies in which specific amino acids have been substituted, deleted or added are also within the scope of the invention. For example, humanized antibodies can have amino acid substitutions in the framework region, such as to improve binding to the antigen. In a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

Bispecific and multispecific molecules of the invention can further include a third binding specificity, in addition to an anti-Fc binding specificity and an anti-human CTLA-4 binding specificity. The third binding specificity can be an anti-enhancement factor (BF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell via, e.g., CD2, CD3, CD8, CD28, CD4, CD40, ICAM-1 or other immune cell molecules that are involved in an increased immune response against the target cell.

Bispecific and multispecific molecules of the present invention can be made using chemical techniques (see, e.g., Kranz (1981) *Proc. Natl. Acad. Sci. USA* 78:5807), "polydoma" techniques (see, e.g., U.S. Pat. No. 4,474,893), or recombinant DNA techniques. Bispecific and multispecific molecules of the present invention can also be prepared by conjugating the constituent binding specificities, e.g., the anti-FcR and anti-human CTLA-4 binding specificities, using methods known in the art and as described herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), N-succinimidyl-3-(2-pyridyldithio)propionate (SPDP), and sulfosuccinimidyl 4-(N-maleimidomethyl)cyclohexane-1-carboxylate (sulfo-SMCC) (see, e.g., Karpovsky (1984) J. Exp. Med. 160:1686; Liu (1985) Proc. Natl. Acad. Sci. USA 82:8648). Other methods include those described by Paulus (Behring Ins. Mitt. (1985) No. 78, 118-132; Brennan (1985) Science 229:81-83), Glennie (1987) J. Immunol. 139: 2367-2375). Other conjugating agents are SATA and sulfo-SMCC, both available from Pierce Chemical Co. (Rockford, Ill.).

When the binding specificities are antibodies (e.g., two humanized antibodies), they can be conjugated via sulfhydryl bonding of the C-terminus hinge regions of the two heavy chains. The hinge region can be modified to contain an odd number of sulfhydryl residues, e.g., one, prior to conjugation.

Alternatively, both binding specificities can be encoded in the same vector and expressed and assembled in the same host cell. This method is particularly useful where the bispecific and multispecific molecule is a MAb×MAb, MAb×Fab, Fab×F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific and multispecific molecules to their specific targets can be confirmed by enzyme-linked immunosorbent assay (ELISA), a radioimmunoassay (RIA), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Also included in the invention are modified antibodies. The term "modified antibody" includes antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody.

The antibody conjugates of the invention can be used to modify a given biological response or create a biological response (e.g., to recruit effector cells). The drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-alpha; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et cd. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Pharmaceutical Compositions

The invention provides pharmaceutical compositions comprising one or a combination of human monoclonal antibodies and/or human sequence antibodies (intact or binding fragments) formulated together with a pharmaceutically acceptable carrier. Some compositions include a combination of multiple (e.g., two or more) isolated human antibodies and/or human sequence antibody or antigen-binding portions thereof of the invention. In some compositions, each of the antibodies or antigen-binding portions thereof of the composition is a monoclonal antibody or a human sequence antibody that binds to a distinct, pre-selected epitope of human CTLA-4.

A. Effective Dosages

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the compounds of the invention employed in the pharmaceutical composition at levels lower than that required to achieve the desired therapeutic effect and gradually increase the dosage until the desired effect is achieved. In general, a suitable daily dose of a compositions of the invention is that amount of the compound which is the lowest dose effective to produce a therapeutic effect. Such an effective dose generally depends upon the factors described above. It is preferred that administration be intravenous, intramuscular, intraperitoneal, or subcutaneous, or administered proximal to the site of the target. If desired, the effective daily dose of a therapeutic compositions can be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Effective doses of the compositions of the present invention, for the treatment of immune-related conditions and diseases described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy.

For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to CTLA-4 in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 μg to 10 mg, or 30-300 μg DNA per patient. Doses for infectious viral vectors vary from 10-100, or more, virions per dose.

Some human sequence antibodies and human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, See, e.g., U.S. Pat. Nos. 4,522,811; 5,374,548; and 5,399,331. The liposomes may comprise one or more moieties which are selectively transported into specific cells or organs, thus enhance targeted drug delivery (See, e.g., V. V. Ranade (1989) *J. Clin. Pharmacal.* 29:685). Exemplary targeting moieties include folate or biotin (See, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al., (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); See also K. Keinanen; M. L. Laukkanen (1994) FEBS Lett. 346:123; J. J. Killion; I. J. Fidler (1994) *Immunomethods* 4:273. In some methods, the therapeutic compounds of the invention are formulated in liposomes; in a more preferred embodiment, the liposomes include a targeting moiety. In some methods, the therapeutic compounds in the liposomes are delivered by bolus injection to a site proximal to the tumor or infection. The composition should be fluid to the extent that easy syringability exists. It should be stable under the conditions of manufacture and storage and should be preserved against the contaminating action of microorganisms such as bacteria and fungi.

For therapeutic applications, the pharmaceutical compositions are administered to a patient suffering from established disease in an amount sufficient to arrest or inhibit further development or reverse or eliminate, the disease, its symptoms or biochemical markers. For prophylactic applications, the pharmaceutical compositions are administered to a patient susceptible or at risk of a disease in an amount sufficient to delay, inhibit or prevent development of the disease, its symptoms and biochemical markers. An amount adequate to accomplish this is defined as a "therapeutically-" or "prophylactically-effective dose." Dosage depends on the disease being treated, the subject's size, the severity of the subject's symptoms, and the particular composition or route of administration selected. Specifically, in treatment of tumors, a "therapeutically effective dosage" can inhibit tumor growth by at least about 20%, or at least about 40%, or at least about 60%, or at least about 80% relative to untreated subjects. The ability of a compound to inhibit cancer can be evaluated in an animal model system predictive of efficacy in human tumors. Alternatively, this property of a composition can be evaluated by examining the ability of the compound to inhibit by conventional assays in vitro. A therapeutically effective amount of a therapeutic compound can decrease tumor size, or otherwise ameliorate symptoms in a subject.

The composition should be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

B. Routes of Administration

Pharmaceutical compositions of the invention also can be administered in combination therapy, i.e., combined with other agents. For example, in treatment of cancer, the combination therapy can include a composition of the present invention with at least one anti-tumor agent or other conventional therapy, such as radiation treatment.

Pharmaceutically acceptable carriers includes solvents, dispersion media, coatings, antibacterial and antifungal agents, isotonic and absorption delaying agents, and the like that are physiologically compatible. The carrier can be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (See, e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., *Sustained and Controlled Release Drug Delivery Systems*, J. R. Robinson, ed., Marcel Dekker, Inc., New York, 1978. Pharmaceutical compositions are preferably manufactured under GMP conditions.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile, substantially isotonic, and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Therapeutic compositions can also be administered with medical devices known in the art. For example, in a preferred embodiment, a therapeutic composition of the invention can be administered with a needleless hypodermic injection device, such as the devices disclosed in, e.g., U.S. Pat. No. 5,399,163, 5,383,851, 5,312,335, 5,064,413, 4,941,880, 4,790,824, or 4,596,556. Examples of implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known.

C. Formulation

For the therapeutic compositions, formulations of the present invention include those suitable for oral, nasal, topical (including buccal and sublingual), rectal, vaginal and/or parenteral administration. The formulations can conveniently be presented in unit dosage form and may be prepared by any methods known in the art of pharmacy. The amount of active ingredient which can be combined with a carrier material to produce a single dosage form vary depending upon the subject being treated, and the particular mode of administration. The amount of active ingredient which can be combined with a carrier material to produce a single dosage form generally be that amount of the composition which produces a therapeutic effect. Generally, out of one hundred percent, this amount range from about 0.01 percent to about ninety-nine percent of active ingredient, from about 0.1 percent to about 70 percent, or from about 1 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (or 0.1 to 90%) of active ingredient in combination with a pharmaceutically acceptable carrier.

The pharmaceutical compositions are generally formulated as sterile, substantially isotonic and in full compliance with all Good Manufacturing Practice (GMP) regulations of the U.S. Food and Drug Administration.

Methods and Uses of the Invention

A. Methods

The compositions (e.g., human sequence antibodies and human monoclonal antibodies to human CTLA-4 and derivatives/conjugates thereof) of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. The term "subject" includes human and non-human animals. Non-human animals includes all vertebrates, e.g., mammals and non-mammals, such as non-human primates, sheep, dog, cow, chickens, amphibians, and reptiles. The methods are particularly suitable for treating human patients having a disorder that can be treated by augmenting or reducing the T-cell mediated immune response.

When antibodies to CTLA-4 are administered together with another agent, the two can be administered in either order or simultaneously. The methods can be used to treat any kind of cancer including melanoma, colon cancer, prostate cancer, and renal cancer.

For example, latex microspheres coated with anti-CTLA-4 (to increase the valency of the antibody) can inhibit T cell proliferation and activation. Agents having the same antibody combining site may act as a CTLA-4 antagonist when presented as an Fab or a soluble IgG, and a CTLA-4 agonist when highly cross-linked. Thus multivalent forms of anti-CTLA-4 antibodies are useful therapeutic agents for down-modulating immune responses.

In addition to linking to latex microspheres or other insoluble particles, the antibodies can be cross-linked to each other or genetically engineered to form multimers. Cross-linking can be by direct chemical linkage, or by indirect linkage such as an antibody-biotin-avidin complex. Cross-linking can be covalent, where chemical linking groups are employed, or non-covalent, where protein-protein or other protein-ligand interactions are employed. Genetic engineering approaches for linking include, e.g., the re-expression of the variable regions of high-affinity IgG antibodies in IgM expression vectors or any protein moiety (e.g., polylysine, and the like). Converting a high affinity IgG antibody to an IgM antibody can create a decavalent complex with very high avidity. $IgA_2$ expression vectors may also be used to produce multivalent antibody complexes. $IgA_2$ can form polymers together with J chain and secretory component. $IgA_2$ may have the added advantage that it can be additionally crosslinked by the IgA receptor CD89, which is expressed on neutrophils, macrophages, and monocytes.

Agonism can also be obtained using some preparations of polyclonal antibodies to CTLA-4 comprising antibodies to at least two non-overlapping epitopes on CTLA-4. One antibody in such a preparation containing two binding sites can bind to two molecules of CTLA-4 to form a small cluster. A second antibody possessing different binding sites can then link (aggregate) these small clusters to form large clusters, thereby forming a complex of CTLA-4 (on the cell surface) that can transduce a signal to the T cell to inhibit, reduce or prevent activation of the T-cell bearing (expressing) CTLA-4. Thus, some preparations of polyclonal antibodies show similar agonism to the polyvalent preparations described above.

Therefore, polyvalent or polyclonal preparations of anti CTLA-4 antibodies are useful for agonizing the CTLA-4 receptor, thereby suppressing immune responses otherwise mediated by T cells bearing the CTLA-4 receptor. Some examples of diseases that can be treated using such polyvalent or polyclonal preparations of antibodies induce autoimmune disease, transplant rejection, and inflammation.

B. Uses

1. Activating Immune Responses a. Cancer

Some therapeutic methods treat patients with cancer. Blockade of CTLA-4 by antibodies can enhance the immune response to cancerous cells in the patient. Optionally, antibodies to CTLA-4 can be combined with an immunogenic agent, such as cancerous cells, purified tumor antigens (including recombinant proteins, peptides, and carbohydrate molecules), cells, and cells transfected with genes encoding immune stimulating cytokines and cell surface antigens such as B7 (see, e.g., Hurwitz, A. et al. (1998) *Proc. Natl. Acad. Sci. USA*. 95, 10067-10071).

In murine experimental systems, implantation of some tumors followed by the administration of anti-CTLA-4 antibodies can result in the rejection of tumors. In some cases tumor rejection of established tumors occurs; in other cases the growth of the tumor is slowed by the use of anti-CTLA-4 antibodies. In general CTLA-4 blockade is effective against immunogenic tumors. Operationally this is defined as those tumors for which vaccination using the tumor itself can lead to immunity to tumor challenge. In humans, some tumors have been shown to be immunogenic such as melanomas. It is anticipated that by raising the threshold of T cell activation by CTLA-4 blockade, we may expect to activate tumor responses in the host.

CTLA-4 blockade is most effective when combined with a vaccination protocol. Many experimental strategies for vaccination against tumors have been devised (see Rosenberg, S., 2000, Development of Cancer Vaccines, ASCO *Educational Book Spring*: 60-62; Logothetis, C., 2000, ASCO *Educational Book Spring*: 300-302; Khayat, D. 2000, ASCO *Educational Book Spring*: 414-428; Foon, K. 2000, ASCO *Educational Book Spring*: 730-738; see also Restifo, N. and Sznol, M., Cancer Vaccines, Ch. 61, pp. 3023-3043 in DeVita, V. et al. (eds.), 1997, *Cancer: Principles and Practice of Oncology*, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90 (80: 3539-43).

Anti-CTLA-4 blockade together with the use of GMCSF-modified tumor cell vaccines has been shown to be effective in a number of experimental tumor models such as mammary carcinoma (Hurwitz et al. (1998) supra), primary prostate cancer (Hurwitz A. et al., (2000) *Cancer Research* 60 (9): 2444-8) and melanoma (van Elsas, A et al. (1999) *J. Exp. Med.* 190: 355-66). In these instances, non-immunogenic tumors, such as the B16 melanoma, have been rendered susceptible to destruction by the immune system. The tumor cell vaccine may also be modified to express other immune activators such as IL2, and costimulatory molecules, among others.

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp 100, MAGE antigens, Trp-2. More importantly, many of these antigens can be shown to be the targets of tumor specific T cells found in the host. CTLA-4 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) *Science* 266, 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors. Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with CTLA-4 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269: 1585-1588; Tamura, Y. et al., (1997) *Science* 278: 117-120.

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with CTLA-4 blockade to activate more potent anti-tumor responses.

CTLA-4 blockade may also be combined with standard cancer treatments. CTLA-4 blockade may be effectively combined with chemotherapeutic regimes. In these instances, it may be possible to reduce the dose of chemotherapeutic reagent administered (Mokyr, M. et al. (1998) *Cancer Research* 58: 5301-5304). The scientific rationale behind the combined use of CTLA-4 blockade and chemotherapy is that cell death, that is a consequence of the cytotoxic action of most chemotherapeutic compounds, should result in increased levels of tumor antigen in the antigen presentation pathway. Other combination therapies that may result in synergy with CTLA-4 blockade through cell death are radiation, surgery, and hormone deprivation (Kwon, E. et al. (1999) *Proc. Natl. Acad. Sci. U.S.A.* 96 (26): 15074-9. Each of these protocols creates a source of tumor antigen in the host. Angiogenesis inhibitors may also be combined with CTLA-4 blockade. Inhibition of angiogenesis leads to tumor cell death which may feed tumor antigen into host antigen presentation pathways.

CTLA-4 blocking antibodies can also be used in combination with bispecific antibodies that target Fc alpha or Fc gamma receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (i.e., Her-2/neu) bispecific antibodies have been used to target macrophages to sites of tumor. This targeting may more effectively activate tumor specific responses. The T cell arm of these responses would by augmented by the use of CTLA-4 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others Tgfβ (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Antibodies to each of these entities may be used in combination with anti-CTLA-4 to counteract the effects of the immunosuppressive agent and favor tumor immune responses by the host.

Other antibodies which may be used to activate host immune responsiveness can be used in combination with anti-CTLA-4. These include molecules on the surface of dendritic cells which activate DC function and antigen presentation. Anti-CD40 antibodies are able to substitute effectively for T cell helper activity (Ridge, J. et al. (1998) *Nature* 393: 474-478). and can be used in conjunction with CTLA-4 antibodies (Ito, N. et al. (2000) *Immunobiology* 201 (5) 527-40). Activating antibodies to T cell costimulatory molecules such as OX-40 (Weinberg, A. et al. (2000) *J Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. CTLA-4 blockade can be used to increase the effectiveness of the donor engrafted tumor specific T cells (Blazar, B. et al. (1999) *J Immunol* 162: 6368-6377).

There are also several experimental treatment protocols that involve ex vivo activation and expansion of antigen specific T cells and adoptive transfer of these cells into recipients in order to antigen-specific T cells against tumor (Greenberg, R. & Riddell, S. (1999) 285: 546-51). These methods may also be used to activate T cell responses to infectious agents such as CMV (see below). Ex vivo activation in the presence of anti-CTLA-4 antibodies may be expected to increase the frequency and activity of the adoptively transferred T cells.

b. Infectious Diseases

Other methods of the invention are used to treat patients that have been exposed to particular toxins or pathogens. Similar to its application to tumors as discussed above, antibody mediated CTLA-4 blockade can be used alone, or as an adjuvant, in combination with vaccines, to stimulate the immune response to pathogens, toxins, and self-antigens. CTLA-4 blockade has been shown to be effective in the acute phase of infections of *Nippostrongylus brasiliensis* (McCoy, K. et al. (1997) 186(2); 183-187) and *Leishmania donovani* (Murphy, M. et al. (1998) *J. Immunol.* 161:4153-4160). Examples of pathogens for which this therapeutic approach may be particularly useful, include pathogens for which there is currently no effective vaccine, or pathogens for which conventional vaccines are less than completely effective. These include, but are not limited to HIV, *Hepatitis* (A, B, & C), *Influenza, Herpes, Giardia, Malaria, Leishmania, Staphylococcus Aureus, Pseudomonas aeruginosa*. CTLA-4 blockade is particularly useful against established infections by agents such as HIV that present altered antigens over the course of the infections. These novel epitopes are recognized as foreign at the time of anti-human CTLA-4 administration, thus provoking a strong T cell response that is not dampened by negative signals through CTLA-4.

Some examples of pathogenic viruses causing infections treatable by methods of the invention include *hepatitis* (A, B, or C), *herpes* virus (e.g., VZV, HSV-1, HAV-6, HSV-II, and CMV, *Epstein Barr* virus), *adenovirus, influenza* virus, *flaviviruses, echovirus, rhinovirus, coxsackie* virus, *cornovirus*, respiratory syncytial virus, *mumps* virus, *rotavirus, measles* virus, *rubella* virus, parvovirus, vaccinia virus, HTLV virus, *dengue* virus, *papillomavirus, molluscum* virus, *poliovirus, rabies* virus, JC virus and *arboviral encephalitis* virus.

Some examples of pathogenic bacteria causing infections treatable by methods of the invention include *chlamydia, rickettsial* bacteria, *mycobacteria, staphylococci, streptococci, pneumonococci, meningococci* and *conococci, klebsiella, proteus, serratia, pseudomonas, legionella, diphtheria, salmonella, bacilli, cholera, tetanus, botulism, anthrax, plague, leptospirosis*, and *Lymes* disease bacteria.

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus *Mucorales* (*Mucor, Absidia, Rhizophus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

In all of the above methods, a CTLA-4 blockade can be combined with other forms of immunotherapy such as cytokine treatment (e.g. interferons, GM-CSF, GCSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

c. Promoting Beneficial "Autoimmune" Reactions for the Treatment of Disease and Therapeutic Intervention.

The ability of anti-CTLA-4 antibodies to provoke and amplify autoimmune responses has been documented in a number of experimental systems (EAE—Experimental Autoimmune Encephalomyelitis, a murine model for MS (Perrin, P. et al. (1996) *J Immunol* 157 (4): 1333-1336); diabetes (Luhder, F. et al. (1998) supra). Indeed, induction of anti-tumor responses using tumor cell and peptide vaccines reveals that many anti-tumor responses involve anti-self reactivities (depigmentation observed in anti-CTLA-4+GM-CSF modified B16 melanoma in van Elsas et al. supra; depigmentation in Trp-2 vaccinated mice (Overwijk, W. et al. (1999) *Proc. Natl. Acad. Sci. U.S.A.* 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) *J Immunother Emphasis Tumor Immunol* 19 (1): 81-4).

Therefore, it is possible to consider using anti-CTLA-4 blockade in conjunction with various self proteins in order to devise vaccination protocols to efficiently generate immune responses against these self proteins for disease treatment. For example, Alzheimers disease involves inappropriate accumulation of Aβ peptide in amyloid deposits in the brain; antibody responses against amyloid are able to clear these amyloid deposits (Schenk et al., (1999) Nature 400: 173-177).

Other self proteins may also be used as targets such as IgE for the treatment of allergy and asthma, and TNF for rhematoid arthritis. Finally, antibody responses to various hormones may be induced by the use of anti-CTLA-4 antibody. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-CTLA-4 antibody can be used for induction of therapeutic autoimmune responses to treat patients having an inappropriate accumulation of other self-antigens, such as amyloid deposits, including Aβ in Alzheimer's disease, cytokines such as TNFα, and IgE.

2. Inactivating Immune Responses

Disorders caused by immune responses are called hypersensitivity disease. Diseases caused by failure of self-tolerance and subsequent immune responses against self, or autologous, antigens are called autoimmune diseases. Hypersensitivity diseases can also result from uncontrolled or excessive responses against foreign antigens, such as microbes.

Although soluble antibodies to human CTLA-4 have been shown to promote the expansion and activation of T cells (i.e., where CTLA-4 function (e.g., binding to ligand) is inhibited; in this scenario the antibodies are antagonists to CTLA-4 function), increasing the valency of these same antibodies produces the opposite effect (where now, in contrast, the antibodies are acting as agonists of CTLA-4 to suppress the immune response) (see, e.g., Krummel and Allison, 1996, *J. Exp. Med.* 183, 2533-2540). For the purposes of inactivating antigen specific T cell responses, such as those that are the targets of pathogenic autoreactive T cells, the target antigen which is specific for these T cells (i.e. antigen and/or MHC/antigen complexes) must be administered with the polyvalent form of anti-CTLA-4 antibody.

a. Inflammation

Inflammation represents the consequence of capillary dilation with accumulation of fluid and migration of phagocytic leukocytes, such as granulocytes and monocytes. Inflammation is important in defending a host against a variety of infections but can also have undesirable consequences in inflammatory disorders, such as anaphylactic shock, arthritis, gout and ischemia-reperfusion. Activated T-cells have an important modulatory role in inflammation, releasing interferon γ and colony stimulating factors that in turn activate phagocytic leukocytes. The activated phagocytic leukocytes are induced to express a number of specific cells surface molecules termed homing receptors, which serve to attach the phagocytes to target endothelial cells. Inflammatory responses can be reduced or eliminated by treatment with the therapeutic agents of the present invention. For example, polyvalent preparations of antibodies against CTLA-4 block activation of activated T-cells, thereby preventing these cells from releasing molecules required for activation of phagocytic cell types.

b. Autoimmune Diseases

A further situation in which immune suppression is desirable is in treatment of autoimmune diseases such as insulin-dependent diabetes mellitus, multiple sclerosis, stiff man syndrome, rheumatoid arthritis, myasthenia gravis and lupus erythematosus. In these diseases, the body develops a cellular and/or humoral immune response against one of its own antigens leading to destruction of that antigen, and potentially crippling and/or fatal consequences. Activated T-cells are believed to play a major role in many autoimmune diseases such as diabetes mellitus. Autoimmune diseases are treated by administering one of the therapeutic agents of the invention that inhibits activation of T cells. Optionally, the autoantigen, or a fragment thereof, against which the autoimmune disease is targeted can be administered shortly before, concurrently with, or shortly after the immunosuppressive agent. In this manner, tolerance can be induced to the autoantigen under cover of the suppressive treatment, thereby obviating the need for continued immunosuppression. See, e.g., Cobbold et al., WO 90/15152 (1990).

c. Graft Versus Host Disease

A related use for the therapeutic agents of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used to inhibit activation of donor leukocytes, thereby inhibiting their ability to lyse target cells in the host.

d. Transplant Rejection

Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immune-tolerance in the recipient to the transplanted allograft or organ. When allogeneic cells or organs are transplanted into a host (i.e., the donor and donee are different individual from the same species), the host immune system is likely to mount an immune response to foreign antigens in the transplant (host-versus-graft disease) leading to destruction of the transplanted tissue. CD8$^+$ cells, CD4$^+$ cells and monocytes are all involved in the rejection of transplant tissues. The therapeutic agents of the present invention are useful to inhibit T-cell mediated alloantigen-induced immune responses in the donee thereby preventing such cells from participating in the destruction of the transplanted tissue or organ.

B. Methods for Detecting/Measuring the Presence of CTLA-4 in a Sample

The invention further provides methods for detecting the presence of human CTLA-4 antigen in a sample, or measuring the amount of human CTLA-4 antigen, comprising contacting the sample, and a control sample, with a human monoclonal antibody, or an antigen binding portion thereof, which specifically binds to human CTLA-4, under conditions that allow for formation of a complex between the antibody or portion thereof and human CTLA-4. The formation of a complex is then detected, wherein a difference complex formation between the sample compared to the control sample is indicative the presence of human CTLA-4 antigen in the sample.

C. Kits

Also within the scope of the invention are kits comprising the compositions (e.g., human sequence antibodies, human antibodies, multispecific and bispecific molecules) of the invention and instructions for use. The kit can further contain a least one additional reagent, or one or more additional human antibodies of the invention (e.g., a human antibody having a complementary activity which binds to an epitope in CTLA-4 antigen distinct from the first human antibody). Kits typically include a label indicating the intended use of the contents of the kit. The term label includes any writing, or recorded material supplied on or with the kit, or which otherwise accompanies the kit.

EXAMPLES

Example 1

Generation of Cmu Targeted Mice

Construction of a CMD Targeting Vector.

The plasmid pICEmu contains an EcoRI/XhoI fragment of the murine Ig heavy chain locus, spanning the mu gene, that was obtained from a Balb/C genomic lambda phage library (Marco et al. *Cell* 22: 187, 1980). This genomic fragment was subcloned into the XhoI/EcoRI sites of the plasmid pICEMI9H (Marsh et al.; Gene 32, 481-485, 1984). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in *E. coli.*

Figure 1:
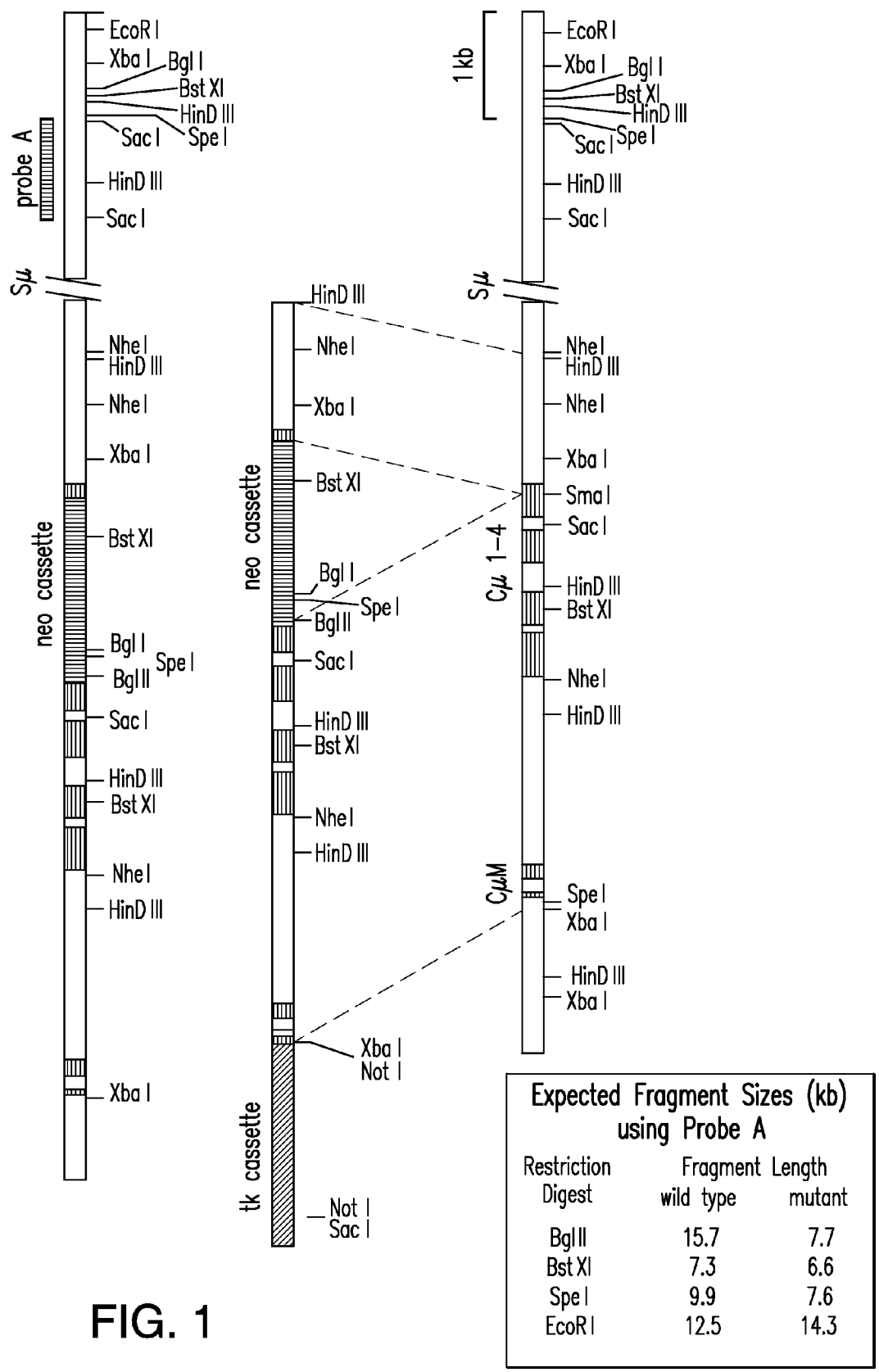
FIG. 1 shows schematics illustrating the targeted insertion of a neo cassette into the Sma I site of the µl exon.

The targeting vector was constructed as follows (see FIG. 1). A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of CmuI to the SmaI site located within Cmu 1. The resulting plasmid was digested with SmaI/SpeI and the approximately 4 kb SmaI/XbaI fragment from pICEmu, extending from the Sma I site in Cmu1 3' to the XbaI site located just downstream of the last Cmu exon, was inserted. The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al. (1987) Gene 60: 65-74) and containing the pgk polyadenylation site (PvuII/HindIII fragment; Boer et al., (1990) Biochemical Genetics 28: 299-308). This cassette was obtained from the plasmid pKJ1 (described by Tybulewicz et al. (1991) Cell 65: 1153-1163) from which the neo cassette was excised as an EcoRI/HindIII fragment and subcloned into EcoRI/HindIII digested pGEM-7Zf (+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences. The resulting plasmid was linearized with Not I, and a herpes simplex virus thymidine kinase (tk) cassette was inserted to allow for enrichment of ES clones bearing homologous recombinants, as described by Mansour et al., (1988) Nature 336: 348-352. This cassette consists of the coding sequences of the tk gene bracketed by the mouse pgk promoter and polyadenylation site, as described by Tybulewicz et al. (1991) Cell 65: 1153-1163. The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.

Generation and Analysis of Targeted ES Cells.

AB-1 ES cells (McMahon, A. P. and Bradley, A., (1990) Cell 62: 1073-1085) were grown on mitotically inactive SNL76/7 cell feeder layers (ibid.) essentially as described (Robertson, E. J. (1987) in Teratocarcinomas and Embryonic Stem Cells: a Practical Approach (E. J. Robertson, ed.) Oxford: IRL Press, p. 71-112). The linearized CMD targeting vector was electroporated into AB-1 cells by the methods described Hasty et al. (Hasty, P. R. et al. (1991) Nature 350: 243-246). Electroporated cells were plated into 100 mm dishes at a density of 1-2×106 cells/dish. After 24 hours, G418 (200 micrograms/ml of active component) and FIAU (5×10-7 M) were added to the medium, and drug-resistant clones were allowed to develop over 8-9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described Laird et al. (Laird, P. W. et al., (1991) Nucleic Acids Res. 19: 4293). Isolated genomic DNA was digested with SpeI and probed with a 915 by SacI fragment, probe A (FIG. 1), which hybridizes to a sequence between the mu intronic enhancer and the mu switch region. Probe A detects a 9.9 kb SpeI fragment from the wild type locus, and a diagnostic 7.6 kb band from a mu locus which has homologously recombined with the CMD targeting vector (the neo expression cassette contains a SpeI site). Of 1132 G418 and FIAU resistant clones screened by Southern blot analysis, 3 displayed the 7.6 kb Spe I band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmul exon.

Generation of Mice Bearing the Mutated Mu Gene.

The three targeted ES clones, designated number 264, 272, and 408, were thawed and injected into C57BL/6J blastocysts as described by Bradley (Bradley, A. (1987) in Teratocarcinomas and Embryonic Stem Cells: a Practical Approach. (E. J. Robertson, ed.) Oxford: IRL Press, p. 113-151). Injected blastocysts were transferred into the uteri of pseudopregnant females to generate chimeric mice representing a mixture of cells derived from the input ES cells and the host blastocyst. The extent of ES cell contribution to the chimera can be visually estimated by the amount of agouti coat coloration, derived from the ES cell line, on the black C57BL/6J background. Clones 272 and 408 produced only low percentage chimeras (i.e. low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BO digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of Transgenic Mice for Functional Inactivation of Mu Gene.

To determine whether the insertion of the neo cassette into Cmu1 has inactivated the Ig heavy chain gene, a clone 264 chimera was bred with a mouse homozygous for the JHD mutation, which inactivates heavy chain expression as a result of deletion of the JH gene segments (Chen et al., (1993) Immunol. 5: 647-656). Four agouti offspring were generated. Serum was obtained from these animals at the age of 1 month and assayed by ELISA for the presence of murine IgM. Two of the four offspring were completely lacking IgM (Table 1). Genotyping of the four animals by Southern blot analysis of DNA from tail biopsies by BglI digestion and hybridization with probe A (FIG. 1), and by StuI digestion and hybridization with a 475 by EcoRI/StuI fragment (ibid.) demonstrated that the animals which fail to express serum IgM are those in which one allele of the heavy chain locus carries the JHD mutation, the other allele the Cmu1 mutation. Mice heterozygous for the JHD mutation display wild type levels of serum Ig. These data demonstrate that the Cmu1 mutation inactivates expression of the mu gene.

TABLE 1

Level of serum IgM, detected by ELISA, for mice carrying both the CMD and JHD mutations (CMD/JHD), for mice heterozygous for the JHD mutation (+/JHD), for wild type (129Sv × C57BL/6J)F1 mice (+/+), and for B cell deficient mice homozygous for the JHD mutation (JHD/JHD).

| Mouse | Serum IgM (micrograms/ml) | Ig H chain genotype |
|---|---|---|
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | <0.002 | JHD/JHD |

Example 2

Generation of HCo12 Transgenic Mice

The HCo12 Human Heavy Chain Transgene.

The HCo12 transgene was generated by coinjection of the 80 kb insert of pHC2 (Taylor et al., 1994, Int. Immunol., 6: 579-591) and the 25 kb insert of pVx6. The plasmid pVx6 was constructed as described below.

An 8.5 kb HindIII/SalI DNA fragment, comprising the germline human VH1-18 (DP-14) gene together with approximately 2.5 kb of 5' flanking, and 5 kb of 3' flanking genomic sequence was subcloned into the plasmid vector pSP72 (Promega, Madison, Wis.) to generate the plasmid p343.7.16. A 7 kb BanaHI/HindIII DNA fragment, comprising the germline human VH5-51 (DP-73) gene together with approximately 5 kb of 5' flanking and 1 kb of 3' flanking genomic sequence, was cloned into the pBR322 based plasmid cloning vector pGP1f (Taylor et al. 1992, Nucleic Acids Res. 20: 6287-6295), to generate the plasmid p251f. A new cloning vector derived from pGP1f, pGP1k (Seq. ID #1), was digested with EcoRV/BamHI, and ligated to a 10 kb EcoRV/BamHI DNA fragment, comprising the germline human VH3-23 (DP47) gene together with approximately 4 kb of 5' flanking and 5 kb of 3' flanking genomic sequence. The resulting plasmid, p112.2RR.7, was digested with BamHI/SalI and ligated with the 7 kb purified BamHI/SalI insert of p251 f. The resulting plasmid, pVx4, was digested with XhoI and ligated with the 8.5 kb XhoI/SalI insert of p343.7.16. A clone was obtained with the VH1-18 gene in the same orientation as the other two V genes. This clone, designated pVx6, was then digested with NotI and the purified 26 kb insert coinjected—together with the purified 80 kb NotI insert of pHC2 at a 1:1 molar ratio—into the pronuclei of one-half day (C57BL/6J× DBA/2J)F2 embryos as described by Hogan et al. (B. Hogan et al.,, Manipulating the Mouse Embryo, A Laboratory Manual, 2nd edition, 1994, Cold Spring Harbor Laboratory Press, Plainview N.Y.). Three independent lines of transgenic mice comprising sequences from both Vx6 and HC2 were established from mice that developed from the injected embryos. These lines are designated (HCo12)14881, (HCo12)15083, and (HCo12)15087. Each of the three lines were then bred with mice comprising the CMD mutation described in Example 1, the JKD mutation (Chen et al,. 1993, EMBO J. 12: 811-820), and the (KCo5)9272 transgene (Fishwild et al. 1996, Nature Biotechnology 14: 845-851). The resulting mice express human heavy and kappa light chain transgenes in a background homozygous for disruption of the endogenous mouse heavy and kappa light chain loci.

Example 3

Generation of Human IgG Kappa Anti-Human CTLA-4 Monoclonal Antibodies

Cell Based Antigen

A DNA segment encoding a fusion protein comprising sequences from the human CTLA-4 and the murine CD3zeta genes was constructed by PCR amplification of cDNA clones together with bridging synthetic oligonucleotides. The encoded fusion protein contains the following sequences: i. human CTLA-4 encoding amino acids 1-190 (containing the signal peptide, the extracellular domain of human CTLA-4 and the entirety of the presumed transmembrane sequence of human CTLA-4) and ii. murine CD3zeta from amino acid 52 to the carboxy terminus (Weissman et al. (1988) *Science* 239: 1018-1021). The amplified PCR product was cloned into a plasmid vector and the DNA sequence was determined. The cloned insert was then subcloned into the vector pBABE (which contains a gene encoding for puromycin resistance (Morganstern, J P and Land, H Nucl. Acids Res. 18: 3587-96 (1990)) to create pBABE-huCTLA-4/CD3z. pBABE-huCTLA-4/CD3z was transfected into the retroviral packaging line, ψ-2, and a pool of puromycin resistant cells were selected. These cells were co-cultured with the murine T cell hybridoma BW5147 (ATCC #TIB-47). After 2 days of co-culture the non-adherent BW5147 cells were removed and selected for resistance to puromycin. The puromycin resistant cell pool was subcloned by limiting dilution and tested for surface expression of human CTLA-4 by FACS. A clone expressing high levels of human CTLA-4 at the cell surface was selected.

Soluble Antigen

Recombinant CTLA-4 fusion protein comprising the extracellular domain of human CTLA-4 was purchased from R&D Systems (Cat. #325-CT-200). Extracellular CTLA-4 fragment was prepared by proteolytic cleavage of the CTLA-4 fusion protein at a Factor Xa protease cleavage site located after the C-terminus of the CTLA-4 extracellular domain. Fusion protein was treated with Factor Xa at a ratio of 50:1 of fusion protein to Factor Xa, and the CTLA-4 fragment was isolated by passage over protein G-Sepharose and Mono Q HPLC. Fractions were tested for the presence of human CTLA-4 dimer were by SDS-PAGE and by binding to cells expressing mouse 137 molecules (LtkmB7.1: mouse Ltk(-) cells transfected with a mouse B7.1 cDNA clone expression vector). Positive fractions were pooled and dialyzed into PBS buffer.

Transgenic Mice

Two different strains of mice were used to generate CTLA-4 reactive monoclonal antibodies. Strain ((CMD)++; (JKD)++; (HCo7)11952+/++; (KCo5)9272+/++), and strain ((CMD)++; (JKD)++; (HCo12)15087+/++; (KCo5) 9272+/++). Each of these strains are homozygous for disruptions of the endogenous heavy chain (CMD) and kappa light chain (JKD) loci. Both strains also comprise a human kappa light chain transgene (KCo5), with individual animals either hemizygous or homozygous for insertion #11952. The two strains differ in the human heavy chain transgene used. Mice were hemizygous or homozygous for either the HCo7 or the HCo12 transgene. The CMD mutation is described above in Example 1. The generation of (HCo12)15087 mice is described in Example 2. The JKD mutation (Chen et al. 1993, *EMBO J.* 12: 811-820) and the (KCo5)9272 (Fishwild et al. 1996, *Nature Biotechnology* 14: 845-851) and (HCo7)11952 mice, are described in U.S. Pat. No. 5,770,429 (Lonberg & Kay, Jun. 23, 1998).

Immunization

Transgenic mice were initially immunized i.p. with 1-3× $10^7$ cellsin PBS, or with 10-50 ug soluble fusion protein in adjuvant (either complete Freund's or Ribi). Immunized mice were subsequently boosted every 2 to 4 weeks i.p. with 1-3× $10^7$ cells in PBS. Animals were kept on protocol for 2 to 5 months. Prior to fusion, animals were boosted i.v. on days −3 and −2 with approximately $10^6$ cells, or with 10-20 ug soluble antigen (fusion protein or fusion protein and extracellular fragment). Some animals also received fusion protein i.v. on day −4. Successful fusions resulting in CTLA-4 reactive IgG kappa monoclonal antibodies were obtained from mice immunized by a variety of different protocols, including cells only, soluble antigen only, and cell immunizations followed by soluble antigen given i.v. prior to fusion.

Fusions

Spleen cells were fused to mouse myeloma cells (line P3 X63 Ag8.6.53, ATCC CRL 1580, or SP2/0-Ag14, ATCC CRL 1581) by standard procedures (Harlow and Lane, 1988, Antibodies, A Laboratory Manual, Cold Spring Harbor Laboratory Press, Cold Spring Harbor N.Y.; Kennett et al. 1980, *Monoclonal Antibodies, Hybridomas: A New Dimension in Biological Analysis*. Plenum, New York; Oi and Hertzenberg, 1980, *Immunoglobulin Producing Hybrid Cell Lines*, in *Selected Methods In Cellular Immunology*, ed. Mishell and Shiigi, pp. 357-372. Freeman, San Francisco; Halk, 1984, *Methods in Enzymology: Plant Molecular Biology*, ed. Weissbach and Weissbach, pp. 766-780, Academic Press, Orlando, Fla.). Cells were cultured in DMEM, 10% FBS, OPI (Sigma O-5003), BME (Gibco 21985-023), 3% Origen Hybridoma Cloning Factor (Igen 1050-0615), and 5% P388d1 (ATCC TIB 63) conditioned media. HAT or HT supplement was added to the medium during initial growth and selection.

Hybridoma Screening

To identify hybridomas secreting human IgG kappa antibodies, ELISA plates (Nunc MaxiSorp) were coated overnight at 4° C. with 100 µl/well goat anti-human Fcgamma specific antibody (Jackson Immuno Research #109-006-098) at 1 ug/ml in PBS. Plates were washed and blocked with 100 ul/well PBS-Tween containing 1% BSA. Fifty ul cell culture supernatant was added followed by a 1-2 hour incubation. Plates were washed and then incubated for one hour with 100 ul/well goat anti-Kappa light chain conjugated to alkaline phosphatase or horseradish peroxidase (Sigma #A-3813, or #A-7164). Plates were washed three times in PBS-Tween between each step. An analogous assay was used to identify hybridomas that secrete human antibodies reactive with human CTLA-4. This assay was identical except that the ELISA plates were coated with recombinant CTLA-4 fusion protein instead of goat anti-human Fcgamma antibody.

Characterization of Monoclonal Antibodies

Figure 2A:
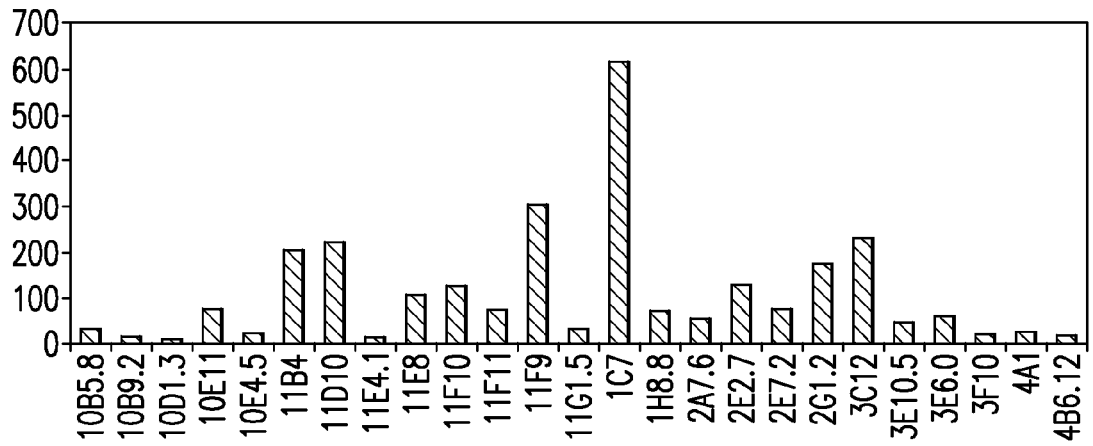
FIGS. 2A-B both show the results of experiments demonstrating that soluble human sequence antibodies against human CTLA-4 inhibit the binding of recombinant soluble human CTLA-4 to cells expressing mouse B7.1, as described in detail, below.
Figure 2B:
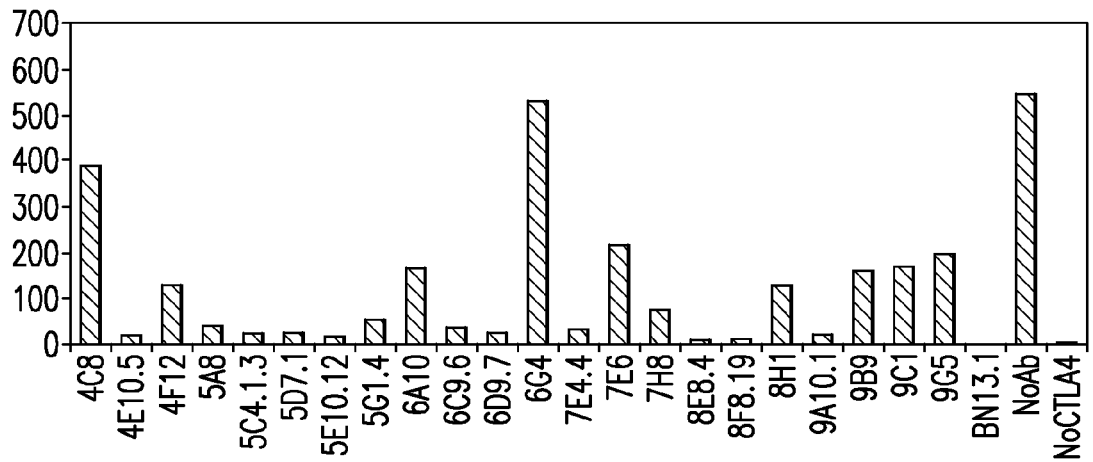

Seventy two hybridomas that were shown by ELISA to secrete human IgG kappa binding to human CTLA-4 were subcloned. Forty seven of these subclones were tested to determine if the secreted human antibodies bind to CTLA-4 expressing cells, and if the antibodies inhibit soluble CTLA-4 from binding to cells expressing B7. Binding was determined by flow cytometry. To measure inhibition, 50 microliters of each supernatant was incubated with $10^5$ LtkmB7.1 cells and 25 ng recombinant CTLA-4 fusion protein. Mean channel fluorescence was then determined by flow cytometry. FIG. 2 shows inhibition of soluble CTLA-4 binding to cells expressing B7.1. Mean channel fluorescence (MCF) of LtkmB7.1 cells stained with recombinant human CTLA-4 fusion protein was determined in the presence of hybridoma supernatant. Hybridomas that secrete blocking antibodies resulted in lower MCF values. BNI3.1 (Cat.#34580D, Pharmingen, San Diego, Calif.) was used as a positive control mouse monoclonal antibody that blocks CTLA-4/B7 binding.

Approximately 40% of the hybridomas appear to strongly inhibit CTLA-4 binding to the B7 ligand.

Antibodies from clones 10D1.3, 4B6.12, and 11E8, were then assayed by BIAcore (Biacore AB, Uppsala, Sweden) to determine binding kinetics. Purified recombinant CTLA-4 extracellular fragment was coupled to the CM5 sensor chip @ 1200 RU. Binding was measured by adding antibody at concentrations of 0.25, 0.5, 1, 2.5, and 5 ug/ml at a flow rate of 5 µl/min. The binding curves were fit to a Langmuir binding model using BIAevaluation software (Biacore AB, Uppsala, Sweden). Antibodies were purified by protein-A Sepharose chromatography. Determined on and off rates are shown in Table 2:

TABLE 2

Kinetics of binding of human IgG kappa antibodies to recombinant CTLA-4 immobilized on a surface.

| Hybridoma | ka (1/Ms) | kd (1/s) | Ka (1/M) |
|---|---|---|---|
| 10D1.3 | $4.1 \times 10^5$ | $1.0 \times 10^{-4}$ | $4 \times 10^9$ |
| 4B6.12 | $5.1 \times 10^5$ | $1.3 \times 10^{-4}$ | $4 \times 10^9$ |
| 11E8 | $4.3 \times 10^5$ | $1.8 \times 10^{-4}$ | $2 \times 10^9$ |

Figure 3:
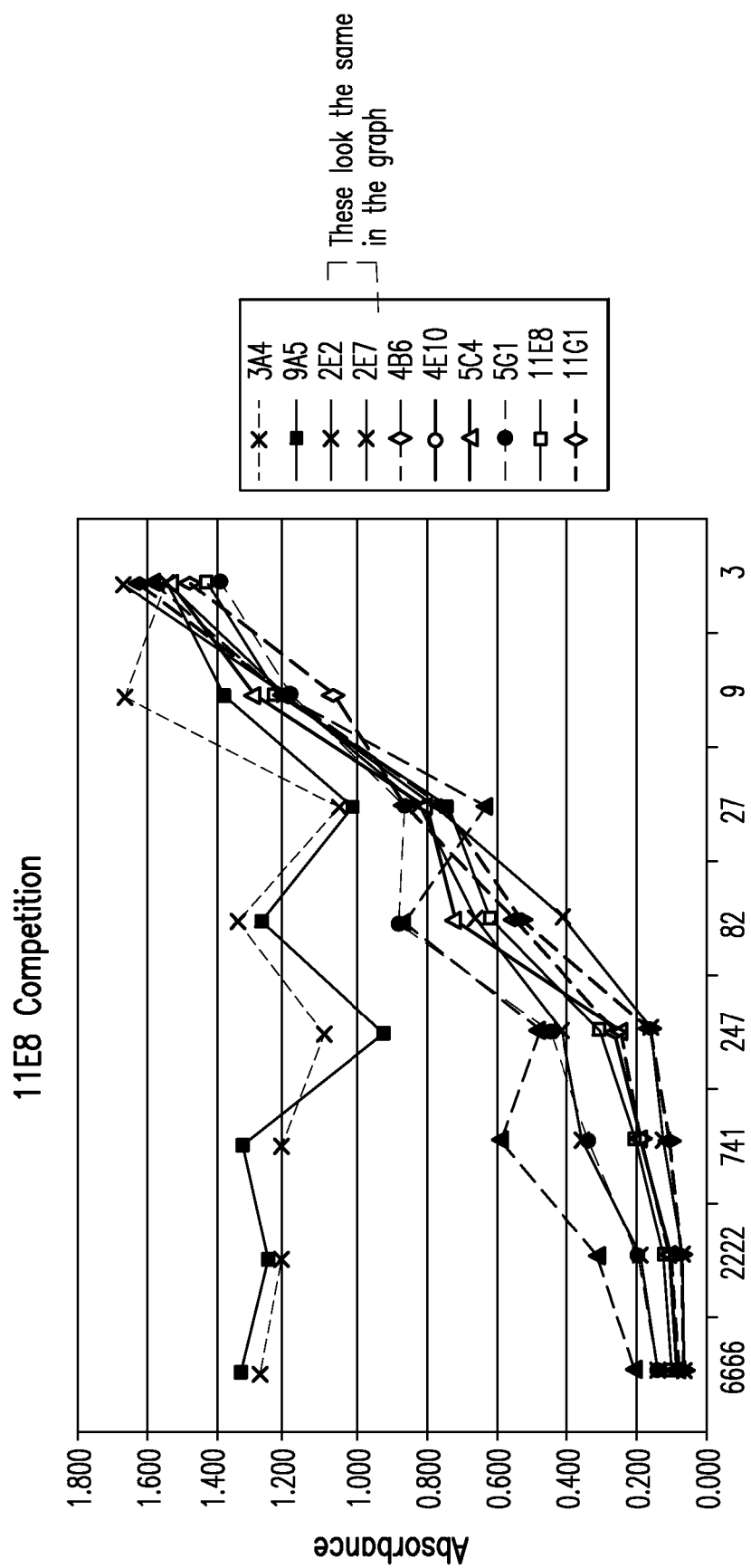
FIG. 3 shows the results of a competitive binding assay to identify human sequence antibodies of the invention that recognize non-overlapping epitopes on human CTLA-4, as described in detail, below.

Serial dilutions of 10 different human IgG kappa anti-human CTLA-4 monoclonal antibodies (3A4, 9A5, 2E2, 2E7, 4B6, 4E10, 5C4, 5G1, 11E8, and 11G1) were added to microtiter wells coated with recombinant CTLA-4 fusion protein. After a 2 hour incubation, biotinylated antibody 11E8 was added to each well at a concentration of 0.1 ug/ml. The samples were incubated for 30 minutes, washed, and bound antibody detected with alkaline phosphatase/streptavidin conjugate. The titrations are shown in FIG. 3. Antibody 11E8 binding was blocked by itself and 7 of the other human antibodies. However, binding was not blocked by antibodies 3A4 or 9A5. Reciprocal binding experiments showed that 11E8 binding did not block either 3A4 or 9A5 binding to CTLA-4.

DNA Sequence

RNA was extracted from approximately $2 \times 10^6$ cells of each subcloned hybridoma cell line and used to synthesize cDNA using reagents and protocols from Invitrogen (Micro-FastTrack and cDNA Cycle: Cat. #L1310-01, and #K1520-02, Invitrogen, Carlsbad, Calif.). Human immunoglobulin heavy and kappa light chain V region fragments were amplified by PCR using pfu polymerase (Stratagene, La Jolla, Calif.), degenerate FR1 primers and unique constant region primers. The resulting PCR fragments were cloned into the pCR-Blunt vector (Invitrogen, Carlsbad, Calif.) and the sequence of the insert determined. The preliminary sequences for the heavy and light chain fragment of hybridoma 10D1.3 are shown in FIG. 4. The determined sequences for the heavy and light chain fragment of hybridoma 10D1.3 are shown in FIG. 5 through FIG. 8.

TABLE 3

CDR sequences of light and heavy chains for MAbs 10D1, 4B6, and 1E2.

| Chain | HuMAb | CDR1 | SEQ ID NO: | CDR2 | SEQ ID NO: | CDR3 | SEQ ID NO: |
|---|---|---|---|---|---|---|---|
| Light Chain | 10D1 | RASQSVGSSYLA | 24 | GAFSRAT | 29 | QQYGSSPWT | 35 |
| | 4B6 | RASQSVGSSFLA | 25 | GASSRAT | 30 | QQYGSSPWT | 35 |
| | 1E2 | RASQGISSWLA | 26 | AASSLQS | 31 | QQYNSYPPT | 36 |

TABLE 3-continued

CDR sequences of light and heavy chains for MAbs 10D1, 4B6, and 1E2.

| Chain | HuMAb | CDR1 | SEQ ID NO: | CDR2 | SEQ ID NO: | CDR3 | SEQ ID NO: |
|---|---|---|---|---|---|---|---|
| Heavy Chain | 10D1 | SYTMH | 27 | FISYDGNNKYYADSVKG | 32 | TGWLGPFDY | 37 |
| | 4B6 | SYTMH | 27 | FISYDGSNKHYADSVKG | 33 | TGWLGPFDY | 37 |
| | 1E2 | SYGMH | 28 | VIWYDGSNKYYADSVKG | 34 | APNYIGAFDV | 38 |

Example 4

Use of Partial Antibody Sequences to Express Intact Antibodies

Antibodies interact with target antigens predominantly through amino acid residues that are located in the six heavy and light chain complimentarily determining regions (CDR's). For this reason, the amino acid sequences within CDR's are more diverse between individual antibodies than sequences outside of CDR's. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (Jones et al. 1986, *Nature* 321, 522-525). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequence of a high affinity secondary repertoire antibody at individual nucleotides because of somatic mutations. However, somatic mutations are not distributed evenly across the variable region. For example, somatic mutations are relatively infrequent in the amino-terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999, which is herein incorporated by reference for all purposes). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable region. Heavy and light chain leader sequences are cleaved during protein maturation and do not contribute to the properties of the final antibody. For this reason it is not necessary to use the corresponding germline leader sequence for expression constructs. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion of particular restriction sites, or optimization of particular codons.

The nucleotide sequences of heavy and light chain transcripts from a hybridomas are used to design an overlapping set of synthetic oligonucleotides to create synthetic V sequences with identical amino acid coding capacities as the natural sequences. The synthetic heavy and kappa light chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266, 19867-19870); and, HindIII sites are engineered upstream of the translation initiation sites.

For both the heavy and light chain variable regions, the optimized coding, and corresponding non-coding, strand sequences are broken down into 30-50 nucleotide segments such that the breaks between nucleotides for the coding strand sequence occur at approximately the midpoint of the corresponding non-coding oligonucleotide. Thus, for each chain, the oligonucleotides can be assemble into overlapping double stranded sets that completely span the desired sequence. These oligonucleotides are combined into pools that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric IgG1κ or IgG4κ antibodies, Similar plasmids can be constructed for expression of other heavy chain isotypes, or for expression of antibodies comprising lambda light chains.

The kappa light chain plasmid, pCK7-96 (SEQ ID NO:39), includes the kappa constant region and polyadenylation site, such that kappa sequences amplified with 5' primers that include HindIII sites upstream of the initiator methionine can be digested with HindIII and BbsI, and cloned into pCK7-96 digested with HindIII and BbsI to reconstruct a complete light chain coding sequence together with a polyadenylation site. This cassette can be isolated as a HindIII/NotI fragment and ligated to transcription promoter sequences to create a functional minigene for transfection into cells.

The gamma1 heavy chain plasmid, pCG7-96 (SEQ ID NO:40), includes the human gamma1 constant region and polyadenylation site, such that gamma sequences amplified with 5' primers that include HindIII sites upstream of the initiator methionine can be digested with HindIII and AgeI, and cloned into pCG7-96 digested with HindIII and AgeI to reconstruct a complete gamma1 heavy chain coding sequence together with a polyadenylation site. This cassette can be isolated as a HindIII/SalI fragment and ligated to transcription promoter sequences to create a functional minigene for transfection into cells.

The gamma4 heavy chain plasmid, pG4HE (SEQ ID NO:41), includes the human gamma4 constant region and polyadenylation site, such that gamma sequences amplified with 5' primers that include HindIII sites upstream of the initiator methionine can be digested with HindIII and AgeI, and cloned into pG4HE digested with HindIII and AgeI to reconstruct a complete gamma4 heavy chain coding sequence together with a polyadenylation site. This cassette can be isolated as a HindIII/EcoRI fragment and ligated to transcription promoter sequences to create a functional minigene for transfection into cells.

A number of different promoters (including but not limited to CMV, ubiquitin, SRalpha, and beta-actin) can be used to express the reconstructed heavy and light chain genes. For example the vector pcDNA3.1+ (Invitrogen, Carlsbad, Calif.), can be cleaved with Hindu and either NotI, XhoI, or EcoRI, for ligation with either the kappa, gamma1, or gamma4 cassettes described above, to form expression vectors that can be directly transfected into mammalian cells.

Example 5

10D.1 Binding to CTLA-4

A. 10D1 Binding to Purified Recombinant Human CTLA-4

Binding of 10D1 to purified recombinant human CTLA-4 was shown by ELISA using standard methods and procedures (FIG. 9 and FIG. 10). Microtiter plates coated with purified CTLA-4 were incubated with varying concentration of 10D1, and then developed with goat anti-human IgG F(ab')$_2$ conjugated to alkaline phosphatase. The data demonstrate dose-dependent binding of 10D1 that is well fit to a 4-parameter curve (correlation coefficient is −1.0). The half-maximal binding at 15 ng/ml reflects the high binding capacity of 10D1 to CTLA-4. Saturation of binding was observed at approximately 0.1 µg/ml.

B. 10D.1 Binding to CTLA-4 Expressed on the Plasma Membrane of T-Cells

In order to demonstrate binding of 10D1 to CTLA-4 expressed on the plasma membrane of T-cells, the results in FIG. 10 from a flow cytometric assay are shown. The flow cytometric assay was used with a T-cell line transfected to express high levels of human CTLA-4 (designated 58αβCTLA-4/CD3zeta cells). Varying concentrations of fluoresceinated 10D1 (10D1-FITC) were incubated with 58αβCTLA-4 cells. The cell associated fluorescence was determined by flow cytometry. As seen with the purified CTLA4, 10D1 bound to CTLA4-expressing cells in a dose-dependent manner that was well fit to a 4-paramater equation (correlation coefficient is −0.999). The half-maximal binding was 190 ng/ml, and saturation was achieved at 2 µg/ml. 10D1 did not bind to any CTLA4-negative cell lines tested, including SKBR-3, BT474 and MCF10A breast epithelial tumors and L540 Hodgkin's tumor cells, nor did it bind to cells expressing murine CTLA-4. These data indicate the specificity of 10D1 for human CTLA. However, 10D1 was shown to cross-react with macaque CTLA-4 (see below).

C. Cross-Reactivity of 10D1 with Normal Human Tissues

In this study, a fluoresceinated form of the test article (10D1-FITC) was used to evaluate binding. The objective of the study was to evaluate potential cross-reactivity of 10D1-FITC with cryosections of normal human tissues. No unanticipated cross-reactivity was observed.

The study was conducted in accordance with the Food and Drug Administration's Good Laboratory Practice (GLP) Regulations (21 CFR Part 58). The human tissue panel included all the tissue on the "suggested list of human tissues to be used for immunohistochemical investigations of cross reactivity' in Annex II of the EC CPMP Guideline III/5271/94, "Production and quality control of monoclonal antibodies" and all the tissues recommended in the 1997 US FDA/CBER "Points to Consider in the Manufacture and Testing of Monclonal Antibody Products for Human Use".

Using an indirect immunoperoxidase method, 10D1-FITC specifically stained positive control, human CTLA4-expressing, 58αβCTLA4CD3zeta cells as well as positive control lymphocytes in human tonsil. 10D1-FITC reactivity was moderate to intense and two concentrations of antibody were examined (10 µg/ml and 2.5 µg/ml). In both positive control 58αβCTLA4CD3zeta and positive control human tonsillar lymphocytes, 10D1-FITC specifically stained discrete, round, granules at membrane and in the cytoplasm immediately below the membrane. Reactivity was observed with occasional follicular, interfollicular, and subepithelial lymphocytes. Less than 1-2% of all tonsillar lymphocytes were reactive with 10D1-FITC.

10D1-FITC did not react with negative control human brain (cerebellum). An isotype-matched negative control antibody (HuIgG1-k-FITC) did not specifically bind to either the positive control human CTLA4-expressing 58αβCTLA4CD3zeta or human tonsil; nor did it bind specifically to negative control human brain (cerebellum).

To determine cross-reactivity, 10D1-FITC was applied to a panel of normal human tissues at two concentrations (10 µg/ml and 2.5 µg/ml). Specific 10D1-FITC reactivity was observed for lymphocytes in the tonsil (3/3 donors), submucosal lymphoid nodule in the colon (gastrointestinal tract-colon [1/3 donors]), and blood smears (2/3 donors).

Immunoreactive cells were identified as lymphocytes based on typical morphology (round molecular cells with large nucleus:cytoplasm ratio and scant cytoplasm, lack of dendritic processes, 10-15 µm in diameter) and location within the tissues (e.g., typical location within lymphoid tissues). In the tonsils from all three donors (test tissues), lymphocytes, 10D 1-FITC specifically stained discrete, round, granules at membrane and in the cytoplasm immediately below the membrane. Reactivity was observed with occasional follicular, interfollicular and subepithelial lymphocytes. Less than 1-2% of all tonsillar lymphocytes were reactive with 10D1-FITC.

In 1/3 donors examined, 10D1-FITC also specifically stained discrete granules in occasional follicular and interfollicular lymphocytes located in submucosal lymphoid nodules in the colon (gastrointestinal tract-colon [large intestine]). Again, discrete membrane granules were stained.

In peripheral blood smears from two of the three donors examined, 10D1-FITC specifically stained discrete granules approximately 1 µm in diameter associated with the membrane of rare lymphocytes. The granules were arranged in a ring or in a curved pattern. Less than 1-2% of all peripheral blood leukocytes were reactive with 10D1-FITC.

TABLE 4

Cross-Reactivity of MAb 10D1 With Normal Human Tissues

| Tissue | Test Article 10D1-FITC 10 µg/ml | 2.5 µg/ml | Negative Control Antibody HuIgG1-k-FITC 10 µg/ml | 2.5 µg/ml | Assay Control * | $\beta_2$-microglobulin |
|---|---|---|---|---|---|---|
| Positive Control 58αβCTLA4CD3zeta cells | 3-4+ | 2-4+ | Neg | Neg | Neg | Pos |
| Positive Control Lymphocytes in human tonsil | 2-3+ | 2-3+ | Neg | Neg | Neg | Pos |
| Negative Control Human brain - cerebellum | Neg | Neg | Neg | Neg | Neg | Pos |
| Adrenal | Neg | Neg | Neg | Neg | Neg | Pos |
| Blood | | | | | | Pos |
| Neutrophils | Neg | Neg | Neg | Neg | Neg | Pos |
| Lymphocytes | 2+ (rare) | Neg | Neg | Neg | Neg | Pos |
| Eosinophils | Neg | Neg | Neg | Neg | Neg | Pos |
| Monocytes | Neg | Neg | Neg | Neg | Neg | Pos |
| Platelets | Neg | Neg | Neg | Neg | Neg | Pos |
| Blood Vessel (endothelium) Examined in all tissues | | | Detailed under individual tissues | | | |
| Bone Marrow | Neg | Nag | Neg | Neg | Neg | Pos |
| Brain - Cerebellum | Neg | Neg | Neg | Neg | Neg | Pos |
| Brain - Cerebrum (cortex) | Neg | Neg | Neg | Neg | Neg | Pos |
| Breast (mammary gland) | Neg | Neg | Neg | Neg | Neg | Pos |
| Eye | Neg | Neg | Neg | Neg | Neg | Pos |
| Gastrointestinal Tract - Colon (large intestine) Submucosal lymphoid nodule (occasional follicular and interfollicular lymphocytes) | 2-3+ | 2-3+ | Neg | Neg | Neg | Pos |
| Gastrointestinal Tract - Colon (large intestine) Other elements | Neg | Neg | Neg | Neg | Neg | Pos |
| Gastrointestinal Tract - Esophagus | Neg | Neg | Neg | Neg | Neg | Pos |
| Gastrointestinal Tract - Small intestine | Neg | Neg | Neg | Neg | Neg | Pos |
| Gastrointestinal Tract - Stomach | Neg | Neg | Neg | Neg | Neg | Pos |
| Heart | Neg | Neg | Neg | Neg | Neg | Pos |
| Kidney (glomerulus, tubule) | Neg | Neg | Neg | Neg | Neg | Pos |
| Liver | Neg | Neg | Neg | Neg | Neg | Pos |
| Lung | Neg | Neg | Neg | Neg | Neg | Pos |
| Lymph Node | Neg | Neg | Neg | Neg | Neg | Pos |
| Ovary | Neg | Neg | Neg | Neg | Neg | Pas |
| Fallopian Tube (oviduct) | Neg | Neg | Neg | Neg | Neg | Pos |
| Pancreas | Neg | Neg | Neg | Neg | Neg | Pos |
| Parathyroid | Nag | Neg | Neg | Neg | Neg | Pos |
| Peripheral Nerve | Neg | Neg | Neg | Neg | Neg | Pos |
| Pituitary | Neg | Neg | Neg | Neg | Neg | Pos |
| Placenta | Neg | Neg | Neg | Neg | Neg | Pos |
| Prostate | Neg | Neg | Neg | Neg | Neg | Pos |
| Salivary Gland | Neg | Neg | Neg | Neg | Neg | Pos |
| Skin | Neg | Neg | Neg | Neg | Neg | Pos |
| Spinal Cord | Neg | Neg | Neg | Neg | Neg | Pos |
| Spleen | Neg | Neg | Neg | Neg | Neg | Pos |
| Striated (Skeletal) Muscle | Neg | Neg | Neg | Neg | Neg | Pos |
| Testis | Neg | Neg | Neg | Neg | Neg | Pos |
| Thymus | Neg | Neg | Neg | Neg | Neg | Pos |
| Thyroid | Neg | Neg | Neg | Neg | Neg | Pos |
| Tonsil Lymphocytes (occasional follicular, interfollicular and subepithelial lymphocytes) | 2+ | 1-2+ | Neg | Neg | Neg | Pos |
| Tonsil Other elements | Neg | Neg | Neg | Neg | Neg | Pos |
| Ureter | Neg | Neg | Neg | Neg | Neg | Pos |
| Urinary Bladder | Neg | Neg | Neg | Neg | Neg | Pos |
| Uterus - Body (endometrium) | Neg | Nei | Neg | Neg | Neg | Pos |
| Uterus - Cervix | Neg | Neg | Neg | Neg | Neg | Pos |

* omission of test antibody

D. Specific Reactivity of 10D.1 with Macaque CTLA-4

Specific reactivity with macaque CTLA-4 was demonstrated using T-cells transfected to express the macaque CTLA-4 at high levels (Table 5). These data suggest that the CTLA-4 epitope for 10D1 is conserved between macaque and humans, therefore macaque is a good model to evaluate in vivo safety of anti-CTLA4 HuMAb 10D1.

TABLE 5

| Species | reactivity of isotype control (MFI) | reactivity of 10D1 (MFI) |
|---|---|---|
| human CTLA4 | 3 | 662 |
| macaque CTLA4 | 4 | 606 |
| murine CTLA4 (negative control) | 5 | 5 |

MAb 10D1 (10 µg/ml) was incubated with cell lines expressing recombinant CTLA-4 from various species, and detected by FITC-anti human IgG. The cell-associated fluorescence was determined by FACScan and reported as mean fluorescence intensity (MFI). These data show that MAb 10D1 reacts well with macaque and human CTLA-4, but not with murine CTLA-4.

Example 6

10D1 Blocking of CTLA-4 to B7 Ligands

In order to show that 10D1 binding to CTLA-4 blocks the interaction of CTLA-4 with CTLA-4 ligands, B7.1 and B7.2, competition assays were performed by flow cytometry (FIG. 11 and FIG. 12). As shown in FIG. 11, FITC-labeled human B7.2-Ig fusion protein was incubated with 58αβCTLA4 T-cells and various concentrations of 10D1 MAb. In FIG. 12, FITC-labeled CTLA4-Ig fusion protein was incubated with murine B7.1 transfected cells and various concentrations of 10D1 MAb.

The competition assays demonstrate the ability of 10D1 to efficiently inhibit CTLA4-B7 interactions at low concentrations (1-10 µg/ml). The effective concentration would likely be much lower under physiological conditions, which would have far lower concentrations of CTLA-4 and B7 molecules. Similar data was obtained using biotinylated reagents in ELISA assays.

These in vitro studies demonstrate that MAb 10D1 binds human CTLA-4 with high affinity and specificity and that binding of 10D1 abrogates interaction between B7 costimulatory molecules and CTLA-4. These data for 10D1 are consistent with the in vitro activity profiles for anti-murine CTLA-4 antibodies that have demonstrated efficacy in murine tumor models.

Example 7

Epitope Mapping of 10D.1

Competitive ELISAs were done with biotin labeled and unlabeled antibodies to determine CTLA-4 epitope specificity. Four anti-CTLA-4 epitope binding groups were identified among the human antibodies, and an additional two epitopes were defined by the commercial murine monclonal antibodies BNI3 (Pharmingen, San Diego, Calif.), and 8H5 (Ancell Corp. Bayport, Mn). FIGS. 3, and 13A-13G show results of competitive binding assays that demonstrate differential competition among the antibodies for binding to CTLA-4. These results are summarized in Table 6.

Antibodies in anti-CTLA-4 epitope binding groups 4a and 4b have similar binding characteristics, and additionally are strong blockers of CTLA-4-Ig binding to cell surface expressed B7.1 (Table 6). For example, FIG. 3 shows results with biotin labeled 11E8 antibody and 10 unlabeled antibodies (3A4, 9A5, 2E2, 2E7, 4B6, 4E10, 5C4, 5G1, 11E8 and 11G1). Antibody 11E8 binding was blocked by itself and 7 of the other human antibodies in epitope groups 4a and 4b. However, binding of 11E8 was not blocked by antibodies 3A4 or 9A5 (epitope groups 1 and 2). Reciprocal binding experiments showed that 11E8 binding did not block either 9A5 or 3A4 binding to CTLA-4 (FIGS. 13A and 13B). Similar results are shown for epitope group 4a antibodies 10D1 and murine antibody 147 (FIGS. 13D and 13F). Antibodies in epitope group 4b (FIG. 13E) are similar to group 4a antibodies with the exception that the epitope 4b antibodies compete with epitope group 2 antibodies in reciprocal binding experiments (FIG. 13B). Human antibodies that belong to epitope groups 3, 4a and 4b are effective blockers of CTLA-4/B7.1 binding (FIG. 3, and Table 6).

TABLE 6

CTLA-4 MABs: Epitope and CTLA-4/B7.1 Blocking Properties

| Epitope | Monoclonal Antibody | Competition for CTLA-4 Binding | Blocks binding of CTLA-4-Ig to B7.1 on Ltk mB7.1 |
|---|---|---|---|
| 1 | 9A5 | No competition from groups 3, 4a, 4b, 5, and 6 Weak Competition form group 2 | No |
| 2 | 3A4 | One way competition from groups 1, 4b, 5 and 6 | No |
|   | 1E2 | No competition with 4a. Weak competition form group 3 |   |
| 3 | 5A8 | Competes with 4a and 4b. Some competition with 2. No competition form 1 and 5 | Yes |
| 4a | 10D1 | Cross competes with all members of 4b. | Yes |
|   | 147* | Competition from 6 (non-reciprocal) |   |
|   | 11E8 | No competition with 1, 2, and 5. |   |
|   | 11G1 | Weak competition with 3. |   |
|   | 4E10 |   |   |
|   | 5C4 |   |   |
|   | 3F10 |   |   |
| 4b | 4B6 | Cross competes with all members of 4a | Yes |
|   | 4A1 | Competes with 2 |   |
|   | 2E2 | Weak competition with 3. |   |
|   | 2E7 | No competition with 1, and 5. |   |
|   | 2G1 | Competition from 6 (non-reciprocal) |   |

TABLE 6-continued

CTLA-4 MABs: Epitope and CTLA-4/B7.1 Blocking Properties

| Epitope | Monoclonal Antibody | Competition for CTLA-4 Binding | Blocks binding of CTLA-4-Ig to B7.1 on Ltk mB7.1 |
|---|---|---|---|
| 5 | BNI3** | Competes with 6, no competition with groups 1 to 4 | Yes |
| 6 | 8H5*** | Competes with 5, no competition with groups 1 to 4 Competition with group 3 not tested | Yes |

*Murine monoclonal antibody
**Available from Pharmingen, BNI3 Catalog # 34580 D, San Diego CA.
***Available from Ancell, ANC 152.2/8H5 Catalog # 359-020, Ancell Corp. Bayport, Mn.

Example 8

10D1 Binds to Human Activated T Cells

The ability of 10D1 antibody to bind to CTLA-4 expressed by normal human T cells was investigated by flow cytometric analysis of resting and activated T cells (FIG. 14). Freshly isolated human peripheral blood mononuclear cells at $2\times10^6$/ml were incubated in the presence or absence of 2 ug/ml of the T-cell mitogen, phytohemagglutinin (PHA). After four days incubation, the cells were washed and stained with the following antibodies: 1) no antibody; 2) HuIgG1-FITC, a human IgG1 anti EGF receptor antibody; 3) 10D1-FITC, human IgG1 antiCTLA-4 antibody; and 4) 147-FITC—mouse anti-human CTLA-4 antibody. After incubation for 1 hr., cells were washed and stained with rabbit anti-FITC IgG followed by goat anti-rabbit-PE. Analysis was performed on lymphocytes gated by forward versus side scatter. As shown in FIG. 14, resting lymphocytes do not bind 10D1 antibody, while PHA-activated T cells express low levels of CTLA-4 at the cell surface Example 9

10D1 Does not Mediate Complement-Dependent or Antibody-Dependent Lysis of Activated T-cells The ability of MAb 10D1 to mediate complement-dependent cellular cytotoxicity (CDCC) or antibody-dependent cellular cytotoxicity (ADCC) of CTLA-4 expressing cells was investigated.

For CDCC experiments, rabbit serum was used as a source of compliment, in order to provide optimal conditions for CDCC. Rabbit complement has been shown to be more effective in mediating CDCC with human IgG$_1$ than human complement (Jurianz, Maslak et al., 1999). PHA-stimulated T-cells were labeled with $^{51}$Cr and incubated with various concentrations of anti-CTLA4 MAb 10D1 or anti-CD3 MAb with or without rabbit serum as a source of complement. After a 1 hour incubation, the $^{51}$Cr released by dying cells was determined using a gamma counter. Target cells incubated with 2% SDS served as 100% lysis controls. The anti-CTLA-4 MAb 10D1 did not mediate CDCC of the activated T-cells (FIG. 15). Under the same conditions, the murine IgG2, anti-CD3 MAb led to significant CDCC. Both murine IgG2$_a$ and human IgG$_1$ efficiently fix rabbit complement; therefore these differences most likely reflect the greatly reduced expression of CTLA-4 as compared to CD3 on activated T-cells.

Similarly, no ADCC activity was observed for MAb 10D1 using autologous mononuclear cells as effector cells (FIG. 16). PHA-stimulated T-cells were labeled with $^{51}$Cr and incubated with various concentrations of anti-CTLA4 MAb 10D1 or anti-CD3 MAb and fresh autologous mononuclear cells. The effector to target cell ratio was 100:1. After a 4 hour incubation, the $^{51}$Cr released by dying cells was determined using a gamma counter. Target cells incubated with 2% SDS served as 100% lysis controls. Although the anti-CD3 MAb is a murine IgG2$_a$, which can mediate efficient ADCC with human effector cells, only low levels of ADCC were observed. These data are consistent with the requirement of high levels of antigen expression on the surface of target cells for efficient ADCC. Since MAb 10D1 is a human IgG$_1$, an isotype generally capable of mediating CDCC and ADCC, the lack of these activities is likely due to the very low expression of CTLA-4 on activated T-cells. Furthermore, the observation of increased numbers of activated T-cells in the primate toxicology studies (see below) is consistent with the lack of ADCC and CDCC activity of activated T-cells by MAb 10D1 in vivo.

Example 10

10D1 Preclinical Toxicity Studies in Cynomolaus Monkeys

Two independent toxicology studies of 10D1 antibody and macaques were performed. A total of eight monkeys were analyzed. Four monkeys (two males and two females) tolerated three bolus i.v. doses of 3 mg/Kg human anti-CTLA4, and four monkeys (two males and two females) tolerated three bolus i.v. doses of 10 mg/Kg human anti-CTLA4 without significant clinical, immunotoxicology, or histopathological findings.

A. 10D1 Primate Toxicology Study (3.0 mg/Kg)

To investigate the effects of 10D1 in vivo, a primate toxicology study was performed with two macaques. In a multiple dose toxicity study of MAb 10D1, this antibody was administered via intravenous injection of macaques. The objective of this study was to determine the tolerability of MAb 10D1 in two monkeys given at a dose and schedule compatible with efficacious treatment in a murine tumor regression model and proposed dose in human clinical studies. Two female cynomolgus monkeys (Macaca fascicilaris) were treated with three intravenous bolus doses of 3.0 mg/Kg 10D1 on days 1, 4, and 7 to evaluate safety and T-cell activation in these animals. The animals were observed for any adverse reactions, weight loss/gain, and morbidity and mortality up to 14 days post administration of the first dose. Seven days after the last dose the animals were sacrificed and necropsied to examine their organs individually. Blood samples were collected before each dose and before necropsy for examination of T-cell populations and expression of activation markers by flow cytometry. Plasma was also collected from blood samples to determine 10D1 antibody levels and anti-10D1 antibody responses by ELISA.

The animals tolerated three doses of antibody 10D1 without any clinical symptoms during the treatment course. The weight of these animals did not change significantly. No gross findings were documented on 47 organs/tissues examined at necropsy for either animal.

Histopathology studies were performed at Redfield laboratories, Redfield, Ark. The results from these studies indicated that multiple doses of MAb 10D1 did not produce acute toxicity in any of the organs and tissues examined.

Pharmacokinetic analysis revealed the presence of significant levels (up to 97.3 μg/ml) of 10D1 MAb in the plasma of both monkeys (see Table 7). Plasma levels of 10D1 were determined by a competition assay with FITC-10D1 using flow cytometry and 58αβCTLA-4 T-cells.

TABLE 7

10D1 plasma levels

| Time point | Monkey #1 | Monkey #2 |
|---|---|---|
| Pre-1$^{st}$ dose | 0.0 (μg/ml plasma) | 0.0 (μg/ml plasma) |
| Day 4, pre-2$^{nd}$ dose | 17.4 (μg/ml plasma) | 43.6 (μg/ml plasma) |
| Day 7, pre-3$^{rd}$ dose | 83.6 (μg/ml plasma) | 97.3 (μg/ml plasma) |
| Day 14 | 90.2 (μg/ml plasma) | 70.9 (μg/ml plasma) |

Evaluation of the anti-10D1-antibody response was performed by ELISA. No significant anti-10D1 response was observed in either animal during the course of study (FIG. 17). Microtiter plates were coated with 10D1 MAb (for IgM assay) or 10D1 F(ab')$_2$ (for IgG assay). Dilutions of plasma samples from various time points were incubated with the plates, and anti-10D1 antibodies were detected with either anti-IgM or IgG Fc-specific alkaline phosphatase reagents. IgM anti-10D1 antibodies appear to have developed by day 14, however, the titers are very low. IgM anti-10D1 antibodies appear to have developed by day 14, however, the titers are very low. These data demonstrate that the monkeys did not develop anti-10D1 antibody responses after 3 doses of the antibody.

These data demonstrate that the animals did not develop a significant antibody response against MAb 10D1 during the course of this study.

Immunotoxicology was investigated by flow cytometric analysis of lymphocyte populations during the course of the study. The lymphocyte subsets examined included CD3 as a marker for total T-cells and CD20 as a marker for total B-cells. T-cells, were further subdivided for expression of CD4 (helper T-cell marker) and CD8 (cytotoxic T-cell marker), as well as for activation markers CD25, CD29, CD69 and HLA-DR. No remarkable changes in T-cell populations or expression of activation markers was noted. The results are summarized in Table 8 below.

TABLE 8

Flow cytometric analysis of lymphocyte populations

| Time point | Monkey #1 | Monkey #2 |
|---|---|---|
| Pre-1$^{st}$ dose | % CD3 = 61, % CD20 = 16 | % CD3 = 54, % CD20 = 22 |
| | % CD4 = 43, % CD8 = 50 | % CD4 = 59, % CD8 = 36 |
| | % CD25 ≤ 1, % CD29 = 41 | % CD25 ≤ 1, % CD29 = 29 |
| | % CD69 = <1, % HLA-DR = 4 | % CD69 ≤ 1, % HLA-DR = 1 |
| Day 4, pre-2$^{nd}$ dose | % CD3 = 58, % CD20 = 13 | % CD3 = 56, % CD20 = 16 |
| | % CD4 = 38, % CD8 = 52 | % CD4 = 62, % CD8 = 37 |
| | % CD25 ≤ 1, % CD29 = 52 | % CD25 ≤ 1, % CD29 = 36 |
| | % CD69 ≤ 1, % HLA-DR = 2 | % CD69 ≤ 1, % HLA-DR ≤ 1 |
| Day 7, pre-3$^{rd}$ dose | % CD3 = 59, % CD20 = 15 | % CD3 = 51, % CD20 = 17 |
| | % CD4 = 47, % CD8 = 59 | % CD4 = 51, % CD8 = 39 |
| | % CD25 = 2, % CD29 = 44 | % CD25 = 1, % CD29 = 39 |
| | % CD69 = 1, % HLA-DR = 4 | % CD69 = 1, % HLA-DR = 2 |
| Day 14 | % CD3 = 64, % CD20 = 14 | % CD3 = 59, % CD20 = 20 |
| | % CD4 = 49, % CD8 = 44 | % CD4 = 60, % CD8 = 35 |
| | % CD25 = 1, % CD29 = 44 | % CD25 ≤ 1, % CD29 = 34 |
| | % CD69 ≤ 1, % HLA-DR = 15 | % CD69 ≤ 1, % HLA-DR = 1 |

Heparinized blood samples were analyzed fresh by flow cytometry using FITC- or PE-labeled anti-lymphocyte reagents. % CD3 and % CD20 are based on a lymphocyte gate. The additional T-cell markers and activation markers are all based on CD3-positive cells. These data indicate that multiple doses of MAb 10D1 does not have a significant effect on B and T-cell populations or T-cell activation markers.

B. 10D1 Primate Toxicology Study (3.0 and 10.0 mg/Kg)

Six cynomolgus monkeys (four males and two females), experimentally non-naïve and weighing 2.4 to 3.8 kg at the outset of the study, were assigned to treatment groups as shown in Table 9 below.

TABLE 9

| Group No. | Number of Males/Females | Dose Level (mg/kg) | Dose Vol. (ml/kg) | Dose Solution Conc. mg/ml |
|---|---|---|---|---|
| 1 | 2/0 | 3 | 0.6 | 5.0 |
| 2 | 2/2 | 10 | 2.0 | 5.0 |

Each animal received a dose of human anti-CTLA4 (5 mg/ml concentration) by intravenous injection (i.e., "slow-push" bolus injection) every three days for one week (i.e., on Days 1, 4 and 7). Detailed clinical observations were conducted at least twice daily ("cageside observations"), and a thorough physical examination was performed on each animal prior to the study and on Day 12. Body weights were measured weekly (prestudy and Days 7 and 14), and ophthalmoscopic examination was conducted on all animals prior to the study and on Day 12. Blood samples for evaluation of serum chemistry, hematology and coagulation parameters were collected from all animals prestudy and on Day 14. Additional samples for selected hematology parameters (total and differential white blood cells only) were collected prior to dosing on each dosing day (Days 1, 4, and 7). Urine samples for standard urinalysis were obtained by drainage from specially designed cage-pans prior to dosing and on Day 13. Blood samples were also collected prior to each dose (Days 1, 4 and 7) and prior to termination (Day 14) for various analyses conducted by Medarex. These included analysis of test article concentration (pharmacokinetics), determination of the presence of antibodies to the test article, and flow cytometry analysis. All animals were euthanized on Day 14, at which time, a complete gross necropsy was conducted, major organs were weighed, and a standard complete set of tissues was collected from each animal and processed for examination by light microscopy.

Intravenous administration of human anti-CTLA4 at dose levels of 3 mg/kg and 10 mg/kg given every three days for a total of three doses was very well tolerated by cynomolgus monkeys. There were no clinical signs of toxicity from the cageside observations and physical examinations, and no effects on body weight, ocular examination findings, clinical pathology parameters, gross necropsy findings, organ weights or tissue histomorphology.

The results of the analysis of test article concentration in serum samples (i.e., trough levels measured in samples obtained prior to dosing on Days 4 and 7, and prior to necropsy on Day 14) indicated dose-dependent exposure to the test article. On Day 7, predose mean concentrations were approximately 84 and 240 µg/ml for the 3- and 10-mg/kg dose groups, respectively.

A potential for accumulation of the test article in serum with the every-three-day dosing schedule in monkeys was evident from the difference between the Day 4 and Day 7 trough levels (i.e., means concentrations on Day 7 were approximately twice as high as on Day 4), as well as from the high residual levels on Day 14 (one week after the last dose), which were similar to the Day 7 trough levels. Evidence of antibody formation against the test article was detected in two of the six study animals (one from Group 1 and another from Group 2). In the former case, it appeared that the antibody response might have affected the clearance of the test article from circulation. Flow cytometric analysis of lymphocyte subsets revealed a modest increase in total CD3-positive cells between Days 1 and Day 14, which correlated with an increase in CD3/CD4-positive cells, and a respective decrease in CD3/CD8-positive cells (Group 2 only). The percentage of CD3 cells expressing CD29 and HLA-DR moderately increased over the course of the study, which was consistent with previous findings that anti-CTLA4 antibodies can enhance antigen-specific T-cells.

In conclusion, apart from the minor changes in circulating lymphocyte subpopulations, the highest dose level tested in this study (i.e., three doses of 10 mg/kg given at three-day intervals) was an absolute no-effect dose level in cynomolgus monkeys.

Example 11

A Phase I Human Clinical Trial of MAb 10D1 in Prostate Cancer (MDXCTLA4-01) and Melanoma (MDXCTLA4-02)

MDXCTLA4-01 is an open-label study of anti-cytotoxic T-lymphocyte-associated antigen-4 (anti-CTLA-4) monoclonal antibody 10D1 (MAb 10D1) in patients with progressive, metastatic, hormone-refractory prostate cancer. Treatment is a single dose of MAb 10D1 that is administered intravenously, as an infusion, at a dosage of 3.0 mg/Kg. The objectives of this trial are to determine if i. administration of MAb 10D1 causes nonspecific T-cell activation, ii. to establish a safety/tolerability profile for MAb 10D1 in these patients and, iii. to determine the pharmacokinetic profile of MAb 10D1 and assess the development of a host immune response to MAb 10D1. In addition the study will attempt to identify preliminary evidence of efficacy. The study is a multicenter, open-label study of a single dose of MAb 10D1 in 14 subjects. The study consists of four phases: Screening, Infusion, Post-infusion, and Follow-up (see Table 10 below).

Patients with histologic diagnosis of primary adenocarcinoma of the prostate, and progressive metastatic carcinoma of the prostate after androgen deprivation and at least one systemic non-hormonal manipulation, are being screened for participation in this study. Subjects must have progressive measurable disease, progressive PSA, PSA>5 ng/ml, testosterone<50 ng/dl, primary gonadal androgen suppression, life expectancy>12 weeks, and Karnofsky Performance Status≥60%.

Subjects undergo physical examination, ECG, chest radiography, diagnostic imaging, and blood sampling for hematological, biochemical, and immune function assessments, and have vital signs monitored. Monthly telephone interviews are used to collect and record information on a subset of adverse events, including autoimmune adverse events after disease progression, until six months after treatment. PSA (decline, duration of decline, progression, time to progression) and disease response (complete, partial, stable, progressive) are monitored. Plasma concentrations of MAb 10D1 are being assessed immediately prior to, during, and up to two months after, infusion.

Data from four prostate cancer subjects that have been treated are shown in Table 11. No adverse events have been recorded. For all of the subjects treated, MAb 10D1 appears to be well tolerated.

Because of the importance of monitoring the immune status of patients in the trial and the specific goal of monitoring generalized effects on T cell activation by anti-CTLA-4 antibody, the entry criteria in this study included minimum levels of CD4 and CD8 T cells of 500/ml and ≥500/ml respectively. However, it was observed during the initial accrual in the study that prostate cancer patients have significantly reduced T cell numbers although CD4 and CD8 T cells are clearly present. Many patients were initially rejected based on the above entry criteria (see Table 11). The apparent reduced T cell counts observed is a previously undocumented observation in prostate cancer patients that may have relevance in treatments involving cancer vaccination in these patients. Subsequent to these observations, the entry criteria were amended to include patients having CD4 and CD8 count of ≥300/ml and ≥200/ml respectively.

In order to evaluate whether administration of MAb 10D1 can induce undesirable non-specific T cell activation, peripheral blood lymphocytes from the prostate cancer subjects were analyzed by flow cytometry for each of the following markers: CD4, CD8, CD25, CD44, CD69 and HLA-DR. Blood samples were taken at time points indicated in Table 10. No significant change in the frequency of any of these markers was observed during the course of the treatment for each of the prostate cancer subjects treated thus far. An example of this analysis is shown in Table 12 which shows the frequency of CD4, CD25, CD69-positive cells and CD8, CD25, CD69-positive cells at times prior to, during, and subsequent to MAb 10D1 administration in two of the subjects. These data demonstrate that MAb 10D1 does not result in non-specific T cell activation.

TABLE 10

| Phase | Screen | Infusion | Post-infusion | | | | | | | | Follow-up | | | |
| --- | --- | --- | --- | --- | --- | --- | --- | --- | --- | --- | --- | --- | --- | --- |
| Time | days −14 to 0 | −30 to 130 min | 145 min | 160 min | 190 min | 250 min | 370 min | 24 hrs | 48 his | 72 hrs | day 7 | day 14 | day 21 | day 28 | monthly |

TABLE 11

Study No. MDXCTLA4-01
Selected Lab Values Summary

| Screen no. | Subject no. | Initials | Amend- ment # | Day | Date | PSA ng/ml | Platelets ×10³/ul | WBC ×10³/ul | Neuts % | Neuts ×10³/ul | Lymphs % | Lymphs ×10³/ul |
|---|---|---|---|---|---|---|---|---|---|---|---|---|
| 02001 | 001 | JGR | | Scr | | 144.80 | 263 | 8.12 | 73.00 | 5.90 | 18.00 | 1.47 |
| 02001 | 001 | JGR | | 0 | | 185.20 | 267 | 5.74 | 66.00 | 3.79 | 22.00 | 1.32 |
| 02001 | 001 | JGR | | 1 | | | 259 | 6.31 | 69.00 | 4.38 | 20.00 | 1.29 |
| 02001 | 001 | JGR | | 2 | | | 240 | 6.59 | 70.00 | 4.66 | 19.00 | 1.31 |
| 02001 | 001 | JGR | | 3 | | | 270 | 6.53 | 71.00 | 4.63 | 21.00 | 1.36 |
| 02001 | 001 | JGR | | 7 | | 257.40 | 299 | 6.70 | 68.00 | 4.56 | 23.00 | 1.53 |
| 02001 | 001 | JGR | | 14 | | 332.30 | 308 | 6.87 | 71.90 | 7.94 | 21.20 | 1.39 |
| 02001 | 001 | JGR | | 21 | | | 286 | 9.72 | 74.00 | 7.20 | 19.70 | 1.91 |
| 02001 | 001 | JGR | | 28 | | 351.00 | 304 | 5.38 | 63.00 | 3.40 | 26.00 | 1.44 |
| 01002 | | JWF | | Scr | | 28.30 | 271 | 11.60 | 75.40 | 8.75 | 13.60 | 1.58 |
| 01003 | | MZB | | Scr | | 12.70 | 178 | 5.49 | 69.00 | 3.79 | 19.60 | 1.08 |
| 01004 | | TEQ | | Scr | | 1459.00 | 264 | 6.26 | 75.10 | 4.70 | 14.40 | 0.90 |
| 01005 | | WMN | | Scr | | 192.40 | 212 | 6.85 | 73.70 | 5.05 | 17.40 | 1.20 |
| 01006 | | MRS | | Scr | | 4503.00 | 140 | 7.55 | 76.70 | 5.79 | 15.90 | 1.20 |
| 01007 | | TAB | | Scr | | 1394.00 | 205 | 5.78 | 73.00 | 4.24 | 13.00 | 0.76 |
| 01008 | | CHB | | Scr | | 70.70 | 229 | 4.67 | 54.00 | 2.56 | 32.00 | 1.52 |
| 01009 | 003 | RAB | | Scr | | 238.60 | 144 | 3.70 | 78.00 | 2.88 | 14.00 | 0.55 |
| 01009 | 003 | RAB | | 0 | | 336.90 | 123 | 3.92 | 68.00 | 2.67 | 21.00 | 0.83 |
| 01009 | 003 | RAB | | 1 | | | 122 | 3.35 | 71.00 | 2.38 | 22.00 | 0.74 |
| 01009 | 003 | RAB | | 2 | | | 109 | 4.06 | 74.00 | 2.99 | 19.00 | 0.77 |
| 01009 | 003 | RAB | | 3 | | | 114 | 3.79 | 70.00 | 2.67 | 21.00 | 0.81 |
| 01009 | 003 | RAB | | 7 | | 249.30 | 69 | 3.38 | 75.00 | 2.54 | 17.00 | 0.60 |
| 01009 | 003 | RAB | | 14 | | 269.80 | 101 | 3.68 | 69.00 | 2.54 | 21.20 | 0.78 |
| 01009 | 003 | RAB | | 21 | | | 122 | 4.82 | 78.00 | 3.76 | 13.20 | 0.64 |
| 01012 | 004 | CEH | | Scr | | 112.90 | 172 | 5.85 | 64.00 | 3.74 | 28.00 | 1.69 |
| 01012 | 004 | CEH | | 1 | | | | | | | | |
| 01012 | 004 | CEH | | 2 | | | 150 | 4.82 | 67.70 | 3.26 | 28.40 | 1.28 |
| 01012 | 004 | CEH | | 3 | | | 147 | 4.36 | 63.70 | 2.78 | 29.30 | 1.28 |
| 01012 | 004 | CEH | | 7 | | 190.00 | 159 | 4.95 | 58.60 | 2.90 | 32.70 | 1.61 |
| 01012 | 004 | CEH | | 14 | | 207.60 | 199 | 5.64 | 63.10 | 3.55 | 29.30 | 1.65 |
| 01013 | | KJF | | Scr | | 49.10 | 228 | 8.53 | 65.00 | 5.62 | 26.00 | 2.23 |
| 02014 | 002 | L-S | | Scr | | 12.70 | 222 | 5.65 | 53.00 | 3.01 | 34.00 | 1.92 |
| 02014 | 002 | L-S | | 0 | | 27.50 | 217 | 5.88 | 57.00 | 3.36 | 32.00 | 1.88 |
| 02014 | 002 | L-S | | 1 | | | 226 | 5.74 | 55.00 | 3.19 | 35.00 | 2.04 |
| 02014 | 002 | L-S | | 2 | | | 223 | 5.59 | 55.00 | 3.09 | 32.00 | 1.84 |
| 02014 | 002 | L-S | | 3 | | | 219 | 4.89 | 54.00 | 2.66 | 34.00 | 1.68 |
| 01016 | Ineligible | G-F | | Scr | | 4856.00 | 106 | 7.31 | 86.00 | 6.29 | 5.00 | 0.33 |
| | | | normal range | | low | | 150 | 3.80 | 40.50 | 1.96 | 15.40 | 0.80 |
| | | | | | high | 7.00 | | 10.70 | 75.00 | 7.23 | 48.50 | 3.00 |

| Screen no. | Monos % | Monos ×10³/ul | Eos % | Eos ×10³/ul | CD4/ ul | CD8/ ul | ESR mm/hr | Hgb g/dl | Hcrit % |
|---|---|---|---|---|---|---|---|---|---|
| 02001 | 5.60 | 0.46 | 1.80 | 0.15 | 670 | 367 | 71 | 10.4 | 30 |
| 02001 | 6.60 | 0.38 | 3.10 | 0.18 | 704 | 376 | | 10.6 | 32 |
| 02001 | 8.70 | 0.55 | 0.90 | 0.00 | A | A | | 9.5 | 30 |
| 02001 | 6.70 | 0.44 | 1.80 | 0.12 | 556 | 303 | | 9.5 | 28 |
| 02001 | 5.50 | 0.36 | 2.20 | 0.14 | 608 | 254 | | 9.3 | 28 |
| 02001 | 6.00 | 0.46 | 2.50 | 0.17 | A | A | | 9.5 | 28 |
| 02001 | 5.21 | 0.36 | 1.90 | 0.13 | A | A | | 8.8 | 25 |
| 02001 | 4.80 | 0.46 | 1.00 | 0.10 | A | A | | 9.1 | 28 |
| 02001 | 5.80 | 0.31 | 2.90 | 0.16 | | | | 8.7 | 25 |
| 01002 | 5.70 | 0.66 | 4.60 | 0.53 | 399 | 189 | 41 | 13.9 | 37 |
| 01003 | 6.30 | 0.35 | 2.70 | 3.24 | 325 | 168 | 19 | 12.7 | 36 |
| 01004 | 7.70 | 0.48 | 2.40 | 0.15 | 365 | 129 | 61 | 12.8 | 36 |
| 01005 | 6.20 | 0.43 | 2.20 | 0.15 | 483 | 217 | | | |
| 01006 | 6.20 | 0.47 | 0.80 | 0.06 | 319 | 363 | 83 | | |
| 01007 | 6.50 | 0.37 | 6.00 | 0.35 | 376 | 127 | | 14.1 | 43 |
| 01008 | 8.30 | 0.39 | 3.40 | 0.16 | 461 | 499 | | 15.6 | 45 |
| 01009 | 5.40 | 0.20 | 1.20 | 0.04 | 211 | 162 | 43 | 9.8 | 30 |
| 01009 | 8.70 | 0.34 | 1.50 | 0.06 | 374 | 188 | | 10.9 | 31 |
| 01009 | 4.00 | 0.14 | 1.80 | 0.06 | 307 | 192 | | 11.3 | 32 |
| 01009 | 4.80 | 0.20 | 1.20 | 0.05 | 328 | 220 | | 11.3 | 33 |
| 01009 | 6.20 | 0.23 | 1.30 | 0.05 | 313 | 266 | | 10.9 | 31 |
| 01009 | 5.60 | 0.19 | 0.70 | 0.02 | 244 | 161 | | 10.4 | 30 |
| 01009 | 8.50 | 0.31 | 1.00 | 0.04 | 308 | 173 | | 8.8 | 25 |
| 01009 | 7.70 | 0.37 | 0.60 | 0.03 | 218 | 195 | | 7.4 | 20 |
| 01012 | 5.60 | 0.33 | 1.00 | 0.06 | 746 | 451 | 10 | 13.2 | 40 |
| 01012 | | | | | 642 | 475 | | | |
| 01012 | 4.60 | 0.22 | 1.10 | 0.05 | 552 | 380 | | 12.2 | 36 |
| 01012 | 5.10 | 0.22 | 1.30 | 0.06 | 544 | 441 | | 13.1 | 37 |
| 01012 | 5.90 | 0.29 | 2.50 | 0.12 | 842 | 506 | | 12.6 | 35 |

TABLE 11-continued

Study No. MDXCTLA4-01
Selected Lab Values Summary

| | | | | | | | | | |
|---|---|---|---|---|---|---|---|---|---|
| 01012 | 5.70 | 0.32 | 1.60 | 0.09 | | | | 13.5 | 38 |
| 01013 | 5.30 | 0.46 | 2.30 | 0.20 | 1213 | 398 | | 13.4 | 37 |
| 02014 | 7.40 | 0.42 | 3.90 | 0.22 | 721 | 439 | | 13.6 | 40 |
| 02014 | 8.60 | 0.50 | 1.50 | 0.09 | 676 | 389 | | 13.5 | 38 |
| 02014 | 7.00 | 0.40 | 1.40 | 0.08 | 632 | 405 | | 13.6 | 38 |
| 02014 | 9.80 | 0.55 | 1.40 | 0.09 | 590 | 339 | | 13.5 | 39 |
| 02014 | 7.50 | 0.37 | 2.70 | 0.13 | 529 | 358 | | 13.2 | 37 |
| 01016 | 6.80 | 0.49 | 1.90 | 0.14 | 57 6 | 7 | | 10.3 | 31 |
| | 2.60 | 0.12 | | | 404 | 220 | | | |
| | 10.00 | 0.92 | 6.80 | 0.57 | 1612 | 1128 | 30 | | |

TABLE 12

Flow cytometric analysis of T cell activation markers in prostate cancer subjects treated with 3.0 mg/Kg MAb 10D1.

| Patient Number | Time Point | CD (4 + 25 + 69) % | CD (8 + 25 + 69) % |
|---|---|---|---|
| 3 | Screen | 1.7 | 0.8 |
| 3 | −30 MIN (Pre-Infusion) | 2.6 | 0.8 |
| 3 | 40 MIN | 2.5 | 0.7 |
| 3 | 130 MIN | 1.9 | 0.9 |
| 3 | 145 MIN | 1.7 | 0.5 |
| 3 | 160 MIN | 1.7 | 1 |
| 3 | 190 MIN | 1.5 | 1.5 |
| 3 | 250 MIN | 2.1 | 1.2 |
| 3 | 370 MIN | 1.3 | 0.9 |
| 3 | 24 HR | 1.6 | 1.6 |
| 3 | 48 HR | 2.7 | 3 |
| 3 | 72 HR | 0.9 | 0.5 |
| 3 | Day 7 | 0.9 | 0.1 |
| 3 | Day 14 | 0.4 | 0.5 |
| 3 | Day 21 | 2.3 | 1.9 |
| 4 | Screen | 1.4 | 0.8 |
| 4 | −30 MIN (Pre-Infusion) | 0.5 | 0.3 |
| 4 | 40 MIN | 0.3 | 0.1 |
| 4 | 130 MIN | 0.3 | 0.1 |
| 4 | 145 MIN | 0.4 | 0.2 |
| 4 | 160 MIN | 0.2 | 0.2 |
| 4 | 190 MIN | 0.8 | 0.3 |
| 4 | 250 MIN | 0.1 | 0 |
| 4 | 370 MIN | 0.3 | 0.1 |
| 4 | 24 HR | 0.2 | 0.3 |
| 4 | 48 HR | 0.4 | 0.6 |
| 4 | 72 HR | 0.8 | 0.3 |
| 4 | Day 7 | 1 | 0.7 |
| 4 | Day 14 | 1.1 | 0.8 |

A second clinical trial (MDXCTLA4-02) using MAb 10D1 in subjects with Stage 1V malignant melanoma has also been initiated. A single dose of MAb 10D1 will be administered intravenously, as an infusion, at a dosage of 3.0 mg/Kg. This study also consists of four phases (Screening, Infusion, Post-Infusion and Follow-up) as described in Table 9, above.

The goals of this study are as those regarding the above-described study in prostate cancers as well as to specifically establish a safety/tolerability profile for MAb 10D1 in patients with Stage 1V malignant melanoma. One patient has been treated in this study (see Table 13). As in the prostate cancer study, MAb 10D1 appears to be well tolerated. Flow cytometric analysis of T cell activation markers in this subject, analogous to that performed for the prostate tumor trial, also showed no evidence of non-specific T cell activation,

TABLE 13

Study No. MDXCTLA4-02
Selected Lab Values Summary

| Screen no. | Subject no. | Initials | Amendment # | Day | Date | Platelets ×10³/ul | WBC ×10³/ul | Neuts % | Neuts ×10³/ul | Lymphs % | Lymphs ×10³/ul | Monos % | Monos ×10³/ul |
|---|---|---|---|---|---|---|---|---|---|---|---|---|---|
| 02001 | 001 | SAH | 0 | Scr | | 216 | 6.28 | 56.60 | 3.52 | 35.60 | 2.23 | 5.90 | 0.37 |
| 02001 | 001 | SAH | 0 | 0 | | 230 | 5.58 | 59.70 | 3.33 | 32.30 | 1.80 | 5.70 | 0.32 |
| 02001 | 001 | SAH | 0 | 1 | | 202 | 5.12 | 61.80 | 3.16 | 30.20 | 1.55 | 5.00 | 0.26 |
| | | | normal range | | low | 150 | 3.80 | 40.50 | 1.96 | 15.40 | 0.80 | 2.60 | 0.12 |
| | | | | | high | | 10.70 | 75.00 | 7.23 | 48.50 | 3.00 | 10.10 | 0.92 |

| Screen no. | Subject no. | Initials | Amendment # | Day | Date | Eos % | Eos ×10³/ul | CD4/ ul | CD8/ ul | ESR mm/hr | Hgb g/dl | Hcrit % |
|---|---|---|---|---|---|---|---|---|---|---|---|---|
| 02001 | 001 | SAH | 0 | Scr | | 1.80 | 0.11 | 1189 | 631 | | 14.4 | 39 |
| 02001 | 001 | SAH | 0 | 0 | | 1.80 | 0.10 | 1039 | 502 | | 14.9 | 43 |
| 02001 | 001 | SAH | 0 | 1 | | 2.30 | 0.12 | 957 | 407 | | 13.4 | 37 |
| | | | normal range | | low | | | 404 | 220 | | | |
| | | | | | high | 6.80 | 0.57 | 1612 | 1129 | 30 | | |

Ongoing results from the MDXCTLA4-0 I and MDX-CTLA4-02 clinical trials have demonstrated that the infusions are tolerable with only minor reactions. Prolonged plasma half-life of the antibody was seen, with the antibody remaining in the plasma for approximately 3 to 4 months. Clear evidence of immune effects was observed without overt non-specific T cell activation. Symptomatic relief and reductions in prostate specific antigen (PSA) levels have been observed in prostate cancer patients treated with the anti-CTLA-4 antibody. Representative results for reductions in PSA levels are shown in FIG. 18, which shows PSA levels (in ng/ml) in two patients (one represented by the closed circles, the other by the open circles) at various time points after infusion of 3 mg/kg anti-CTLA-4 antibody at day 0. The results demonstrate that PSA levels decreased after infusion of the antibody and remained suppressed for approximately 3-4 months after treatment, correlating with the presence of the anti-CTLA-4 antibody in the plasma. Other examples of immune effects observed included immune-mediated rash and pruritis, transient seroconversion to positive autoantibodies, melanin pigment changes in melanoma patients and inflammatory reactions at tumor sites. Except for the rash and pruritis, all potentially adverse immune effects were subclinical. In summary, the ongoing results from human clinical trials with anti-CTLA-4 antibody treatment demonstrate that the antibody is well-tolerated and stimulates immune effects in recipients.

Example 12

Anti-CTLA-4 Treatment Enhances Antibody Responses to a Hepatitis B Surface Antigen (HBsAg) Vaccine The ability of a human anti-CTLA-4 antibody of the invention to enhance antibody responses to a hepatitis B surface antigen (HBsAg) vaccine was examined in cynomolgus monkeys. Test groups of four monkeys each (two males, two females) were treated with either 1) the HBsAg vaccine in combination with a control IgG1 antibody (a humanized anti-RSV antibody, Synagis™, commercially available from MedImmune) or 2) the HbsAg vaccine in combination with the anti-CTLA-4 antibody 10D1. The anti-CTLA-4 antibody or control IgG1 were administered intravenously at a dosage of 10 mg/kg in a volume of 2.0 ml/kg. The HBsAg vaccine (Engerix-B™, commercially available from GlaxoSmithKline) was administered intramuscularly at a dosage of 10 mg in a volume of 0.5 ml. The anti-CTLA-4 or control IgG1 antibody was administered on days 1 and 29, whereas the HBsAg vaccine was administered on days 2 and 30. Plasma levels of anti-HBsAg antibody were measured on days 1, 51 and 64 using a radioimmunoassay kit (commercially available from Abbott). Results presented represent the mean of the four animals in each group, +/−SE. The results are shown in the bar graphs of FIG. 19, wherein Group 1 was treated with vaccine and control IgG1 and Group 2 was treated with vaccine and anti-CTLA-4. The left bar for each group represents day 1, the middle bar represents day 51 and the right bar represents day 64. Use of the anti-CTLA-4 antibody in combination with the vaccine led to a significantly greater anti-HBsAg antibody response than use of the vaccine with a control IgG1. These results demonstrate that a human anti-CTLA-4 antibody of the invention is capable of enhancing antibody responses to a viral antigen vaccine in vivo in primates.

Example 13

Anti-CTLA-4 Treatment Enhances Antibody and T Cell Responses to a Melanoma Cell Vaccine The ability of a human anti-CTLA-4 antibody of the invention to enhance antibody and T cell responses to a melanoma cell vaccine was examined in cynomolgus monkeys. Test groups of six monkeys each (three males, three females) were treated with either 1) a melanoma cell vaccine alone (SK-mel-3, a human melanoma tumor cell line transfected to express GM-CSF) or 2) both SK-mel-3 and the anti-CTLA-4 antibody 10D1. The antibody was administered intravenously at a dosage of 10 mg/kg in a volume of 1.3 ml/kg. The SK-mel-3 cells were administered subcutaneously in a fixed amount ($5 \times 10^6$ cells/animal at 0.5 ml/animal). The appropriate antibody and/or vaccine were administered on days 0, 28, 56 and 84. Antibody responses to the melanoma cell vaccine were assessed on days 13, 41, 69 and 97. The results are shown in the graph of FIG. 20, in which a 1/1000 dilution of plasma was examined. Results presented represent the mean of the six animals in each group, +/−SE. Results from the animals treated with the vaccine alone are depicted with the open circles, whereas results from animals treated with both the anti-CTLA-4 antibody and the vaccine are depicted with closed circles. Use of the anti-CTLA-4 antibody in combination with the vaccine led to a significantly greater antibody response against the melanoma cells than use of the vaccine alone. These results demonstrate that a human anti-CTLA-4 antibody of the invention is capable of enhancing antibody responses to a tumor cell vaccine in vivo in primates.

The effect of anti-CTLA-4 treatment on antigen-specific T cell proliferation was also examined. Prior to vaccination of the animals, blood was drawn and monocytes from the animals were differentiated in vitro into dendritic cells (DC) to provide a population of autologous dendritic cells for use in T cell proliferation studies. A portion of theses autologous DCs were incubated with the SK-mel-3 cells to provide a population of autologous DCs that had been pulsed with melanoma antigens. At various time points after vaccination, polymorphonuclear cells (PMNC) were obtained from the animals and incubated in vitro either 1) alone (as a negative control), 2) with *Staphylococcus* enterotoxin B (SEB, a non-specific activator of certain T cell populations, as a positive control), 3) with autologous dendritic cells or 4) with autologous dendritic cells that had been pulsed with melanoma antigens. T cell proliferation was assessed using a quantitative flow cytometry assay that allowed for a quantitative measure of the total number of T cells per well (through the use of an anti-CD3 antibody), as well as the number of $CD8^-$ vs. $CD8^+$ cells (through the use of an anti-CD8 antibody). The results from an animal treated with SK-mel-3 in combination with anti-CTLA-4, assessed at day 41 after vaccination, are summarized in FIG. 21, wherein T cell proliferation is expressed as a stimulation index relative to the number of control unstimulated cells (set at a stimulation index of one). As illustrated in FIG. 21, stimulation with the non-specific activator SEB increased the stimulation index at least 5 fold in both $CD8^+$ and $CD8^-$ cells, whereas incubation with autologous dendritic cells alone increased the stimulation index only very slightly. Incubation with autologous dendritic cells pulsed with melanoma cell antigens also increased the stimulation index at least 5 fold in both $CD8^+$ and $CD8^-$ cells (the latter essentially corresponding to the $CD4^+$ T cell population), thereby indicating that vaccination with the melanoma cell vaccine in combination with anti-CTLA-4 results in antigen-specific T cell proliferation of both $CD8^+$ and $CD4^+$ T cells.

Further evidence of antigen-specific T cell proliferation was obtained from delayed type hypersensitivity (DTH) experiments. Animals treated with either the melanoma vaccine alone or with the melanoma vaccine in combination with the anti-CTLA-4 antibody were tested for a DTH reaction to either SK-mel-3 or to a saline control using standard DTH assay methods. The results demonstrated that 3 of 6 of the animals treated with the combination of the vaccine and the anti-CTLA-4 antibody exhibited a specific DTH response to the SK-mel-3 cells, whereas only one of the 6 animals treated with the vaccine alone exhibited a specific DTH response to the SK-mel-3 cells. These results further demonstrate the ability of anti-CTLA-4 antibody treatment to enhance antigen-specific T cell responses in vivo in primates.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

APPENDIX

SEQUENCE LISTING

SEQ ID NO: 1 pGP1k

```
AATTAGCGGC CGCTGTCGAC AAGCTTCGAA TTCAGTATCG ATGTGGGGTA    50
CCTACTGTCC CGGGATTGCG GATCCGCGAT GATATCGTTG ATCCTCGAGT   100
GCGGCCGCAG TATGCAAAAA AAAGCCCGCT CATTAGGCGG GCTCTTGGCA   150
GAACATATCC ATCGCGTCCG CCATCTCCAG CAGCCGCACG CGGCGCATCT   200
CGGGCAGCGT TGGGTCCTGG CCACGGGTGC GCATGATCGT GCTCCTGTCG   250
TTGAGGACCC GGCTAGGCTG GCGGGGTTGC CTTACTGGTT AGCAGAATGA   300
ATCACCGATA CGCGAGCGAA CGTGAAGCGA CTGCTGCTGC AAAACGTCTG   350
CGACCTGAGC AACAACATGA ATGGTCTTCG GTTTCCGTGT TTCGTAAAGT   400
CTGGAAACGC GGAAGTCAGC GCCCTGCACC ATTATGTTCC GGATCTGCAT   450
CGCAGGATGC TGCTGGCTAC CCTGTGGAAC ACCTACATCT GTATTAACGA   500
AGCGCTGGCA TTGACCCTGA GTGATTTTTC TCTGGTCCCG CCGCATCCAT   550
ACCGCCAGTT GTTTACCCTC ACAACGTTCC AGTAACCGGG CATGTTCATC   600
ATCAGTAACC CGTATCGTGA GCATCCTCTC TCGTTTCATC GGTATCATTA   650
CCCCCATGAA CAGAAATTCC CCCTTACACG GAGGCATCAA GTGACCAAAC   700
AGGAAAAAAC CGCCCTTAAC ATGGCCCGCT TTATCAGAAG CCAGACATTA   750
ACGCTTCTGG AGAAACTCAA CGAGCTGGAC GCGGATGAAC AGGCAGACAT   800
CTGTGAATCG CTTCACGACC ACGCTGATGA GCTTTACCGC AGCTGCCTCG   850
CGCGTTTCGG TGATGACGGT GAAAACCTCT GACACATGCA GCTCCCGGAG   900
ACGGTCACAG CTTGTCTGTA AGCGGATGCC GGGAGCAGAC AAGCCCGTCA   950
GGGCGCGTCA GCGGGTGTTG GCGGGTGTCG GGGCGCAGCC ATGACCCAGT  1000
CACGTAGCGA TAGCGGAGTG TATACTGGCT TAACTATGCG GCATCAGAGC  1050
AGATTGTACT GAGAGTGCAC CATATGCGGT GTGAAATACC GCACAGATGC  1100
GTAAGGAGAA AATACCGCAT CAGGCGCTCT TCCGCTTCCT CGCTCACTGA  1150
CTCGCTGCGC TCGGTCGTTC GGCTGCGGCG AGCGGTATCA GCTCACTCAA  1200
AGGCGGTAAT ACGGTTATCC ACAGAATCAG GGGATAACGC AGGAAAGAAC  1250
ATGTGAGCAA AAGGCCAGCA AAAGGCCAGG AACCGTAAAA AGGCCGCGTT  1300
GCTGGCGTTT TTCCATAGGC TCCGCCCCCC TGACGAGCAT CACAAAAATC  1350
GACGCTCAAG TCAGAGGTGG CGAAACCCGA CAGGACTATA AAGATACCAG  1400
GCGTTTCCCC CTGGAAGCTC CCTCGTGCGC TCTCCTGTTC CGACCCTGCC  1450
GCTTACCGGA TACCTGTCCG CCTTTCTCCC TTCGGGAAGC GTGGCGCTTT  1500
CTCATAGCTC ACGCTGTAGG TATCTCAGTT CGGTGTAGGT CGTTCGCTCC  1550
AAGCTGGGCT GTGTGCACGA ACCCCCCGTT CAGCCCGACC GCTGCGCCTT  1600
ATCCGGTAAC TATCGTCTTG AGTCCAACCC GGTAAGACAC GACTTATCGC  1650
CACTGGCAGC AGCCAGGCGC GCCTTGGCCT AAGAGGCCAC TGGTAACAGG  1700
ATTAGCAGAG CGAGGTATGT AGGCGGTGCT ACAGAGTTCT TGAAGTGGTG  1750
GCCTAACTAC GGCTACACTA GAAGGACAGT ATTTGGTATC TGCGCTCTGC  1800
TGAAGCCAGT TACCTTCGGA AAAAGAGTTG GTAGCTCTTG ATCCGGCAAA  1850
CAAACCACCG CTGGTAGCGG TGGTTTTTTT G1TTGCAAGC AGCAGATTAC  1900
GCGCAGAAAA AAAGGATCTC AAGAAGATCC TTTGATCTTT TCTACGGGGT  1950
CTGACGCTCA GTGGAACGAA AACTCACGTT AAGGGATTTT GGTCATGAGA  2000
TTATCAAAAA GGATCTTCAC CTAGATCCTT TTAAATTAAA AATGAAGTTT  2050
TAAATCAATC TAAAGTATAT ATGAGTAAAC TTGGTCTGAC AGTTACCAAT  2100
GCTTAATCAG TGAGGCACCT ATCTCAGCGA TCTGTCTATT TCGTTCATCC  2150
ATAGTTGCCT GACTCCCCGT CGTGTAGATA ACTACGATAC GGGAGGGCTT  2200
ACCATCTGGC CCCAGTGCTG CAATGATACC GCGAGACCCA CGCTCACCGG  2250
CTCCAGATTT ATCAGCAATA AACCAGCCAG CCGGAAGGGC CGAGCGCAGA  2300
AGTGGTCCTG CAACTTTATC CGCCTCCATC CAGTCTATTA ATTGTTGCCG  2350
GGAAGCTAGA GTAAGTAGTT CGCCAGTTAA TAGTTTGCGC AACGTTGTTG  2400
CCATTGCTGC AGGCATCGTG GTGTCACGCT CGTCGTTTGG TATGGCTTCA  2450
TTCAGCTCCG GTTCCCAACG ATCAAGGCGA GTTACATGAT CCCCCATGTT  2500
GTGCAAAAAA GCGGTTAGCT CCTTCGGTCC TCCGATCGTT GTCAGAAGTA  2550
AGTTGGCCGC AGTGTTATCA CTCATGGTTA TGGCAGCACT GCATAATTCT  2600
CTTACTGTCA TGCCATCCGT AAGATGCTTT TCTGTGACTG GTGAGTACTC  2650
AACCAAGTCA TTCTGAGAAT AGTGTATGCG GCGACCGAGT TGCTCTTGCC  2700
CGGCGTCAAC ACGGGATAAT ACCGCGCCAC ATAGCAGAAC TTTAAAAGTG  2750
CTCATCATTG GAAAACGTTC TTCGGGGCGA AAACTCTCAA GGATCTTACC  2800
GCTGTTGAGA TCCAGTTCGA TGTAACCCAC TCGTGCACCC AACTGATCTT  2850
CAGCATCTTT TACTTTCACC AGCGTTTCTG GGTGAGCAAA AACAGGAAGG  2900
CAAAATGCCG CAAAAAAGGG AATAAGGGCG ACACGGAAAT GTTGAATACT  2950
CATACTCTTC CTTTTTCAAT ATTATTGAAG CATTTATCAG GGTTATTGTC  3000
TCATGAGCGG ATACATATTT GAATGTATTT AGAAAAATAA ACAAATAGGG  3050
GTTCCGCGCA CATTTCCCCG AAAAGTGCCA CCTGACGTCT AAGAAACCAT  3100
```

APPENDIX-continued

SEQUENCE LISTING

| | |
|---|---|
| TATTATCATG ACATTAACCT ATAAAAATAG GCGTATCACG AGGCCCTTTC | 3150 |
| GTCTTCAAG | 3159 | pCK7-96 (SEQ ID NO: 39)

TCTTCCGCTTCCTCGCTCACTGACTCGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTGAGCAAAAGGCCAGCAAAAGGCCAGGA
ACCGTAAAAAGGCCGCGTTGCTGGCGTTTTTCCATAGGCTCCGCCCCCCTGACGAGCATCACAAAAATCGACGCTCA
AGTCAGAGGTGGCGAAACCCGACAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCACGAACCCCCCGTTCAGCCCGAC
CGCTGCGCCTTATCCGGTAACTATCGTCTTGAGTCCAACCCGGTAAGACACGACTTATCGCCACTGGCAGCAGCCAC
TGGTAACAGGATTAGCAGAGCGAGGTATGTAGGCGGTGCTACAGAGTTCTTGAAGTGGTGGCCTAACTACGGCTACA
CTAGAAGGACAGTATTTGGTATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACGCGCAGAAAAAAAGGATCTCA
AGAAGATCCTTTGATCTTTTCTACGGGGTCTGACGCTCAGTGGAACGAAAACTCACGTTAAGGGATTTTGGTCATGA
GATTATCAAAAAGGATCTTCACCTAGATCCTTTTAAATTAAAAATGAAGTTTTAAATCAATCTAAAGTATATATGAG
TAAACTTGGTCTGACAGTTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCCCAGTGCTGCAATGATAC
CGCGAGACCCACGCTCACCGGCTCCAGATTTATCAGCAATAAACCAGCCAGCCGGAAGGGCCGAGCCGCAGAAGTGGT
CCTGCAACTTTATCCGCCTCCATCCAGTCTATTAATTGTTGCCGGGAAGCTAGAGTAAGTAGTTCGCCAGTTAATAC
TTTGCGCAACGTTGTTGCCATTGCTACAGGCATCGTGGTGTCACGCTCGTCGTTTGGTATGGCTTCATTCAGCTCCG
GTTCCCAACGATCAAGGCGAGTTACATGATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGCACTGCATAATTCTCTTACTGTCATGCC
ATCCGTAAGATGCTTTTCTGTGACTGGTGAGTACTCAACCAAGTCATTCTGAGAATAGTGTATGCGGCGACCGAGTT
GCTCTTGCCCGGCGTCAATACGGGATAATACCGCGCCACATAGCAGAACTTTAAAAGTGCTCATCATTGGAAAACGT
TCTTCGGGGCGAAAACTCTCAAGGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGGCAAAATGCCGCAAAAAAGGGAA
TAAGGGCGACACGGAAATGTTGAATACTCATACTCTTCCTTTTTCAATATTATTGAAGCATTTATCAGGGTTATTGT
CTCATGAGCGGATACATATTTGAATGTATTTAGAAAAATAAACAAATAGGGGTTCCGCGCACATTTCCCCGAAAAGT
GCCACCTGACGTCTAAGAAACCATTATTATCATGACATTAACCTATAAAAATAGGCGTATCACGAGGCCCTTTCGTC
TCGCGCGTTTCGGTGATGACGGTGAAAACCTCTGACACATGCAGCTCCCGGAGACGGTCACAGCTTGTCTGTAAGCG
GATGCCGGGAGCAGACAAGCCCGTCAGGGCGCGTCAGCGGGTGTTGGCGGGTGTCGGGGCTGGCTTAACTATGCGGC
ATCAGAGCAGATTGTACTGAGAGTGCACCATATGCGGTGTGAAATACCGCACAGATGCGTAAGGAGAAAATACCGCA
TCAGGCGCCATTCGCCATTCAGGCTGCGCAACTGTTGGGAAGGGCGATCGGTGCGGGCCTCTTCGCTATTACGCCAG
CTGGCGAAAGGGGGATGTGCTGCAAGGCGATTAAGTTGGGTAACGCCAGGGTTTTCCCAGTCACGACGTTGTAAAAC
GACGGCCAGTGCCAAGCTAGCGGCCGCGGTCCAACCACCAATCTCAAAGCTTGGTACCCGGGAGCCTGTTATCCCAG
CACAGTCCTGGAAGAGGCACAGGGGAAATAAAAGCGGACGGAGGCTTTCCTTGACTCAGCCGCTGCCTGGTCTTCTT
CAGACCTGTTCTGAATTCTAAACTCTGAGGGGGTCGGATGACGTGGCCATTCTTTGCCTAAAGCATTGAGTTTACTG
CAAGGTCAGAAAAGCATGCAAAGCCCTCAGAATGGCTGCAAAGAGCTCAACAAAACAATTTAGAACTTTATTAAGG
AATAGGGGGAAGCTAGGAAGAAACTCAAAACATCAAGATTTTAAATACGCTTCTTGGTCTCCTTGCTATAATTATCT
GGGATAAGCATGCTGTTTTCTGTCTGTCCCTAACATGCCCTGTGATTATCCGCAAACAACACACCCAAGGGCAGAAC
TTTGTTACTTAAACACCATCCTGTTTGCTTCTTTCCTCAGGAACTGTGGCTGCACCATCTGTOTTCATCTTCCCGCC
ATCTGATGAGCAGTTGAAATCTGGAACTGCCTCTGTTGTGTGCCTGCTGAATAACTTCTATCCCAGAGAGGCCAAAG
TACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGTGTTAGAGGGAGAAGTGCCCCCACCTGC
TCCTCAGTTCCAGCCTGACCCCCTCCCATCCTTTGGCCTCTGACCCCTTTTCCACAGGGGACCTACCCCTATTGCGG
TCCTCCAGCTCATCTTTCACCTCACCCCCCTCCTCCTCCTTGGCTTTAATTATGCTAATGTTGGAGGAGAATGAATA
AATAAAGTGAATCTTTGCACCTGTGGTTTCTCTCTTTCCTCAATTTAATAATTATTATCTGTTGTTTACCAACTACT
CAATTTCTCTTATAAGGGACTAAATATGTAGTCATCCTAAGGCGCATAACCATTTATAAAAATCATCCTTCATTCTA
TTTTACCCTATCATCCTCTGCAAGACAGTCCTCCCTCAAACCCACAAGCCTTCTGTCCTCACAGTCCCCTGGGCCAT
GGATCCTCACATCCCAATCCGCGGCCGCAATTCGTAATCATGGTCATAGCTGTTTCCTGTGTGAAATTGTTATCCGC
TCACAATTCCACACAACATACGAGCCGGAAGCATAAAGTGTAAAGCCTGGGGTGCCTAATGAGTGAGCTAACTCACA
TTAATTGCGTTGCGCTCACTGCCCGCTTTCCAGTCGGGAAACCTGTCGTGCCAGCTGCATTAATGAATCGGCCAACG
CGCGGGGAGAGGCGGTTTGCGTATTGGGCGC pCG7-96 (SEQ ID NO: 40)

GAACTCGAGCAGCTGAAGCTTTCTGGGGCAGGCCAGGCCTGACCTTGGCTTTGGGGCAGGGAGGGGGCTAAGGTGAG
GCAGGTGGCGCCAGCCAGGTGCACACCCAATGCCCATGAGCCCAGACACTGGACGCTGAACCTCGCCGACAGTTAAG
AACCCAGGGGCCTCTGCGCCCTGGGCCCAGCTCTGTCCCACACCGCGGTCACATGGCACCACCTCTCTTGCAGCCTC
CACCAAGGGCCCATCGGTCTTCCCCCTGGCACCCTCCTCCAAGAGCACCTCTGGGGGCACAGCGGCCCTGGGCTGCC
TGGTCAAGGACTACTTCCCCGAACCGGTGACGGTGTCGTGGAACTCAGGCGCCCTGACCAGCGGCGTGCACACCTTC
CCGGCTGTCCTACAGTCCTCAGGACTCTACTCCCTCAGCAGCGTGGTGACCGTGCCCTCCAGCAGCTTGGGCACCCA
GACCTACATCTGCAACGTGAATCACAAGCCCAGCAACACCAAGGTGGACAAGAAAGTTGGTGAGAGGCCAGCACAGG
GAGGGAGGGTGTCTGCTGGAAGCCAGGCTCAGCGCTCCTGCCTGGACGCATCCCGGCTATGCAGCCCCAGTCCAGGG
CAGCAAGGCAGGCCCCGTCTGCCTCTTCACCCGGAGGCCTCTGCCCGCCCCACTCATGCTCAGGGAGAGGGTCTTCT
GGCTTTTTCCCCAGGCTCTGGGCAGGCACAGGCTAGGTGCCCCTAACCCAGGCCCTGCACACAAAGGGGCAGGTGCT
GGGCTCAGACCTGCCAAGAGCCATATCCGGGAGGACCCTGCCCCTGACCTAAGCCCACCCCAAAGGCCAAACTCTCC
ACTCCCTCAGCTCGGACACCTTCTCTCCTCCCAGATTCCAGTAACTCCCAATCTTCTCTCTGCAGAGCCCAAATCTT
GTGACAAAACTCACACATGCCCACCGTGCCCAGGTAAGCCAGCCCAGGCCTCGCCCTCCAGCTCAAGGCGGGACAGG
TGCCCTAGAGTAGCCTGCATCCAGGGACAGGCCCCAGCCGGGTGCTGACACGTCCACCTCCATCTCTTCCTCAGCAC
CTGAACTCCTGGGGGGACCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTACCGTGTGGTCAGCGTCCTCACCGTCC
TGCACCAGGACTGGCTGAATGGCAAGGAGTACAAGTGCAAGGTCTCCAACAAAGCCCTCCCAGCCCCCATCGAGAAA
ACCATCTCCAAAGCCAAAGGTGGGACCCGTGGGGTGCGAGGGCCACATGGACAGAGGCCGGCTCGGCCCACCCTCTG

APPENDIX-continued

SEQUENCE LISTING

```
CCCTGAGAGTGACCGCTGTACCAACCTCTGTCCCTACAGGGCAGCCCCGAGAACCACAGGTGTACACCCTGCCCCCA
TCCCGGGATGAGCTGACCAAGAACCAGGTCAGCCTGACCTGCCTGGTCAAAGGCTTCTATCCCAGCGACATCGCCGT
CGAGTGGGAGAGCAATGGGCAGCCGGAGAACAACTACAAGACCACGCCTCCCGTGCTGGACTCCGACGGCTCCTTCT
TCCTCTACAGCAAGCTCACCGTGGACAAGAGCAGGTGGCAGCAGGGGAACGTCTTCTCATGCTCCGTGATGCATGAG
GCTCTGCACAACCACTACACGCAGAAGAGCCTCTCCCTGTCTCCGGGTAAATGAGTGCGACGGCCGGCAAGCCCCCG
CTCCCCGGGCTCTCGCGGTCGCACGAGGATGCTTGGCACGTACCCCCTGTACATACTTCCCGGGCGCCCAGCATGGA
AATAAAGCACCCAGCGCTGCCCTGGGCCCCTGCGAGACTGTGATGGTTCTTTCCACGGGTCAGGCCGAGTCTGAGGC
CTGAGTGGCATGAGGGAGGCAGAGCGGGTCCCACTGTCCCCACACTGGCCCAGGCTGTGCAGGTGTGCCTGGGCCCC
CTAGGGTGGGGCTCAGCCAGGGGCTGCCCTCGGCAGGGTGGGGGATTTGCCAGCGTGGCCCTCCCTCCAGCAGCACC
TGCCCTCGGCTGGGCCACGGGAAGCCCTAGGAGCCCCTGGGGACAGACACACAGCCCCTGCCTCTGTAGGAGACTGT
CCTGTTCTGTGAGCGCCCCTGTCCTCCCGACCTCCATGCCCACTCGGGGGCATGCCTGCAGGTCGACTCTAGAGGAT
CCCCGGGTACCGAGCTCGAATTCATCGATGATATCAGATCTGCCGGTCTCCCTATAGTGAGTCGTATTAATTTCGAT
AAGCCAGGTTAACCTGGATTAATGAATCGGCCAACGCGCGGGGAGAGGCGGTTTGCGTATTGGGCGCTCTTCCGCTT
CCTCGCTCACTGACTCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCCAGGAACCGTAAAAA
GGCCGCGTTGCTGGCGTTTTTCCATAGGCTCCGCCGCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTCAATGCTCACGCTGTAGGTA
TCTCAGTTCGGTGTAGGTCGTTCGCTCCAACCTGGGCTGTGTGCACGAACCCCCCGTTCAGCCCGACCGCTGCGCCT
TATCCGGTAACTATCGTCTTGAGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAACTACGGCTAGACTAGAAGGAC
AGTATTTGGTATCTGCGCTCTGCTGAAGCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGCAGAAAAAAAGGATCTCAAGAAGATCCT
TTGATCTTTTCTACGGGGTCTGACGCTCAGTGGAACGAAAACTCACGTTAAGGGATTTTGGTCATGAGATTATCAAA
AAGGATCTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTTGCCTGA
CTCCCCGTCGTGTAGATAACTACGATACGGGAGGGCTTACCATCTGGCCCCAGTGCTGCAATGATACCGCGAGACCC
ACGCTCACCGGCTCCAGATTTATCAGCAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTAGTTCGCCAGTTAATAGTTTGCGCAAC
GTTGTTGCCATTGCTACAGGCATCGTGGTGTCACGCTCGTCGTTTGGTATGGCTTCATTCAGCTCCGGTTCCCAACG
ATCAAGGCGAGTTACATGATCCCCCATGTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCATTGGAAAACGTTCTTCGGGGC
GAAAACTCTCAAGGATCTTACCGCTGTTGAGATCCAGTTCGATGTAACCCACTCGTGCACCCAACTGATCTTCAGCA
TCTTTTACTTTCACCAGCGTTTCTGGGTGAGCAAAAACAGGAAGGCAAAATGCCGCAAAAAAGGGAATAAGGGCGAC
ACGGAAATGTTGAATACTCATACTCTTCCTTTTTCAATATTATTGAAGCATTTATCAGGGTTATTGTCTCATGAGCG
GATACATATTTGAATGTATTTAGAAAAATAAACAAATAGGGGTTCCGCGCACATTTCCCCGAAAAGTGCCACCTGAC
GTCTAAGAAACCATTATTATCATGACATTAACCTATAAAAATAGGCGTATCACGAGGCCCTTTCGTCTCGCGCGTTT
CGGTGATGACGGTGAAAACCTCTGACACATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGGCTGGCTTAACTATGCGGCATCAGAGCAG
ATTGTACTGAGAGTGCACCATATGGACATATTGTCGTTAGAACGCGGCTACAATTAATACATAACCTTATGTATCAT
ACACATACGATTTAGGTGACACTATA
``` pG4HE (SEQ ID NO: 41)

```
GAACTCGAGCAGCTGAAGCTTTCTGGGGCAGGCCGGGCCTGACTTTGGCTGGGGGCAGGGAGGGGGCTAAGGTGACG
CAGGTGGCGCCAGCCAGGTGCACACCCAATGCCCATGAGCCCAGACACTGGACCTGCATGGACCATCGCGGATAGA
CAAGAACCGAGGGGCCTCTGCGCCCTGGGCCCAGCTCTGTCCCACACCGCGGTCACATGGCACCACCTCTCTTGCAG
CTTCCACCAAGGGCCCATCCGTCTTCCCCCTGGCGCCCTGCTCCAGGAGCACCTCCGAGAGCACAGCCGCCCTGGGC
TGCCTGGTCAAGGACTACTTCCCCGAACCCGTGACCGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCCAGCAGCTTGGGCA
CGAAGACCTACACCTGCAACGTAGATCACAAGCCCAGCAACACCAAGGTGGACAAGAGAGTTGGTGAGAGGCCAGCA
CAGGGAGGGAGGGTGTCTGCTGGAAGCCAGGCTCAGCCCTCCTGCCTGGACGCACCCCGGCTGTGCAGCCCCAGCCC
AGGGCAGCAAGGCATGCCCCATCTGTCTCCTCACCCGGAGGCCTCTGACCACCCCACTCATGCTCAGGGAGAGGGTC
TTCTGGATTTTTTCCACCAGGCTCCGGGCAGCCACAGGCTGGATGCCCCTACCCCAGGCCCTGCGCATACAGGGGCAG
GTGCTGCGCTCAGACCTCCCAAGAGCCATATCCGGGAGGACCCTGCCCCTGACCTAAGCCCACCCCAAAGGCCAAAC
TCTCCACTCCCTCAGCTCAGACACCTTCTCTCCTCCCAGATCTGAGTAACTCCCAATCTTCTCTCTGCAGAGTCCAA
ATATGGTCCCCCATGCCCATCATGCCCAGGTAAGCCAACCCAGCCCTCGCCCTCCAGCTCAAGGCGGGACAGGTGCC
CTAGAGTAGCCTGCATCCAGGGACAGGCCCCAGCCGGGTGCTGACGCATCCACCTCCATCTCTTCCTCAGCACCTGA
GTTCCTGGGGGACCATCAGTCTTCCTGTTCCCCCCAAAACCCAAGGACACTCTCATGATCTCCCGGACCCCTGAGG
TCACGTGCGTGGTGGTGGACGTGAGCCAGGAAGACCCCGAGGTCCAGTTCAACTGGTACGTGGATGGCGTGGAGGTG
CATAATGCCAAGACAAAGCCGCGGGAGGAGCAGTTCAACAGCACGTACCGTCTGGTCAGCGTCCTCACCGTCCTGCA
CCAGGACTGGCTGAACGGCAAGGAGTACAAGTGCAAGGTCTCCAACAAAGGCCTCCCGTCCTCCATCGAGAAACCA
TCTCCAAAGCCAAAGGTGGGACCCACGGGGTGCGAGGGCCACATGGACAGAGGCCAGCTCGGCCCACCCTCTGCCCT
GGGAGTGACCGCTGTGCCAACCTCTGTCCCTACAGGGCAGCCCCGAGAGCCACAGGTGTACACCCTGCCCCCATCCC
AGGAGGAGATGACCAAGAACCAGGTCAGCCTGACCTGCCTGGTCAAAGGCTTCTACCCCAGCGACATCGCCGTGGAG
TGGGAGAGCAATGGGCAGCCGGAGAACAACTACAAGACCACGCCTCCCGTGCTGGACTCCGACGGCTCCTTCTTCCT
CTACAGCAGGCTAACCGTGGACAAGAGCAGGTGGCAGGAGGGGAATGTCTTCTCATGCTCCGTGATGCATGAGGGTC
TGCACAACCACTACACACAGAAGAGCCTCTCCCTGTCTCTGGGTAAATGAGTGCCAGGGCCGGCAAGCCCCCGCTCC
CCGGGCTCTCGGGTCGCGCGAGGATGCTTGGCACGTACCCCGTCTACATACTTCCCAGGCACCCAGCATGGAAATA
AAGCACCCACCACTGCCCTGGGCCCCTGTGAGACTGTGATGGTTCTTTCCACGGGTCAGGCCGAGTCTGAGGCCTGA
GTGACATGAGGGAGGCAGAGCGGGTCCCACTGTCCCCACACTGGCCCAGGCTGTGCAGGTGTGCCTGCGCCACCTAG
GGTGGGGCTCAGCCAGGGGCTGCCCTCGGCAGGGTGGGGGATTTGCCAGCGTGGCCCTCCCTCCAGCAGCAGCTGCC
CTGGGCTGGGCCACGGGAAGCCCTAGGAGCCCCTGGGGACAGACACACAGCCCCTGCCTCTGTAGGAGACTGTCCTG
TCCTGTGAGCGCCCTGTCCTCCGACCCCCCATGCCCACTCGGGGGATCCCCGGGTACCGAGCTCGAATTCATCGAT
GATATCAGATCTGCCGGTCTCCCTATACTGACTCGTATTAATTTCGATAAGCCAGGTTAACCTGCATTAATGAATCG
GCCAACGCGCGGGGAGAGGCGGTTTGCGTATTGGGCGCTCTTCCGCTTCCTCGCTCACTGACTCGCTGCGCTCGGTC
```

APPENDIX-continued

SEQUENCE LISTING

```
GTTCGGCTGCGGCGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGTTTTTCCATAGGC
TCCGCCCCCTGACGAGCATCACAAAAATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCTGCCGCTTACCGGATACCTGTCCGCCTT
TCTCCCTTCGGGAAGCGTGGCGCTTTCTCAATGCTCACGCTGTAGGTATCTCAGTTCGGTGTAGGTCGTTCGCTCCA
AGCTGGGCTGTGTGCACGAACCCCCCGTTCAGCCCGACCGCTGCGCCTTATCCGGTAACTATCGTCTTGAGTCCAAC
CCGGTAAGACACGACTTATCGCCACTGGCAGCAGCCACTGGTAACAGGATTAGCAGAGCGAGGTATGTAGGCGGTGC
TACAGAGTTCTTGAAGTGGTGCCTAACTACGGCTACACTAGAAGGACAGTATTTGGTATCTGCGCTCTGCTGAAGC
CAGTTACCTTCGGAAAAAGAGTTGGTAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTTCACCTAGATCCTTTTAAATT
AAAAATGAAGTTTTAAATCAATCTAAACTATATATGAGTAAACTTGGTCTGACAGTTACCAATGCTTAATCAGTGAG
GCACCTATCTCAGCGATCTGTCTATTTCGTTCATCCATAGTTGCCTGACTCCCCGTCGTGTAGATAACTACGATACG
GGAGGGCTTACCATCTGGCCCCAGTGCTGCAATGATACCGCCACACCCACGCTCACCCGCTCCACATTTATCACCAA
TAAACCAGCCAGCCGGAAGGGCCGAGCGCAGAAGTGGTCCTGCAACTTTATCCCCGTCCATCCAGTCTATTAATTGT
TGCCGGGAAGCTAGAGTAAGTAGTTCGCCACTTAATAGTTTGCGCAACGTTGTTGCCATTGCTACAGGCATCGTGGT
GTCACGCTCGTCCTTTGGTATCGCTTCATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGTAAGTTGGCCGCAGTGTTATCACTCATG
GTTATGCAGCACTGCATAATTCTCTTACTGTCATCCCATCCGTAAGATGCTTTTCTGTGACTGGTGAGTACTCAAC
CAAGTCATTCTGAGAATAGTGTATGCGGCGACCGAGTTCCTCTTGCCCGGCGTCAATACGGGATAATACCCCGCCAC
ATAGCAGAACTTTAAAAGTGCTCATCATTGGAAAACGTTCTTCGGGGCGAAAACTCTCAAGGATCTTACCGCTGTTG
AGATCCAGTTCGATGTAACCCACTCGTGCACCCAACTGATCTTCAGCATCTTTTACTTTCACCAGCGTTTCTGGGTG
AGCAAAAACAGGAAGGCAAAATGCCGCAAAAAACCGAATAAGGGCGACACGGAAATGTTGAATACTCATACTCTTCC
TTTTTCAATATTATTGAAGCATTTATCAGGGTTATTGTCTCATCACCGGATACATATTTGAATCTATTTAGAAAAAT
AAACAAATACCGCTTCCGCCCACATTTCCCCGAAAAGTGCCACCTGACGTCTAAGAAACCATTATTATCATGACATT
AACCTATAAAAATAGGCGTATCACGAGGCCCTTTCGTCTCGCGCGTTTCCGTCATGACGGTGAAAACCTCTGACACA
TGCAGCTCCCGGAGACGGTCACAGCTTGTCTGTAAGCGGATCCCCGGAGCAGACAAGCCCCTCACCGCCCGTCACCG
GCTGTTGGCGGCTGTCCCGGCTCCCTTAACTATGCGGCATCAGACCAGATTGTACTGAGAGTGCACCATATGGACAT
ATTGTCGTTAGAACGCGGCTACAATTAATACATAACCTTATGTATCATACACATACGATTTAGGTGACACTATA
```

10D1 VH (SEQ ID NO: 16)

```
CAGGTGCAGC TGGTGGAGTC TGGGGGAGGC GTGGTCCAGC CTGGGAGGTC   50
CCTGAGACTC TCCTGTGCAG CCTCTGCATT CACCTTCAGT AGCTATACTA  100
TGCACTGGGT CCGCCAGGCT CCAGGCAAGG GGCTGGAGTG GGTGACATTT  150
ATATCATATG ATGGAAACAA TAAATACTAC GCAGACTCCG TGAAGGGCCG  200
ATTCACCATC TCCAGAGACA ATTCCAAGAA CACGCTGTAT CTGCAAATGA  250
ACAGCCTGAG AGCTGAGGAC ACGGCTATAT ATTACTGTGC GAGGACCGGC  300
TGGCTGGGGC CCTTTGACTA CTGGGGCCAG GGAACCCTGG TCACCGTCTC  350
CTCAG
```

10D1 VK (SEQ ID NO: 6)

```
GAAATTGTGT TGACGCAGTC TCCAGGCACC CTGTCTTTGT CTCCAGGGGA   50
AAGAGCCACC CTCCTCTGCA GGGCCAGTCA GAGTGTTGGC AGCAGCTACT  100
TAGCCTGGTA CCAGCAGAAA CCTGGCCAGG CTCCCAGGCT CCTCATCTAT  150
GGTGCATTCA GCAGGGCCAC TGGCATCCCA GACAGGTTCA GTGGCAGTGG  200
GTCTGGGACA GACTTCACTC TCACCATCAG CAGACTGGAG CCTGAAGATT  250
TTGCAGTGTA TTACTGTCAG CAGTATGGTA GCTCACCGTG GACGTTCGGC  300
CAAGGGACCA AGGTGGAAAT CAAAC                             325
```

4B6 VH (SEQ ID NO: 18)

```
CAGGTGCAGC TGGTGGAGTC TGGGGGAGGC GTGGTCCAGC CTGGGAGGTC   50
CCTGAGACTC TCCTGTGCAG CCTCTGGATT CACCTTCAGT AGCTATACTA  100
TGCACTGGGT CCGCCAGGCT CCAGGCAAGG GGCTGGAGTG GGTGACATTT  150
ATATCATATG ATGGAAGCAA TAAACACTAC GCAGACTCCG TCAACCGCCG  200
ATTCACCGTC TCCAGAGACA ATTCCAAGAA CACGCTGTAT CTGCAAATGA  250
ACAGCCTGAG AGCTGAGGAC ACGGCTATAT ATTACTGTGC GAGGACCGGC  300
TGGCTGGGGC CCTTTGACTA CTGGGGCCAG GGAACCCTGG TCACCGTCTC  350
CTCAG
```

4B6 VK (SEQ ID NO: 8)

```
GAAATTGTGT TGACGCAGTC TCCAGGCACC CTGTCTTTGT CTCCAGGGGA   50
AAGAGCCACC CTCCTCTGCA GGGCCAGTCA GAGTGTTAGC AGCAGCTTCT  100
TAGCCTGGTA CCAGCAGAAA CCTGGCCAGG CTCCCAGGCT CCTCATCTAT  150
GGTGCATCCA GCAGGGCCAC TGGCATCCCA GACAGGTTCA GTGGCAGTGG  200
GTCTGGGACA GACTTCACTC TCACCATCAG CAGACTGGAG CCTGAAGATT  250
TTGCAGTGTA TTACTGTCAG CAGTATGGTA GCTCACCGTG GACGTTCGGC  300
CAAGGGACCA AGGTGGAAAT CAAAC                             325
```

1E2 VH (SEQ ID NO: 22)

```
CAGGTGCAGC TGGTGGAGTC TGGGGGAGGC GTGGTCCAGC CTGGGAGGTC   50
CCTGAGACTC TCCTGTGCAG CGTCTGGATT CACCTTCAGT AGCTATGCA   100
TGCACTGGGT CCGCCAGGCT CCTGGCCAGG GGCTGGAGTG GGTGGCAGTT  150
ATATGGTATG ATGGAAGTAA TAAATACTAT GCAGACTCCG TGAAGGGCCG  200
```

APPENDIX-continued

SEQUENCE LISTING

```
ATTCACCATC TCCAGAGACA ATTCCAAGAA CACGCTGTAT CTGCAAATGA    250
ACAGCCTGAG AGCCGAGGAC ACGGCTGTGT TTTACTGTGC GAGAGCTCCC    300
AATTATATTG GTGCTTTTGA TGTCTGGGGC CAAGGGACAA TGGTCACCGT    350
CTCTTCAG
```

1E2 VK (SEQ ID NO: 12)

```
GACATCCAGA TGACCCAGTC TCCATCCTCA CTGTCTGCAT CTGTAGGAGA     50
CAGAGTCACC ATCACTTGTC GGGCGAGTCA GGGTATTAGC AGCTGGTTAG    100
CCTGGTATCA GCAGAAACCA GAGAAAGCCC CTAAGTCCCT GATCTATGCT    150
GCATCCAGTT TGCAAAGTGG GGTCCCATCA AGGTTCAGCG GCAGTGGATC    200
TGGGACAGAT TTCACTCTCA CCATCAGCAG CCTGCAGCCT GAAGATTTTG    250
CAACTTATTA CTGCCAACAG TATAATAGTT ACCCTCCGAC GTTCGGCCAA    300
GGGACCAAGG TGGAAATCAA AC                                  322
```

What is claimed is:

1. A method for increasing an immune response to an antigen in a subject, the method comprising administering to the subject an anti-CTLA-4 antibody or antigen-binding portion thereof, wherein the antibody or antigen-binding portion thereof comprises a heavy chain variable region that comprises CDR1, CDR2, and CDR3 domains; and a light chain variable region that comprises CDR1, CDR2, and CDR3 domains, wherein the heavy chain variable region and light chain variable region CDR3 domains are selected from the group consisting of:

(a) a heavy chain variable region CDR3 comprising amino acids having the sequence set forth in SEQ ID NO:37; and a light chain variable region CDR3 comprising amino acids having the sequence set forth in SEQ ID NO:35; and (b) a heavy chain variable region CDR3 comprising amino acids having the sequence set forth in SEQ ID NO:38; and a light chain variable region CDR3 comprising amino acids having the sequence set forth in SEQ ID NO:36; and binds to human CTLA-4 with a binding affinity of about $10^8$ $M^{-1}$ or greater.

2. The method of claim 1, wherein the antibody or antigen-binding portion thereof comprises:

(a) a heavy chain variable region comprising CDR3 and CDR2 sequences set forth in SEQ ID NOs:37 and 32, respectively; and a light chain variable region comprising CDR3 and CDR2 sequences set forth in SEQ ID NOs:35 and 29, respectively;

(b) a heavy chain variable region comprising CDR3 and CDR2 sequences set forth in SEQ ID NOs: 37 and 33, respectively; and a light chain variable region comprising CDR3 and CDR2 sequences set forth in SEQ ID NOs: 35 and 30, respectively; or
(c) a heavy chain variable region comprising CDR3 and CDR2 sequences set forth in SEQ ID NOs:38 and 34, respectively; and a light chain variable region comprising CDR3 and CDR2 sequences set forth in SEQ ID NOs:36 and 31, respectively.

3. The method of claim 2, wherein the antibody or antigen-binding portion thereof comprises:
(a) a heavy chain variable region comprising CDR3, CDR2 and CDR1 sequences set forth in SEQ ID NOs:37, 32 and 27, respectively; and a light chain variable region comprising CDR3, CDR2 and CDR1 sequences set forth in SEQ ID NOs:35, 29 and 24, respectively;
(b) a heavy chain variable region comprising CDR3, CDR2 and CDR1 sequences set forth in SEQ ID NOs:37, 33 and 27, respectively; and a light chain variable region comprising CDR3, CDR2 and CDR1 sequences set forth in SEQ ID NOs:35, 30 and 25, respectively; or
(c) a heavy chain variable region comprising CDR3, CDR2 and CDR1 comprising sequences set forth in SEQ ID NOs:38, 34 and 28, respectively; and a light chain variable region comprising CDR3, CDR2 and CDR1 sequences set forth in SEQ ID NOs:36, 31 and 26, respectively.

4. The method of claim 1, wherein the antibody or antigen-binding portion thereof comprises: (a) a heavy chain variable region derived from a human $V_H$ 3-30.3 gene; and (b) a light chain variable region derived from a human $V_K$ A-27 gene.

5. The method of claim 1, wherein the antibody or antigen-binding portion thereof comprises: (a) a heavy chain variable region derived from a human $V_H$ 3-33 gene; and (b) a light chain variable region derived from a human $V_K$ L-15 gene.

6. The method of claim 4, wherein the antibody or antigen-binding portion thereof comprises a heavy chain variable region CDR3 sequence set forth in SEQ ID NO: 37, and a light chain variable region CDR3 sequence set forth in SEQ ID NO: 35.

7. The method of claim 5, wherein the antibody or antigen-binding portion thereof comprises a heavy chain variable region CDR3 sequence set forth in SEQ ID NO: 38, and a light chain variable region CDR3 sequence set forth in SEQ ID NO: 36.

8. The method of claim 1, wherein the antibody or antigen-binding portion thereof comprises at least one heavy chain variable region comprising an amino acid sequence selected from the group consisting of SEQ ID NOS: 17, 19 and 23.

9. The method of claim 1, wherein the antibody or antigen-binding portion thereof comprises at least one light chain variable region comprising an amino acid sequence selected from the group consisting of SEQ ID NOS: 7, 9 and 13.

10. The method of claim 1, wherein the antibody or antigen-binding portion thereof comprises a heavy chain variable region comprising the amino acid sequence set forth in SEQ ID NO: 17 and a light chain variable region comprising the amino acid sequence set forth in SEQ ID NO: 7.

11. The method of claim 1, wherein the antibody or antigen-binding portion thereof comprises a heavy chain variable region comprising the amino acid sequence set forth in SEQ ID NO: 19 and a light chain variable region comprising the amino acid sequence set forth in SEQ ID NO: 9.

12. The method of claim 1, wherein the antibody or antigen-binding portion thereof comprises a heavy chain variable region comprising the amino acid sequence set forth in SEQ ID NO: 23 and a light chain variable region comprising the amino acid sequence set forth in SEQ ID NO: 13.

13. The method of claim 1, wherein the antibody or antigen-binding portion thereof comprises: (a) a heavy chain variable region comprising CDR1, CDR2, and CDR3 sequences set forth in SEQ ID NOS: 27, 32 and 37, respectively; and (b) a light chain variable region comprising CDR1, CDR2, and CDR3 sequences set forth in SEQ ID NOS: 24, 29 and 35, respectively.

14. The method of claim 1, wherein the antibody or antigen-binding portion thereof comprises: (a) a heavy chain variable region comprising CDR1, CDR2, and CDR3 sequences set forth in SEQ ID NOS: 27, 33 and 37, respectively; and (b) a light chain variable region comprising CDR1, CDR2, and CDR3 sequences set forth in SEQ ID NOS: 25, 30 and 35, respectively.

15. The method of claim 1, wherein the antibody or antigen-binding portion thereof comprises: (a) a heavy chain variable region comprising CDR1, CDR2, and CDR3 sequences set forth in SEQ ID NOS: 28, 34 and 38, respectively; and (b) a light chain variable region comprising CDR1, CDR2, and CDR3 sequences set forth in SEQ ID NOS: 26, 31 and 36, respectively.

16. A method for increasing an immune response to an antigen in a subject, the method comprising administering to the subject an antibody or antigen-binding portion thereof, wherein the antibody or antigen-binding portion thereof competes for binding to a human CTLA-4 polypeptide with a reference antibody comprising the amino acid sequence set forth in SEQ ID NO: 17, and the amino acid sequence set forth in SEQ ID NO: 7; and has a binding affinity of about $10^8 M^{-1}$ or greater.

17. A method for increasing an immune response to an antigen in a subject, the method comprising administering to the subject an anti-CTLA-4 antibody or antigen-binding portion thereof, comprising: (a) a heavy chain variable region comprising CDR1, CDR2, and CDR3 sequences set forth in SEQ ID NOS: 27, 32 and 37, respectively; and (b) a light chain variable region comprising CDR1, CDR2, and CDR3 sequences set forth in SEQ ID NOS: 24, 29 and 35, respectively.

18. A method for increasing an immune response to an antigen in a subject, the method comprising administering to the subject an anti-CTLA-4 antibody or antigen-binding portion thereof, comprising: (a) a heavy chain variable region comprising CDR1, CDR2, and CDR3 sequences set forth in SEQ ID NOS: 27, 33 and 37, respectively; and (b) a light chain variable region comprising CDR1, CDR2, and CDR3 sequences set forth in SEQ ID NOS: 25, 30 and 35, respectively.

19. A method for increasing an immune response to an antigen in a subject, the method comprising administering to the subject an anti-CTLA-4 antibody or antigen-binding portion thereof, comprising: (a) a heavy chain variable region comprising CDR1, CDR2, and CDR3 sequences set forth in SEQ ID NOS: 28, 34 and 38, respectively; and (b) a light chain variable region comprising CDR1, CDR2, and CDR3 sequences set forth in SEQ ID NOS: 26, 31 and 36, respectively.

20. A method for increasing an immune response to an antigen in a subject, the method comprising administering to the subject an anti-CTLA-4 antibody or antigen-binding portion thereof comprising a heavy chain variable region comprising the amino acid sequence set forth in SEQ ID NO: 17 and a light chain variable region comprising the amino acid sequence set forth in SEQ ID NO: 7.

21. A method for increasing an immune response to an antigen in a subject, the method comprising administering to the subject an anti-CTLA-4 antibody or antigen-binding portion thereof comprising a heavy chain variable region comprising the amino acid sequence set forth in SEQ ID NO: 19 and a light chain variable region comprising the amino acid sequence set forth in SEQ ID NO: 9.

22. A method for increasing an immune response to an antigen in a subject, the method comprising administering to the subject an anti-CTLA-4 antibody or antigen-binding portion thereof comprising a heavy chain variable region comprising the amino acid sequence set forth in SEQ ID NO: 23 and a light chain variable region comprising the amino acid sequence set forth in SEQ ID NO: 13.

23. The method of any one of claims 1 and 16-22, wherein the antibody is a human antibody.

24. The method of any one of claims 1 and 16-22, wherein the antibody is a monoclonal antibody.

25. The method of any one of claims 1 and 16-22, wherein the antibody or antigen-binding portion thereof inhibits binding of human CTLA-4 to B7-1 or B7-2.

26. The method of any one of claims 1 and 16-22, wherein the antigen is a tumor antigen.

27. The method of claim 26, wherein the tumor antigen is selected from the group consisting of a prostate tumor antigen, a melanoma tumor antigen, an epithelial tumor antigen, and a combination thereof.

28. The method of any one of claims 1 and 16-22, further comprising administering an antigen, or a fragment or an analog thereof, to the subject, wherein administration of the antigen in combination with the antibody, or antigen-binding portion thereof, increases the immune response to the antigen.

29. The method of claim 28, wherein the antigen is a tumor antigen.

* * * * *